(12) United States Patent
Mylari

(10) Patent No.: US 6,570,013 B2
(45) Date of Patent: May 27, 2003

(54) SALTS OF ZOPOLRESTAT

(75) Inventor: Banavara L. Mylari, Waterford, CT (US)

(73) Assignee: Pfizer Inc, New York, NY (US)

(*) Notice: Subject to any disclaimer, the term of this patent is extended or adjusted under 35 U.S.C. 154(b) by 0 days.

(21) Appl. No.: 09/782,798

(22) Filed: Feb. 13, 2001

(65) Prior Publication Data

US 2001/0056095 A1 Dec. 27, 2001

Related U.S. Application Data

(60) Provisional application No. 60/183,004, filed on Feb. 16, 2000.

(51) Int. Cl.[7] .................. C07D 413/00; C07D 237/26; A61K 31/535; A61K 31/495
(52) U.S. Cl. ................. 544/235; 514/233.5; 514/235.5; 514/248; 544/111; 544/114; 544/115; 544/116
(58) Field of Search .............................. 514/248, 233.5, 514/235.5; 544/111, 114, 115, 116, 235

(56) References Cited

U.S. PATENT DOCUMENTS 4,939,140 A   7/1990   Larson et al. ............... 514/222

FOREIGN PATENT DOCUMENTS

| EP | 0222576 | 3/1992 |
|---|---|---|
| EP | 1106184 | 6/2001 |
| EP | 1106210 | 6/2001 |
| WO | WO9926659 | 6/1999 |
| WO | WO9943663 | 9/1999 |

*Primary Examiner*—Richard L. Raymond
*Assistant Examiner*—Tamthom N. Truong
(74) *Attorney, Agent, or Firm*—Peter C. Richardson; Gregg C. Benson; Robert T. Ronau

(57) ABSTRACT

This invention relates to [4-oxo-(5-trifluoromethyl-benzothiazol-2-ylmethyl)-3,4-dihydro-phthalazin-1-yl]-acetic acid ethanolamine salt, pharmaceutical compositions thereof and methods of treating diabetic complications in mammals comprising administering to said mammals said salt and said compositions. This invention is also directed to combinations of said diethylamine salt with NHE-1 inhibitors, selective serotonin retuptake inhibitors (SSRIs), glycogen phosphorylase inhibitors (GPIs), sorbitol dehydrogenase inhibitors (SDIs) and antihypertensive agents. Said combinations are useful in treating diabetic complications in mammals.

5 Claims, No Drawings

SALTS OF ZOPOLRESTAT

This application is filed claiming priority from co-pending Provisional Application No. 60/183,004 filed Feb. 16, 2000.

BACKGROUND OF THE INVENTION

This invention relates to [4-oxo-(5-trifluoromethyl-benzothiazol-2-ylmethyl)-3,4-dihydro-phthalazin-1-yl]-acetic acid ethanolamine salt, diethanolamine salt and triethanolamine salt, pharmaceutical compositions thereof and methods of treating diabetic complications in mammals comprising administering to said mammals said salts or said compositions. This invention is also directed to combinations of said salts with sodium hydrogen ion exchange (NHE-1) inhibitors, selective serotonin retuptake inhibitors (SSRIs), glycogen phosphorylase inhibitors (GPIs), sorbitol dehydrogenase inhibitors (SDIs) and antihypertensive agents. Said combinations are also useful in treating diabetic complications in mammals.

Zopolrestat, also known as [4-oxo-(5-trifluoromethyl-benzothiazol-2-ylmethyl)-3,4-dihydro-phthalazin-1-yl]-acetic acid, is disclosed in U.S. Pat. No. 4,939,140, which is incorporated herein by reference.

It is well known in the art that highly water soluble medicinal preparations, when administered orally, result in efficient absorption of such preparations from the gastrointestinal tract into systemic circulation. Another hallmark of such preparations is the rapid rate at which they are absorbed into the systemic circulation resulting in a high concentration of the active agent in the blood. Also, water soluble preparations are especially suitable for parenteral administration, for example, intravenous adminstration. The instant ethanolamine salt of this invention exhibits a surprising degree of water solubility.

SUMMARY OF THE INVENTION

This invention is directed to a salt form of zopolrestat selected from [4-oxo-(5-trifluoromethyl-benzothiazol-2-ylmethyl)-3,4-dihydro-phthalazin-1-yl]-acetic acid ethanolamine salt, also known as zopolrestat ethanolamine; [4-oxo-(5-trifluoromethyl-benzothiazol-2-ylmethyl)-3,4-dihydro-phthalazin-1-yl]-acetic acid diethanolamine salt, also known as zopolrestat diethanolamine; and [4-oxo-(5-trifluoromethyl-benzothiazol-2-ylmethyl)-3,4-dihydro-phthalazin-1-yl]-acetic acid triethanolamine salt, also known as zopolrestat triethanolamine. These compounds are salt forms of zopolrestat, which is the compound of the formula I

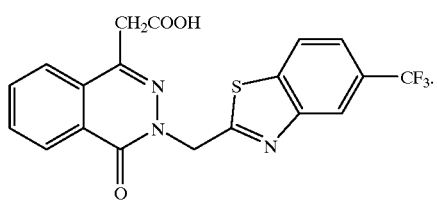

Zopolrestat ethanolamine has a water solubility of 40 mg/mL, zopolrestat diethanolamine has a water solubility of 100 mg/mL and zopolrestat triethanolamine has a water solubility of 6.6 mg/mL. As such, these salt forms of zopolrestat are highly water soluble forms of zopolrestat. Accordingly, these compounds are each advantageous salt forms of zopolrestat.

This invention is also directed to pharmaceutical compositions comprising zopolrestat ethanolamine, zopoirestat diethanolamine or zopolrestat triethanolamine and a pharmaceutically acceptable carrier, vehicle or diluent.

This invention is also directed to a pharmaceutical composition comprising zopolrestat ethanolamine, zopolrestat diethanolamine or zopolrestat triethanolamine and a second pharmaceutical agent. Said second pharmaceutical agents include NHE-1 inhibitors, SSRIs, GPIs, SDIs and antihypertensive agents. Particularly preferred SSRIs for use in this invention are fluoxetine, sertraline and sibutramine or a pharmaceutically acceptable salt of said fluoxetine, sertraline or sibutramine. It is particularly preferred that said SSRI is sertraline hydrochloride. It is also preferred that said antihypertensive agents are ACE inhibitors. Particularly preferred ACE inhibitors for use in this invention are enalapril and captopril.

This invention is also directed to a method of treating diabetic complications in mammals comprising administering to said mammal zopolrestat ethanolamine, zopolrestat diethanolamine or zopolrestat triethanolamine. Diabetic complications which are treated by zopoirestat ethanolamine, zopolrestat diethanolamine or zopolrestat triethanolamine, pharmaceutical compositions comprising zopolrestat ethanolamine, zopolrestat diethanolamine or zopolrestat triethanolamine and the combinations of this invention include, but are not limited to, diabetic neuropathy, diabetic nephropathy, diabetic cardiomyopathy, diabetic retinopathy, microangiopathy, macroangiopathy, cataracts and myocardial infarction.

This invention is also directed to a method of treating diabetic complications in mammals comprising administering to said mammal a pharmaceutical composition comprising a combination of zopolrestat ethanolamine, zopolrestat diethanolamine or zopolrestat triethanolamine and a second pharmaceutical agent or a pharmaceutically acceptable salt of said second pharmaceutical agent where said second pharmaceutical agent is an NHE-1 inhibitor, a SSRI, a GPI, a SDI or an antihypertensive agent.

This invention is also directed to a kit comprising:

a) a first unit dosage form comprising zopolrestat ethanolamine, zopolrestat diethanolamine or zopolrestat triethanolamine and a pharmaceutically acceptable carrier, vehicle or diluent;

b) a second unit dosage form comprising a second pharmaceutical agent, a prodrug thereof or a pharmaceutically acceptable salt of said second pharmaceutical agent or said prodrug and a pharmaceutically acceptable carrier, vehicle or diluent; and c) a container.

25. This invention is particularly directed to such a kit wherein said second pharmaceutical agent is a sodium/hydrogen ion exchange (NHE-1) inhibitor, a selective serotonin retuptake inhibitor (SSRI), a glycogen phosphorylase inhibitor (GPI), a sorbitol dehydrogenase inhibitor (SDI) or an antihypertensive agent.

The term "treating", "treat" or "treatment" as used herein includes curative, preventative (e.g., prophylactic) and palliative treatment.

DETAILED DESCRIPTION OF THE INVENTION

The salts of this invention, i.e., zopolrestat ethanolamine, also known as [4-oxo-(5-trifluoromethyl-benzothiazol-2-ylmethyl)-3,4-dihydro-phthalazin-1-yl]-acetic acid ethanolamine salt; zopolrestat diethanolamine, also known as

[4-oxo-(5-trifluoromethyl-benzothiazol-2-ylmethyl)-3,4-dihydro-phthalazin-1-yl]-acetic acid diethanolamine salt; and zopolrestat triethanolamine, also known as [4-oxo-(5-trifluoromethyl-benzothiazol-2-ylmethyl)-3,4-dihydro-phthalazin-1-yl]-acetic acid ethanolamine salt, are readily prepared as set forth below.

4-Oxo-(5-trifluoromethyl-benzothiazol-2-ylmethyl)-3,4-dihydro-phthalazin-1-yl]-acetic acid, also known as zopolrestat, is dissolved in an appropriate reaction inert solvent. As used herein, the expression "reaction inert solvent" refers to a solvent or mixture of solvents which does not interact with starting materials, reagents, intermediates or products in a manner which adversely affects the yield of the desired product. Preferred solvents include methanol, ethanol, n-propanol, isopropanol, acetone, ethyl methyl ketone, diethyl ketone and methyl isobutyl ketone. A particularly preferred solvent for this reaction is acetone. To this solution is added ethanolamine, diethanolamine or triethanolamine. The reaction mixture is stirred at about ambient temperature to about the refluxing temperature of the solvent being used for about two hours to about six hours, preferably at ambient temperature for about two hours. The salt of this invention is isolated from the reaction mixture by methods well known to those skilled in the art. It is preferred that the reaction mixture is directly evaporated. The residue from the evaporation is preferably crystallized from an appropriate solvent or mixture of solvents.

Zopolrestat is prepared as disclosed in U.S. Pat. No. 4,939,140, which is incorporated herein by reference. Methods for measuring the aldose reductase inhibitory activity of the compounds and compositions of this invention are disclosed therein.

Measurement of the water solubility of the salts of this invention is accomplished by using methods well known to those skilled in the art. Specifically, to a weighed amount of zopolrestat ethanolamine, zopolrestat diethanolamine or zopolrestat triethanolamine, distilled water is added in small portions until a clear solution is obtained. The total volume of the solution is measured. The water solubility of the particular zopolrestat salt, in mg/mL, is calculated by dividing the weight of the salt, in mg, by the volume of the solution, in mL. The water solubility of zopolrestat ethanolamine salt, when measured using the above technique, was determined to be 40 mg/mL. Likewise, the water solubility of zopolrestat diethanolamine was determined to be 100 mg/mL and the water solubility of zopolrestat triethanolamine was determined to be 6.6 mg/mL.

Any selective serotonin reuptake inhibitor (SSRI) may be used as the second pharmaceutical agent in the pharmaceutical compositions, methods and kits of this invention. The term selective serotonin reuptake inhibitor refers to a compound which inhibits the reuptake of serotonin by afferent neurons. Such inhibition is readily determined by those skilled in the art according to standard assays such as those disclosed in U.S. Pat. No. 4,536,518 and other U.S. patents recited in the next paragraph.

Preferred selective serotonin reuptake inhibitors (SSRI) which may be used in accordance with this invention include, but are not limited to: femoxetine, which may be prepared as described in U.S. Pat. No. 3,912,743; fluoxetine, which may be prepared as described in U.S. Pat. No. 4,314,081; fluvoxamine, which may be prepared as described in U.S. Pat. No. 4,085,225; indalpine, which may be prepared as described in U.S. Pat. No. 4,064,255; indeloxazine, which may be prepared as described in U.S. Pat. No. 4,109,088; milnacipran, which may be prepared as described in U.S. Pat. No. 4,478,836; paroxetine, which may be prepared as described in U.S. Pat. No. 3,912,743 or U.S. Pat. No. 4,007,196; sertraline, which may be prepared as described in U.S. Pat. No. 4,536,518; sibutramine, which may be prepared as described in U.S. Pat. No. 4,929,629; and zimeldine, which may be prepared as described in U.S. Pat. No. 3,928,369. Fluoxetine is also known as Prozac®. Sertraline is also known as Zoloft®. Sibutramine is also known as Meridia®. The disclosures thereof are incorporated herein by reference.

Any antihypertensive agent may be used as the second pharmaceutical agent in the pharmaceutical compositions, methods and kits of this invention. Preferred classes of antihypertensive agents include angiotensin converting enzyme (ACE) inhibitors, calcium channel blockers, angiotensin (A-II) antagonists, diuretics, endopeptidase inhibitors, beta-adrenergic receptor blockers, vasodilators and alpha-adrenergic receptor blockers.

ACE inhibitors which are within the scope of this invention include, but are not limited to: alacepril, which may be prepared as disclosed in U.S. Pat. No. 4,248,883; benazepril, which may be prepared as disclosed in U.S. Pat. No. 4,410,520; captopril, which may be prepared as disclosed in U.S. Pat. Nos. 4,046,889 and 4,105,776; ceronapril, which may be prepared as disclosed in U.S. Pat. No. 4,452,790; delapril, which may be prepared as disclosed in U.S. Pat. No. 4,385,051; enalapril, which may be prepared as disclosed in U.S. Pat. No. 4,374,829; fosinopril, which may be prepared as disclosed in U.S. Pat. No. 4,337,201; imadapril, which may be prepared as disclosed in U.S. Pat. No. 4,508,727; lisinopril, which may be prepared as disclosed in U.S. Pat. No. 4,555,502; moveltopril, which may be prepared as disclosed in Belgian Patent No. 893,553; perindopril, which may be prepared as disclosed in U.S. Pat. No. 4,508,729; quinapril, which may be prepared as disclosed in U.S. Pat. No. 4,344,949; ramipril, which may be prepared as disclosed in U.S. Pat. No. 4,587,258; spirapril, which may be prepared as disclosed in U.S. Pat. No. 4,470,972; temocapril, which may be prepared as disclosed in U.S. Pat. No. 4,699,905; and trandolapril, which may be prepared as disclosed in U.S. Pat. No. 4,933,361. The disclosures of all such U.S. patents are incorporated herein by reference.

Calcium channel blockers which are within the scope of this invention include, but are not limited to: bepridil, which may be prepared as disclosed in U.S. Pat. No. 3,962,238 or U.S. Reissue No. 30,577; clentiazem, which may be prepared as disclosed in U.S. Pat. No. 4,567,175; diltiazem, which may be prepared as disclosed in U.S. Pat. No. 3,562,257 fendiline, which may be prepared as disclosed in U.S. Pat. No. 3,262,977; gallopamil, which may be prepared as disclosed in U.S. Pat. No. 3,261,859; mibefradil, which may be prepared as disclosed in U.S. Pat. No. 4,808,605; prenylamine, which may be prepared as disclosed in U.S. Pat. No. 3,152,173; semotiadil, which may be prepared as disclosed in U.S. Pat. No. 4,786,635; terodiline, which may be prepared as disclosed in U.S. Pat. No. 3,371,014; verapamil, which may be prepared as disclosed in U.S. Pat. No. 3,261,859; amlodipine, which may be prepared as disclosed in U.S. Pat. No. 4,5723,909; aranipine, which may be prepared as disclosed in U.S. Pat. No. 4,572,909; barnidipine, which may be prepared as disclosed in U.S. Pat. No. 4,220,649; benidipine, which may be prepared as disclosed in European Patent Application Publication No. 106,275; cilnidipine, which may be prepared as disclosed in U.S. Pat. No. 4,672,068; efonidipine, which may be prepared as disclosed in U.S. Pat. No. 4,885,284; elgodipine, which may be prepared as disclosed in U.S. Pat. No. 4,952,592; felodipine, which may be prepared as disclosed in U.S. Pat. No. 4,264,611; isradipine, which may be prepared as disclosed in U.S. Pat. No. 4,466,972; lacidipine, which may be prepared as disclosed in U.S. Pat. No. 4,801,599; lercanidipine, which may be prepared as disclosed in U.S. Pat. No. 4,705,797; manidipine, which may be prepared as disclosed in U.S. Pat. No. 4,892,875; nicardipine, which may be prepared as disclosed in U.S. Pat. No. 3,985,758; nifedipine, which may be prepared as disclosed in U.S. Pat. No. 3,485,847; nilvadipine, which may be prepared as disclosed in U.S. Pat. No. 4,338,322; nimodipine, which may be prepared as disclosed in U.S. Pat. No. 3,799,934; nisoldipine, which may be prepared as disclosed in U.S. Pat. No. 4,154,839; nitrendipine, which may be prepared as disclosed in U.S. Pat. No. 3,799,934; cinnarizine, which may be prepared as disclosed in U.S. Pat. No. 2,882,271; flunarizine, which may be prepared as disclosed in U.S. Pat. No. 3,773,939; lidoflazine, which may be prepared as disclosed in U.S. Pat. No. 3,267,104; lomerizine, which may be prepared as disclosed in U.S. Pat. No. 4,663,325; bencyclane, which may be prepared as disclosed in Hungarian Patent No. 151,865; etafenone, which may be prepared as disclosed in German Patent No. 1,265,758; and perhexiline, which may be prepared as disclosed in British Patent No. 1,025,578. Amlodipine besylate, a preferred salt of amlodipine, is disclosed in U.S. Pat. No. 4,879,303. The disclosures thereof are incorporated herein by reference.

Angiotensin-II receptor antagonists (A-II antagonists) which are within the scope of this invention include, but are not limited to: candesartan, which may be prepared as disclosed in U.S. Pat. No. 5,196,444; eprosartan, which may be prepared as disclosed in U.S. Pat. No. 5,185,351; irbesartan, which may be prepared as disclosed in U.S. Pat. No. 5,270,317; losartan, which may be prepared as disclosed in U.S. Pat. No. 5,138,069; and valsartan, which may be prepared as disclosed in U.S. Pat. No. 5,399,578. The disclosures thereof are incorporated herein by reference.

Beta-adrenergic receptor blockers (beta- or β-blockers) which are within the scope of this invention include, but are not limited to: acebutolol, which may be prepared as disclosed in U.S. Pat. No. 3,857,952; alprenolol, which may be prepared as disclosed in Netherlands Patent Application No. 6,605,692; amosulalol, which may be prepared as disclosed in U.S. Pat. No. 4,217,305; arotinolol, which may be prepared as disclosed in U.S. Pat. No. 3,932,400; atenolol, which may be prepared as disclosed in U.S. Pat. No. 3,663,607 or 3,836,671; befunolol, which may be prepared as disclosed in U.S. Pat. No. 3,853,923; betaxolol, which may be prepared as disclosed in U.S. Pat. No. 4,252,984; bevantolol, which may be prepared as disclosed in U.S. Pat. No. 3,857,981; bisoprolol, which may be prepared as disclosed in U.S. Pat. No. 4,171,370; bopindolol, which may be prepared as disclosed in U.S. Pat. No. 4,340,541; bucumolol, which may be prepared as disclosed in U.S. Pat. No. 3,663,570; bufetolol, which may be prepared as disclosed in U.S. Pat. No. 3,723,476; bufuralol, which may be prepared as disclosed in U.S. Pat. No. 3,929,836; bunitrolol, which may be prepared as disclosed in U.S. Pat. Nos. 3,940,489 and 3,961,071; buprandolol, which may be prepared as disclosed in U.S. Pat. No. 3,309,406; butiridine hydrochloride, which may be prepared as disclosed in French Patent No. 1,390,056; butofilolol, which may be prepared as disclosed in U.S. Pat. No. 4,252,825; carazolol, which may be prepared as disclosed in German Patent No. 2,240,599; carteolol, which may be prepared as disclosed in U.S. Pat. No. 3,910,924; carvedilol, which may be prepared as disclosed in U.S. Pat. No. 4,503,067; celiprolol, which may be prepared as disclosed in U.S. Pat. No. 4,034,009; cetamolol, which may be prepared as disclosed in U.S. Pat. No. 4,059,622; cloranolol, which may be prepared as disclosed in German Patent No. 2,213,044; dilevalol, which may be prepared as disclosed in Clifton et al., Journal of Medicinal Chemistry, 1982, 25, 670; epanolol, which may be prepared as disclosed in European Patent Publication Application No. 41,491; indenolol, which may be prepared as disclosed in U.S. Pat. No. 4,045,482; labetalol, which may be prepared as disclosed in U.S. Pat. No. 4,012,444; levobunolol, which may be prepared as disclosed in U.S. Pat. No. 4,463,176; mepindolol, which may be prepared as disclosed in Seeman et al., Helv. Chim. Acta, 1971, 54, 241; metipranolol, which may be prepared as disclosed in Czechoslovakian Patent Application No. 128,471; metoprolol, which may be prepared as disclosed in U.S. Pat. No. 3,873,600; moprolol, which may be prepared as disclosed in U.S. Pat. No. 3,501,769; nadolol, which may be prepared as disclosed in U.S. Pat. No. 3,935,267; nadoxolol, which may be prepared as disclosed in U.S. Pat. No. 3,819,702; nebivalol, which may be prepared as disclosed in U.S. Pat. No. 4,654,362; nipradilol, which may be prepared as disclosed in U.S. Pat. No. 4,394,382; oxprenolol, which may be prepared as disclosed in British Patent No. 1,077,603; perbutolol, which may be prepared as disclosed in U.S. Pat. No. 3,551,493; pindolol, which may be prepared as disclosed in Swiss Patent Nos. 469,002 and 472,404; practolol, which may be prepared as disclosed in U.S. Pat. No. 3,408,387; pronethalol, which may be prepared as disclosed in British Patent No. 909,357; propranolol, which may be prepared as disclosed in U.S. Pat. Nos. 3,337,628 and 3,520,919; sotalol, which may be prepared as disclosed in Uloth et al., Journal of Medicinal Chemistry, 1966, 9, 88; sufinalol, which may be prepared as disclosed in German Patent No. 2,728,641; talindol, which may be prepared as disclosed in U.S. Pat. Nos. 3,935,259 and 4,038,313; tertatolol, which may be prepared as disclosed in U.S. Pat. No. 3,960,891; tilisolol, which may be prepared as disclosed in U.S. Pat. No. 4,129,565; timolol, which may be prepared as disclosed in U.S. Pat. No. 3,655,663; toliprolol, which may be prepared as disclosed in U.S. Pat. No. 3,432,545; and xibenolol, which may be prepared as disclosed in U.S. Pat. No. 4,018,824. The disclosures thereof are incorporated herein by reference.

Endopeptidase inhibitors which are within the scope of this invention include, but are not limited to sampatrilat, which may be prepared as disclosed in European Patent Application Publication No. EP 358398; candoxatril and candoxatrilat, each of which may be prepared as disclosed in European Patent Application Publication No. EP 274234; and omapatrilat, which may be prepared as disclosed in U.S. Pat. No. 5,508,272. The disclosures thereof are incorporated herein by reference.

Alpha-adrenergic recept or blockers (alpha- or α-blockers) which are within the scope of this invention include, but are not limited to: amosulalol, which may be prepared as disclosed in U.S. Pat. No. 4,217,307; arotinolol, which may be prepared as disclosed in U.S. Pat. No. 3,932,400; dapiprazole, which may be prepared as disclosed in U.S. Pat. No. 4,252,721; doxazosin, which may be prepared as disclosed in U.S. Pat. No. 4,188,390; fenspiride, which may be prepared as disclosed in U.S. Pat. No. 3,399,192; indoramin, which may be prepared as disclosed in U.S. Pat. No. 3,527,761; labetolol, which may be prepared as disclosed above; naftopidil, which may be prepared as disclosed in U.S. Pat. No. 3,997,666; nicergoline, which may be prepared as disclosed in U.S. Pat. No. 3,228,943; prazosin, which may be prepared as disclosed in U.S. Pat. No. 3,511,836; tamsulosin, which may be prepared as disclosed in U.S. Pat. No. 4,703,063; tolazoline, which may be prepared as disclosed in U.S. Pat. No. 2,161,938; trimazosin, which may be prepared as disclosed in U.S. Pat. No. 3,669,968; and yohimbine, which may be isolated from natural sources according to methods well known to those skilled in the art. The disclosures thereof are incorporated herein by reference.

The term "vasodilator," where used herein, is meant to include cerebral vasodilators, coronary vasodilators and peripheral vasodilators. Cerebral vasodilators within the scope of this invention include, but are not limited to: bencyclane, which may be prepared as disclosed above; cinnarizine, which may be prepared as disclosed above; citicoline, which may be isolated from natural sources as disclosed in Kennedy et al., Journal of the American Chemical Society, 1955, 77, 250 or synthesized as disclosed in Kennedy, Journal of Biological Chemistry, 1956, 222, 185; cyclandelate, which may be prepared as disclosed in U.S. Pat. No. 3,663,597; ciclonicate, which may be prepared as disclosed in German Patent No. 1,910,481; diisopropylamine dichloroacetate, which may be prepared as disclosed in British Patent No. 862,248; eburnamonine, which may be prepared as disclosed in Hermann et al., Journal of the American Chemical Society, 1979, 101, 1540; fasudil, which may be prepared as disclosed in U.S. Pat. No. 4,678,783; fenoxedil, which may be prepared as disclosed in U.S. Pat. No. 3,818,021; flunarizine, which may be prepared as disclosed in U.S. Pat. No. 3,773,939; ibudilast, which may be prepared as disclosed in U.S. Pat. No. 3,850,941; ifenprodil, which may be prepared as disclosed in U.S. Pat. No. 3,509,164; lomerizine, which may be prepared as disclosed in U.S. Pat. No. 4,663,325; nafronyl, which may be prepared as disclosed in U.S. Pat. No. 3,334,096; nicametate, which may be prepared as disclosed in Blicke et al., Journal of the American Chemical Society, 1942, 64, 1722; nicergoline, which may be prepared as disclosed above; nimodipine, which may be prepared as disclosed in U.S. Pat. No. 3,799,934; papaverine, which may be prepared as reviewed in Goldberg, Chem. Prod. Chem. News, 1954, 17, 371; pentifylline, which may be prepared as disclosed in German Patent No. 860,217; tinofedrine, which may be prepared as disclosed in U.S. Pat. No. 3,563,997; vincamine, which may be prepared as disclosed in U.S. Pat. No. 3,770,724; vinpocetine, which may be prepared as disclosed in U.S. Pat. No. 4,035,750; and viquidil, which may be prepared as disclosed in U.S. Pat. No. 2,500,444. The disclosures thereof are incorporated herein by reference.

Coronary vasodilators within the scope of this invention include, but are not limited to: amotriphene, which may be prepared as disclosed in U.S. Pat. No. 3,010,965; bendazol, which may be prepared as disclosed in J. Chem. Soc. 1958, 2426; benfurodil hemisuccinate, which may be prepared as disclosed in U.S. Pat. No. 3,355,463; benziodarone, which may be prepared as disclosed in U.S. Pat. No. 3,012,042; chloracizine, which may be prepared as disclosed in British Patent No. 740,932; chromonar, which may be prepared as disclosed in U.S. Pat. No. 3,282,938; clobenfural, which may be prepared as disclosed in British Patent No. 1,160,925; clonitrate, which may be prepared from propanediol according to methods well known to those skilled in the art, e.g., see *Annalen,* 1870, 155, 165; cloricromen, which may be prepared as disclosed in U.S. Pat. No. 4,452,811; dilazep, which may be prepared as disclosed in U.S. Pat. No. 3,532,685; dipyridamole, which may be prepared as disclosed in British Patent No. 807,826; droprenilamine, which may be prepared as disclosed in German Patent No. 2,521,113; efloxate, which may be prepared as disclosed in British Patent Nos. 803,372 and 824,547; erythrityl tetranitrate, which may be prepared by nitration of erythritol according to methods well-known to those skilled in the art; etafenone, which may be prepared as disclosed in German Patent No. 1,265,758; fendiline, which may be prepared as disclosed in U.S. Pat. No. 3,262,977; floredil, which may be prepared as disclosed in German Patent No. 2,020,464; ganglefene, which may be prepared as disclosed in U.S.S.R. Patent No. 115,905; hexestrol, which may be prepared as disclosed in U.S. Pat. No. 2,357,985; hexobendine, which may be prepared as disclosed in U.S. Pat. No. 3,267,103; itramin tosylate, which may be prepared as disclosed in Swedish Patent No. 168,308; khellin, which may be prepared as disclosed in Baxter et al., Journal of the Chemical Society, 1949, S 30; lidoflazine, which may be prepared as disclosed in U.S. Pat. No. 3,267,104; mannitol hexanitrate, which may be prepared by the nitration of mannitol according to methods well-known to those skilled in the art; medibazine, which may be prepared as disclosed in U.S. Pat. No. 3,119,826; nitroglycerin; pentaerythritol tetranitrate, which may be prepared by the nitration of pentaerythritol according to methods well-known to those skilled in the art; pentrinitrol, which may be prepared as disclosed in German Patent No. 638,422–3; perhexilline, which may be prepared as disclosed above; pimefylline, which may be prepared as disclosed in U.S. Pat. No. 3,350,400; prenylamine, which may be prepared as disclosed in U.S. Pat. No. 3,152,173; propatyl nitrate, which may be prepared as disclosed in French Patent No. 1,103,113; trapidil, which may be prepared as disclosed in East German Patent No. 55,956; tricromyl, which may be prepared as disclosed in U.S. Pat. No. 2,769,015; trimetazidine, which may be prepared as disclosed in U.S. Pat. No. 3,262,852; trolnitrate phosphate, which may be prepared by nitration of triethanolamine followed by precipitation with phosphoric acid according to methods well-known to those skilled in the art; visnadine, which may be prepared as disclosed in U.S. Pat. Nos. 2,816,118 and 2,980,699. The disclosures thereof are incorporated herein by reference.

Peripheral vasodilators within the scope of this invention include, but are not limited to: aluminum nicotinate, which may be prepared as disclosed in U.S. Pat. No. 2,970,082; bamethan, which may be prepared as disclosed in Corrigan et al., Journal of the American Chemical Society, 1945, 67, 1894; bencyclane, which may be prepared as disclosed above; betahistine, which may be prepared as disclosed in Walter et al.; Journal of the American Chemical Society, 1941, 63, 2771; bradykinin, which may be prepared as disclosed in Hamburg et al., Arch. Biochem. Biophys., 1958, 76, 252; brovincamine, which may be prepared as disclosed in U.S. Pat. No. 4,146,643; bufeniode, which may be prepared as disclosed in U.S. Pat. No. 3,542,870; buflomedil, which may be prepared as disclosed in U.S. Pat. No. 3,895,030; butalamine, which may be prepared as disclosed in U.S. Pat. No. 3,338,899; cetiedil, which may be prepared as disclosed in French Patent Nos. 1,460,571; ciclonicate, which may be prepared as disclosed in German Patent No. 1,910,481; cinepazide, which may be prepared as disclosed in Belgian Patent No. 730,345; cinnarizine, which may be prepared as disclosed above; cyclandelate, which may be prepared as disclosed above; diisopropylamine dichloroacetate, which may be prepared as disclosed above; eledoisin, which may be prepared as disclosed in British Patent No. 984,810; fenoxedil, which may be prepared as disclosed above; flunarizine, which may be prepared as disclosed above; hepronicate, which may be prepared as disclosed in U.S. Pat. No. 3,384,642; ifenprodil, which may be prepared as disclosed above; iloprost, which may be prepared as disclosed in U.S. Pat. No. 4,692,464; inositol niacinate, which may be prepared as disclosed in Badgeft et al., Journal of the American Chemical Society, 1947, 69, 2907; isoxsuprine, which may be prepared as disclosed in U.S. Pat. No. 3,056,836; kallidin, which may be prepared as disclosed in *Biochem. Biophys. Res. Commun.*, 1961, 6, 210; kallikrein, which may be prepared as disclosed in German Patent No. 1,102,973; moxisylyte, which may be prepared as disclosed in German Patent No. 905,738; nafronyl, which may be prepared as disclosed above; nicametate, which may be prepared as disclosed above; nicergoline, which may be prepared as disclosed above; nicofuranose, which may be prepared as disclosed in Swiss Patent No. 366,523; nylidrin, which may be prepared as disclosed in U.S. Pat. Nos. 2,661,372 and 2,661,373; pentifylline, which may be prepared as disclosed above; pentoxifylline, which may be prepared as disclosed in U.S. Pat. No. 3,422,107; piribedil, which may be prepared as disclosed in U.S. Pat. No. 3,299,067; prostaglandin $E_1$, which may be prepared by any of the methods referenced in the Merck Index, Twelfth Edition, Budaveri, Ed., New Jersey, 1996, p. 1353; suloctidil, which may be prepared as disclosed in German Patent No. 2,334,404; tolazoline, which may be prepared as disclosed in U.S. Pat. No. 2,161,938; and xanthinol niacinate, which may be prepared as disclosed in German Patent No. 1,102,750 or Korbonits et al., Acta. Pharm. Hung., 1968, 38, 98. The disclosures thereof are incorporated herein by reference.

The term "diuretic," within the scope of this invention, is meant to include diuretic benzothiadiazine derivatives, diuretic organomercurials, diuretic purines, diuretic steroids, diuretic sulfonamide derivatives, diuretic uracils and other diuretics such as amanozine, which may be prepared as disclosed in Austrian Patent No. 168,063; amiloride, which may be prepared as disclosed in Belgian Patent No. 639,386; arbutin, which may be prepared as disclosed in Tschitschibabin, Annalen, 1930, 479, 303; chlorazanil, which may be prepared as disclosed in Austrian Patent No. 168,063; ethacrynic acid, which may be prepared as disclosed in U.S. Pat. No. 3,255,241; etozolin, which may be prepared as disclosed in U.S. Pat. No. 3,072,653; hydracarbazine, which may be prepared as disclosed in British Patent No. 856,409; isosorbide, which may be prepared as disclosed in U.S. Pat. No. 3,160,641; mannitol; metochalcone, which may be prepared as disclosed in Freudenberg et al., Ber., 1957, 90, 957; muzolimine, which may be prepared as disclosed in U.S. Pat. No. 4,018,890; perhexiline, which may be prepared as disclosed above; ticrynafen, which may be prepared as disclosed in U.S. Pat. No. 3,758,506; triamterene which may be prepared as disclosed in U.S. Pat. No. 3,081,230; and urea. The disclosures thereof are incorporated herein by reference.

Diuretic benzothiadiazine derivatives within the scope of this invention include, but are not limited to: althiazide, which may be prepared as disclosed in British Patent No. 902,658; bendroflumethiazide, which may be prepared as disclosed in U.S. Pat. No. 3,265,573; benzthiazide, McManus et al., 136th Am. Soc. Meeting (Atlantic City, September 1959), Abstract of papers, pp 13–0; benzylhydrochlorothiazide, which may be prepared as disclosed in U.S. Pat. No. 3,108,097; buthiazide, which may be prepared as disclosed in British Patent Nos. 861,367 and 885,078; chlorothiazide, which may be prepared as disclosed in U.S. Pat. Nos. 2,809,194 and 2,937,169; chlorthalidone, which may be prepared as disclosed in U.S. Pat. No. 3,055,904; cyclopenthiazide, which may be prepared as disclosed in Belgian Patent No. 587,225; cyclothiazide, which may be disclosed in Whitehead et al., Journal of Organic Chemistry, 1961, 26, 2814; epithiazide, which may be prepared as disclosed in U.S. Pat. No. 3,009,911; ethiazide, which may be prepared as disclosed in British Patent No. 861,367; fenquizone, which may be prepared as disclosed in U.S. Pat. No. 3,870,720; indapamide, which may be prepared as disclosed in U.S. Pat. No. 3,565,911; hydrochlorothiazide, which may be prepared as disclosed in U.S. Pat. No. 3,164,588; hydroflumethiazide, which may be prepared as disclosed in U.S. Pat. No. 3,254,076; methyclothiazide, which may be prepared as disclosed in Close et al., Journal of the American Chemical Society, 1960, 82, 1132; meticrane, which may be prepared as disclosed in French Patent Nos. M2790 and 1,365,504; metolazone, which may be prepared as disclosed in U.S. Pat. No. 3,360,518; paraflutizide, which may be prepared as disclosed in Belgian Patent No. 620,829; polythiazide, which may be prepared as disclosed in U.S. Pat. No. 3,009,911; quinethazone, which may be prepared as disclosed in U.S. Pat. No. 2,976,289; teclothiazide, which may be prepared as disclosed in Close et al., Journal of the American Chemical Society, 1960, 82, 1132; and trichlormethiazide, which may be prepared as dislcosed in deStevens et al., Experientia, 1960, 16, 113. The disclosures thereof are incorporated herein by reference.

Diuretic sulfonamide derivatives within the scope of this invention include, but are not limited to: acetazolamide, which may be prepared as disclosed in U.S. Pat. No. 2,980,679; ambuside, which may be prepared as disclosed in U.S. Pat. No. 3,188,329; azosemide, which may be prepared as disclosed in U.S. Pat. No. 3,665,002; bumetanide, which may be prepared as disclosed in U.S. Pat. No. 3,634,583; butazolamide, which may be prepared as disclosed in British Patent No. 769,757; chloraminophenamide, which may be prepared as disclosed in U.S. Pat. Nos. 2,809,194, 2,965,655 and 2,965,656; clofenamide, which may be prepared as disclosed in Olivier, Rec. Trav. Chim., 1918, 37, 307; clopamide, which may be prepared as disclosed in U.S. Pat. No. 3,459,756; clorexolone, which may be prepared as disclosed in U.S. Pat. No. 3,183,243; disulfamide, which may be prepared as disclosed in British Patent No. 851,287; ethoxolamide, which may be prepared as disclosed in British Patent No. 795,174; furosemide, which may be prepared as disclosed in U.S. Pat. No. 3,058,882; mefruside, which may be prepared as disclosed in U.S. Pat. No. 3,356,692; methazolamide, which may be prepared as disclosed in U.S. Pat. No. 2,783,241; piretanide, which may be prepared as disclosed in U.S. Pat. No. 4,010,273; torasemide, which may be prepared as disclosed in U.S. Pat. No. 4,018,929; tripamide, which may be prepared as disclosed in Japanese Patent No. 73 05,585; and xipamide, which may be prepared as disclosed in U.S. Pat. No. 3,567,777. The disclosures thereof are incorporated herein by reference.

Any NHE-1 inhibitor may be used as the second pharmaceutical agent in the pharmaceutical compositions, methods and kits of this invention. The term NHE-1 inhibitor refers to compounds which inhibit the sodium/proton ($Na^+$/$H^+$) exchange transport system and hence are useful as a therapeutic or prophylactic agent for diseases caused or aggravated by the acceleration of the sodium/proton ($Na^+$/$H^+$) exchange transport system, for example, cardiovascular diseases [e.g., arteriosclerosis, hypertension, arrhythmia (e.g. ischemic arrhythmia, arrhythmia due to myocardial infarction, myocardial stunning, myocardial dysfunction, arrhythmia after PTCA or after thrombolysis, etc.), angina pectoris, cardiac hypertrophy, myocardial infarction, heart failure (e.g. congestive heart failure, acute heart failure, cardiac hypertrophy, etc.), restenosis after PTCA, PTCI, shock (e.g. hemorrhagic shock, endotoxin shock, etc.)], renal diseases (e.g. diabetes mellitus, diabetic nephropathy, ischemic acute renal failure, etc.) organ disorders associated with ischemia or ischemic reperfusion [e.g. heart muscle ischemic reperfusion associated disorders, acute renal failure, or disorders induced by surgical treatment such as coronary artery bypass grafting (CABG) surgeries, vascular surgeries, organ transplantation, non-cardiac surgeries or percutaneous transluminal coronary angioplasty (PTCA)], cerebrovascular diseases (e.g. ischemic stroke, hemorrhagic stroke, etc.), cerebro ischemic disorders (e.g. disorders associated with cerebral infarction, disorders caused after cerebral apoplexy as sequelae, or cerebral edema. NHE-1 inhibitors can also be used as an agent for myocardial protection during coronary artery bypass grafting (CABG) surgeries, vascular surgeries, percutaneous transluminal coronary angioplasty (PTCA), PTCI, organ transplantation, or non-cardiac surgeries. The utility of NHE-1 inhibitors as medical agents in the treatment of diseases, such as are detailed herein in mammals (e.g. humans) for example, myocardial protection during surgery or mycardial protection in patients presenting with ongoing cardiac or cerebral ischemic events or chronic cardioprotection in patients with diagnosed coronary heart disease, or at risk for coronary heart disease, cardiac dysfunction or myocardial stunning is demonstrated by the activity of the compounds of formula I of this invention in conventional preclinical cardioprotection assays [see the in vivo assay in Klein, H. et al., Circulation 92:912–917 (1995); the isolated heart assay in Scholz, W. et al., Cardiovascular Research 29:260–268 (1995); the anti-arrhythmic assay in Yasutake M. et al., Am. J. Physiol., 36:H2430–H2440 (1994); the NMR assay in Kolke et al., J. Thorac. Cardiovasc. Surg. 112: 765–775 (1996)] and the additional in vitro and in vivo assays described below. Such assays also provide a means whereby the activities of the compounds of formula I of this invention can be compared with the activities of other known compounds. The results of these comparisons are useful for determining dosage levels in mammals, including humans, for the treatment of such diseases.

NHE-1 inhibitors are disclosed in U.S. Pat. No. 5,698,581, European Patent Application Publication No. EP 803 501 A1, International Patent Application Publication Nos. WO 94/26709 and PCT/JP97/04650, each of which is incorporated herein by reference. The NHE-1 inhibitors disclosed therein have utility in the combination of this invention. Said NHE-1 inhibitors can be prepared as disclosed therein.

Preferred NHE-1 inhibitors include compounds of the formula NHE,

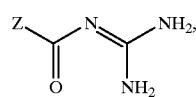

NHE a prodrug thereof or a pharmaceutically acceptable salt of said compound or of said prodrug, wherein Z in the compound of formula NHE is carbon connected and is a five-membered, diaza, diunsaturated ring having two contiguous nitrogens, said ring optionally mono-, di-, or tri-substituted with up to three substituents independently selected from $R^1$, $R^2$ and $R^3$;

or

Z in the compound of formula NHE carbon connected and is a five-membered, triaza, diunsaturated ring, said ring optionally mono- or di-substituted with up to two substituents independently selected from $R^4$ and $R^5$; wherein $R^1$, $R^2$, $R^3$, $R^4$ and $R^5$ in the compound of formula NHE are each independently hydrogen, hydroxy-($C_1$–$C_4$)alkyl, ($C_1$–$C_4$)alkyl, ($C_1$–$C_4$)alkylthio, ($C_3$–$C_4$)cycloalkyl, ($C_3$–$C_7$)cycloalkyl ($C_1$–$C_4$)alkyl, ($C_1$–$C_4$)alkoxy, ($C_1$–$C_4$)alkoxy($C_1$–$C_4$)alkyl, mono-N- or di-N,N-($C_1$–$C_4$)alkylcarbamoyl, M or M($C_1$–$C_4$)alkyl, any of said previous ($C_1$–$C_4$)alkyl moieties optionally having from one to nine fluorines; said ($C_1$–$C_4$)alkyl or ($C_3$–$C_4$)cycloalkyl optionally mono-or di-substituted independently with hydroxy, ($C_1$–$C_4$)alkoxy, ($C_1$–$C_4$)alkylthio, ($C_1$–$C_4$)alkylsulfinyl, ($C_1$–$C_4$)alkylsulfonyl, ($C_1$–$C_4$)alkyl, mono-N- or di-N,N-($C_1$–$C_4$)alkylcarbamoyl or mono-N- or di-N,N-($C_1$–$C_4$)alkylaminosulfonyl; and said ($C_3$–$C_4$)cycloalkyl optionally having from one to seven fluorines;

wherein M in the compound of formula NHE is a partially saturated, fully saturated or fully unsaturated five to eight membered ring optionally having one to three heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

said M in the compound of formula NHE is optionally substituted, on one ring if the moiety is monocyclic, or one or both rings if the moiety is bicyclic, on carbon or nitrogen with up to three substituents independently selected from $R^6$, $R^7$ and $R^8$, wherein one of $R^6$, $R^7$ and $R^8$ is optionally a partially saturated, fully saturated, or fully unsaturated three to seven membered ring optionally having one to three heteroatoms selected independently from oxygen, sulfur and nitrogen optionally substituted with ($C_1$–$C_4$)alkyl and additionally $R^6$, $R^7$ and $R^8$ are optionally hydroxy, nitro, halo, ($C_1$–$C_4$) alkoxy, ($C_1$–$C_4$)alkoxycarbonyl, ($C_1$–$C_4$)alkyl, formyl, ($C_1$–$C_4$)alkanoyl, ($C_1$–$C_4$)alkanoyloxy, ($C_1$–$C_4$) alkanoylamino, ($C_1$–$C_4$)alkoxycarbonylamino, sulfonamido, ($C_1$–$C_4$)alkylsulfonamido, amino, mono-N- or di-N,N-($C_1$–$C_4$)alkylamino, carbamoyl, mono-N- or di-N,N-($C_1$–$C_4$)alkylcarbamoyl, cyano, thiol, ($C_1$–$C_4$)alkylthio, ($C_1$–$C_4$)alkylsulfinyl, ($C_1$–$C_4$) alkylsulfonyl, mono-N- or di-N,N-($C_1$–$C_4$) alkylaminosulfonyl, ($C_2$–$C_4$)alkenyl, ($C_2$–$C_4$)alkynyl or ($C_5$–$C_7$)cycloalkenyl, wherein said ($C_1$–$C_4$)alkoxy, ($C_1$–$C_4$)alkyl, ($C_1$–$C_7$) alkanoyl, ($C_1$–$C_4$)alkylthio, mono-N- or di-N,N-($C_1$–$C_4$)alkylamino or ($C_3$–$C_7$)cycloalkyl $R^6$, $R^7$ and $R^8$ substituents are optionally mono-substituted independently with hydroxy, ($C_1$–$C_4$)alkoxycarbonyl, ($C_3$–$C_7$)cycloalkyl, ($C_1$–$C_4$)alkanoyl, ($C_1$–$C_4$) alkanoylamino, ($C_1$–$C_4$)alkanoyloxy, ($C_1$–$C_4$) alkoxycarbonylamino, sulfonamido, ($C_1$–$C_4$) alkylsulfonamido, amino, mono-N- or di-N,N-($C_1$–$C_4$)

alkylamino, carbamoyl, mono-N- or di-N,N-$(C_1-C_4)$ alkylcarbamoyl, cyano, thiol, nitro, $(C_1-C_4)$alkylthio, $(C_1-C_4)$alkylsulfinyl, $(C_1-C_4)$alkylsulfonyl or mono-N- or di-N,N-$(C_1-C_4)$alkylaminosulfonyl or optionally substituted with one to nine fluorines.

Especially preferred NHE-1 inhibitors include [1-(8-bromoquinolin-5-yl)-5-cyclopropyl-1H-pyrazole-4-carbonyl]guanidine; [1-(6-chloroquinolin-5-yl)-5-cyclopropyl-1H-pyrazole-4-carbonyl]guanidine; [1-(indazol-7-yl)-5-cyclopropyl-1H-pyrazole-4-carbonyl] guanidine; [1-(benzimidazol-5-yl)-5-cyclopropyl-1H-pyrazole-4-carbonyl]guanidine; [1-(1-isoquinolyl)-5-cyclopropyl-1H-pyrazole-4-carbonyl]guanidine; [5-cyclopropyl-1-(4-quinolinyl)-1H-pyrazole-4-carbonyl] guanidine; [5-cyclopropyl-1-(quinolin-5-yl)-1H-pyrazole-4-carbonyl]guanidine; [5-cyclopropyl-1-(quinolin-8-yl)-1H-pyrazole-4-carbonyl]guanidine; [1-(indazol-6-yl)-5-ethyl-1H-pyrazole-4-carbonyl]guanidine; [1-(indazol-5-yl)-5-ethyl-1H-pyrazole-4-carbonyl]guanidine; [1-(benzimidazol-5-yl)-5-ethyl-1H-pyrazole-4-carbonyl]guanidine; [1-(1-methylbenzimidazol-6-yl)-5-ethyl-1H-pyrazole-4-carbonyl] guanidine; 1-(5-quinolinyl)-5-n-propyl-1H-pyrazole-4-carbonyl]guanidine; [1-(5-quinolinyl)-5-isopropyl-1H-pyrazole-4-carbonyl]guanidine; [5-ethyl-1-(6-quinolinyl)-1H-pyrazole-4-carbonyl]guanidine; [1-(2-methylbenzimidazol-5-yl)-5-ethyl-1H-pyrazole-4-carbonyl] guanidine; [1-(1,4-benzodioxan-6-yl)-5-ethyl-1H-pyrazole-4-carbonyl]guanidine; [1-(benzotriazol-5-yl)-5-ethyl-1H-pyrazole-4-carbonyl]guanidine; [1-(3-chloroindazol-5-yl)-5-ethyl-1H-pyrazole-4-carbonyl]guanidine; [1-(5-quinolinyl)-5-butyl-1H-pyrazole-4-carbonyl]guanidine; [5-propyl-1-(6-quinolinyl)-1H-pyrazole-4-carbonyl] guanidine; [5-isopropyl-1-(6-quinolinyl)-1H-pyrazole-4-carbonyl]guanidine; [1-(2-chloro-4-methylsulfonylphenyl)-5-cyclopropyl-1H-pyrazole-4-carbonyl]guanidine; [1-(2-chlorophenyl)-5-cyclopropyl-1H-pyrazole-4-carbonyl] guanidine; [1-(2-trifluoromethyl-4-fluorophenyl)-5-cyclopropyl-1H-pyrazole-4-carbonyl]guanidine; [1-(2-bromophenyl)-5-cyclopropyl-1H-pyrazole-4-carbonyl] guanidine; [1-(2-fluorophenyl)-5-cyclopropyl-1H-pyrazole-4-carbonyl]guanidine; [1-(2-chloro-5-methoxyphenyl)-5-cyclopropyl-1H-pyrazole-4-carbonyl]guanidine; [1-(2-chloro-4-methylaminosulfonylphenyl)-5-cyclopropyl-1H-pyrazole-4-carbonyl]guanidine; [1-(2,5-dichlorophenyl)-5-cyclopropyl-1H-pyrazole-4-carbonyl]guanidine; [1-(2,3-dichlorophenyl)-5-cyclopropyl-1H-pyrazole-4-carbonyl] guanidine; [1-(2-chloro-5-aminocarbonylphenyl)-5-cyclopropyl-1H-pyrazole-4-carbonyl]guanidine; [1-(2-chloro-5-aminosulfonylphenyl)-5-cyclopropyl-1H-pyrazole-4-carbonyl]guanidine; [1-(2-fluoro-6-trifluoromethylphenyl)-5-cyclopropyl-1H-pyrazole-4-carbonyl]guanidine; [1-(2-chloro-5-methylsulfonylphenyl)-5-cyclopropyl-1H-pyrazole-4-carbonyl]guanidine; [1-(2-chloro-5-dimethylaminosulfonylphenyl)-5-cyclopropyl-1H-pyrazole-4-carbonyl]guanidine; [1-(2-trifluoromethyl-4-chlorophenyl)-5-cyclopropyl-1H-pyrazole-4-carbonyl] guanidine; [1-(2-chlorophenyl)-5-methyl-1H-pyrazole-4-carbonyl]guanidine; [5-methyl-1-(2-trifluoromethylphenyl)-1H-pyrazole-4-carbonyl]guanidine; [5-ethyl-1-phenyl-1H-pyrazole-4-carbonyl]guanidine; [5-cyclopropyl-1-(2-trifluoromethylphenyl)-1H-pyrazole-4-carbonyl]guanidine; [5-cyclopropyl-1-phenyl-1H-pyrazole-4-carbonyl]guanidine; [5-cyclopropyl-1-(2,6-dichlorophenyl)-1H-pyrazole-4-carbonyl]guanidine or or a pharmaceutically acceptable salt thereof.

The preferred and especially preferred NHE-1 inhibitors disclosed in the above two paragraphs can be prepared according to methods set forth in International Patent Application No. PCT/IB99/00206 or as set forth below, where the variables in the following schemes and description refer only to the NHE-1 compounds.

SCHEME I

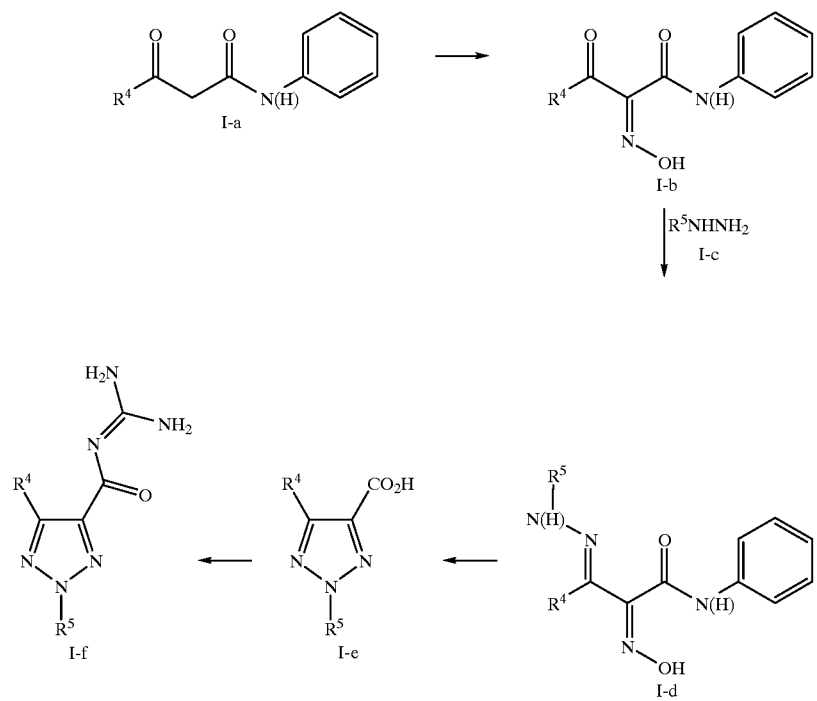

SCHEME II
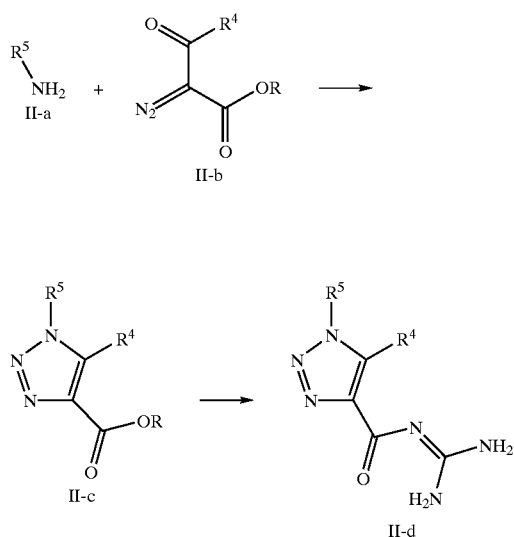
SCHEME III
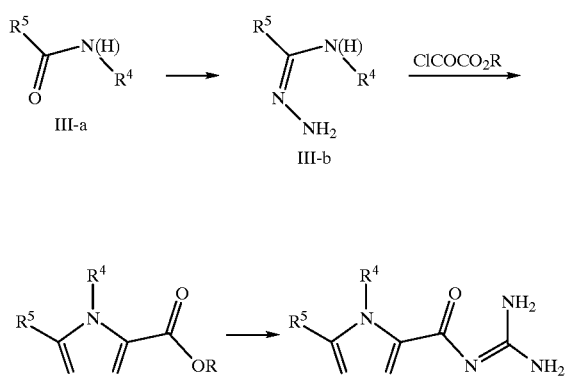
SCHEME IV
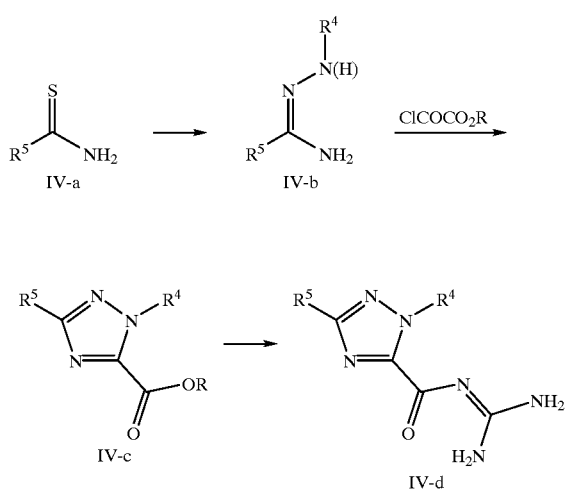
SCHEME V
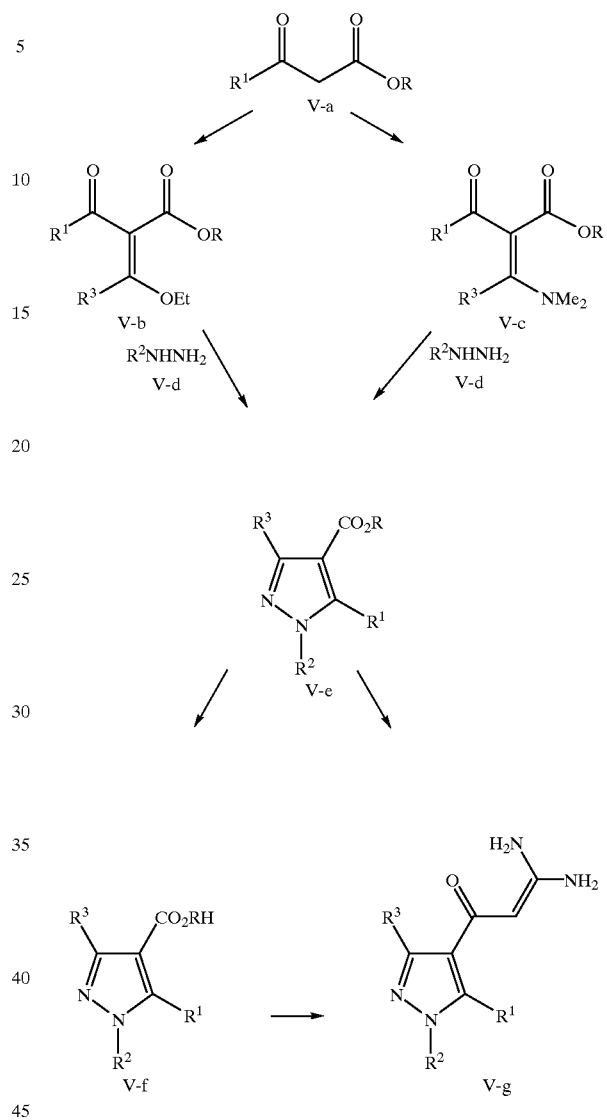
SCHEME VI
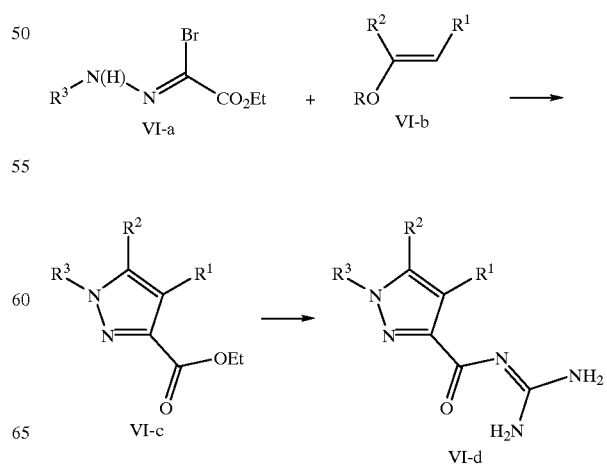

SCHEME VII

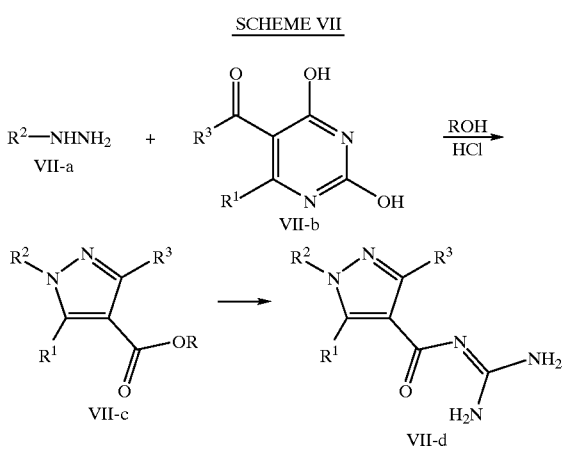

SCHEME VIII

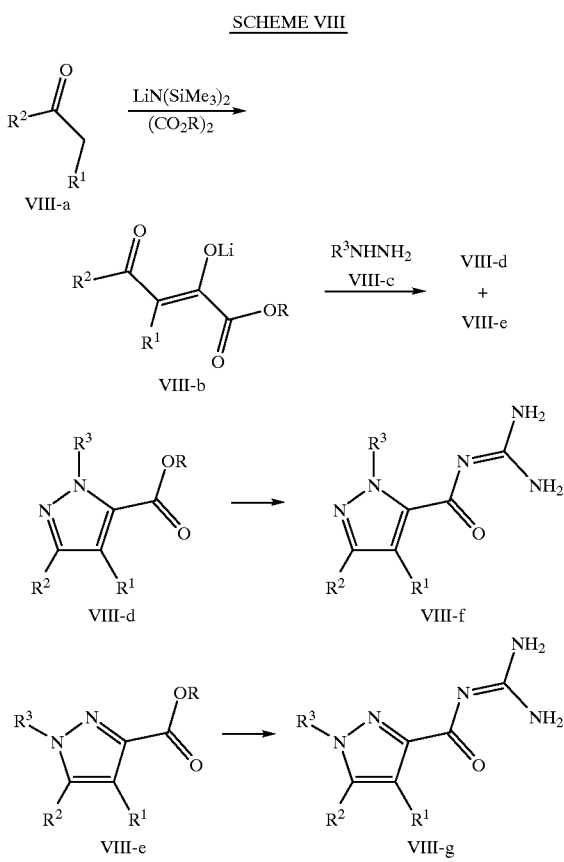

According to Scheme I, the Formula I-a compound, wherein $R^4$ is as described above for the compound of formula NHE, is dissolved or suspended in an aqueous alkali metal hydroxide solution (e.g. 1 N sodium hydroxide) along with sodium nitrite and the mixture is added to an aqueous acidic solution (e.g. 10% v/v sulfuric acid) at a pH of about 0 at a temperature of about 0° C. to about 5° C. for about 30 min to about 1 hour. The resulting mixture is filtered to yield the Formula I-b oxime. Alternatively, the Formula I-a compound is dissolved in 1:1 acetic acid/propionic acid and solid sodium nitrite is added at about 0° C. The reaction mixture is stirred at about 0° C. for about 2 hours, then poured into ice water and the Formula I-b oxime is obtained by filtration.

The Formula I-b compound is reacted with a Formula I-c compound, wherein $R^5$ is as described above for the compound of formula NHE in a protic solvent such as ethanol at a temperature of about 50° C. to about 110° C. for about 10 min to about 1 hour to form the Formula I-d hydrazone.

The Formula I-d hydrazone is cyclized and hydrolyzed to the Formula I-e triazole in an alcoholic solvent such as 2-ethoxyethanol under basic conditions (e.g., potassium hydroxide) at a temperature of about 100° C. to about 175° C. for about ½ hour to about 2 hours followed by acidification to yield the Formula I-e triazole acid.

The Formula I-e acid is coupled with guanidine in the presence of a suitable coupling agent. A suitable coupling agent is one which transforms a carboxylic acid into a reactive species which forms an amide linkage on reaction with an amine.

The coupling agent may be a reagent which effects this condensation in a one pot process when mixed together with the carboxylic acid and guanidine. Exemplary coupling reagents are 1-(3-dimethylaminopropyl)-3-ethylcarbodiimide hydrochloride-hydroxybenzotriazole (EDC/HBT), dicyclohexylcarbodiimide/hydroxybenzotriazole(HBT), 2-ethoxy-1-ethoxycarbonyl-1,2-dihydroquinoline (EEDQ), and diethylphosphorylcyanide. The coupling is performed in an inert solvent, preferably an aprotic solvent at a temperature of about −20° C. to about 50° C. for about 1 to about 48 hours, in the presence of excess guanidine as base. Exemplary solvents include acetonitrile, dichloromethane, dimethylformamide and chloroform or mixtures thereof.

The coupling agent may also be that agent which converts the carboxylic acid to an activated intermediate which is isolated and/or formed in a first step and allowed to react with guanidine in a second step. Examples of such coupling agents and activated intermediates are thionyl chloride or oxalyl chloride to form the acid chloride, cyanuric fluoride to form an acid fluoride or an alkyl chloroformate such as isobutyl or isopropenyl chloroformate or propanephosphonic anhydride (propanephosphonic acid anhydride, PPA) (with a tertiary amine base) to form a mixed anhydride of the carboxylic acid, or carbonyldiimidazole to form an acylimidazole. If the coupling agent is oxalyl chloride, it is advantageous to employ a small amount of dimethylformamide as cosolvent with another solvent (such as dichloromethane) to catalyze the formation of the acid chloride. This activated acid derivative may be coupled by mixing with excess guanidine in an appropriate solvent together with an appropriate base. Appropriate solvent/base combinations are for example, dichloromethane, dimethylformamide or acetonitrile or mixtures thereof in the presence of excess guanidine as base. Other appropriate solvent/base combinations include water or a $(C_1$–$C_5)$alcohol or a mixture thereof together with a cosolvent such as dichloromethane, tetrahydrofuran or dioxane and a base such as sodium, potassium or lithium hydroxide in sufficient quantity to consume the acid liberated in the reaction. Use of these coupling agents and appropriate selection of solvents and temperatures are known to those skilled in the art or can be readily determined from the literature. These and other exemplary conditions useful for coupling carboxylic acids are described in Houben-Weyl, Vol XV, part 11, E. Wunsch, Ed., G. Theime Verlag, 1974, Stuttgart; M. Bodansky, Principles of Peptide Synthesis, Springer-Verlag, Berlin 1984; and The Peptides, Analysis, Synthesis and Biology (ed. E. Gross and J. Meienhofer), vols 1–5 (Academic Press, NY 1979–1983).

According to Scheme II, the Formula II-a primary amine wherein $R^5$ is as described above for the compound of formula NHE is reacted with a Formula II-b α-diazo-β-keto-ester wherein $R^4$ is as described above for the compound of formula NHE, and R is lower alkyl, in the presence of titanium tetrachloride analogously to the method described in Eguchi S. et al. *Synthesis* 1993, 793 to form the Formula II-c triazole carboxylic acid ester. The Formula II-c ester is converted directly to the acylguanidine II-d by reaction with guanidine in an alcoholic solvent at a temperature of about 60 to about 110° C., preferably refluxing methanol, for a period of 8 to 20 hours.

According to Scheme III, the Formula III-a compound wherein $R^4$ and $R^5$ are as described above for the compound of formula NHE is treated with Lawesson's reagent (i.e., 2,4-bis(4-methoxyphenyl)-1,3-dithia-2,4-diphosphetane-2, 4-disulfide) in an aprotic solvent such as dimethoxyethane at a temperature of about 20° C. to about 120° C. for about one to eight hours. The resulting thioamide is treated with an alkylating agent such as methyl iodide in a polar, inert solvent such as acetone, conveniently at ambient temperature for about eight hours to about forty-eight hours. The resulting compound is reacted with anhydrous hydrazine in an alcoholic solvent at a temperature of about 0° C. to about 25° C. for about one to eight hours to provide the Formula III-b compound (analogously as described in Doyle and Kurzer, *Synthesis* 1974, 583).

The Formula III-b compound is treated with a monoalkyloxalyl chloride in an aprotic solvent at a temperature of about 25° C. to about 50° C. for about one to eight hours to provide the Formula III-c carboxylic ester compound wherein R is lower alkyl. The Formula III-c ester is directly coupled with guanidine in an alcoholic solvent at a temperature of about 60° C. to about 110° C., preferably refluxing methanol, for a period of eight to twenty hours, to prepare the Formula III-d triazole carbonyl guanidines.

According to Scheme IV the Formula IV-a compound wherein $R^5$ is as described above for the compound of formula NHE is treated with methyl iodide in an inert solvent, conveniently at ambient temperature for about four to twenty-four hours. The resulting compound is reacted with anhydrous $R^4$-hydrazine (wherein $R^4$ is as described above for the compound of formula NHE) in an alcoholic solvent at a temperature of about 0° C. to about 25° C. for about one to eight hours to provide the Formula IV-b amidrazone compound (analogously as described in Doyle and Kurzer, *Synthesis* 1974, 583).

The Formula IV-b compound is treated with a monoalkyloxalyl chloride in an aprotic solvent at a temperature of about 25° C. to about 50° C. for about one to eight hours to provide the Formula IV-c carboxylic ester compound wherein R is lower alkyl. The Formula IV-c ester is directly coupled with guanidine in an alcoholic solvent at a temperature of about 60° C. to about 110° C., preferably refluxing methanol, for a period of eight to twenty hours to prepare the Formula IV-d triazole carbonyl guanidines.

According to Scheme V the Formula V-a compound wherein $R^1$ is as described above for the compound of formula NHE is combined with excess $(CH_3O)_2C(R^3)N(CH_3)_2$ (N,N-dimethyl amide dimethyl acetal) wherein $R^3$ is as described above for the compound of formula NHE, optionally in the presence of an acid catalyst such as p-toluenesulfonic acid at a temperature of about 90° C. to about 110° C. for about one to about two hours to prepare the Formula V-c compound above.

The Formula V-c compound is cyclized with a Formula V-d compound, wherein R is as described above for the compound of formula NHE, in an inert solvent such as ethanol at a temperature of about 20° C. to about 30° C. for about 5 minutes to about one hour followed by heating to a temperature of about 70° C. to about 110° C. for about two hours to about four hours to form the Formula V-f pyrazole.

Alternatively, according to Scheme V the Formula V-a compound, wherein $R^1$ is as described above for the compound of formula NHE, is combined with a triethylorthoester (i.e., $R^3C(OEt)_3$ wherein $R^3$ is as described above for the compound of formula NHE) and acetic anhydride at a temperature of about 120° C. to about 150° C. for about two to about five hours to prepare the Formula V-b compound.

The Formula V-b compound is cyclized with a Formula V-d compound, wherein $R^2$ is as described above for the compound of formula NHE, to form the Formula V-c pyrazole.

The Formula V-c pyrazole is hydrolyzed with a base such as sodium hydroxide or lithium hydroxide in a solvent such as water and/or methanol and/or THF conveniently at ambient temperature or at elevated temperature (e.g., reflux) for about one hour to about five hours to prepare the Formula V-f acid.

The Formula V-f acid is coupled with guanidine in the presence of a suitable coupling agent as described for the above coupling of the Formula I-e acid and guanidine. In one embodiment, the Formula V-f acid is activated with thionyl chloride at a temperature of about 60° C. to about 90° C. for about fifteen minutes to about two hours. The resulting activated acid chloride is combined with guanidine hydrochloride and an inorganic base (e.g., sodium hydroxide) in anhydrous tetrahydrofuran and optionally methanol and/or water. The solution is heated, conveniently at reflux, for about one hour to about eight hours to prepare the Formula V-g compound.

Alternatively according to Scheme V the Formula V-e compound can be directly converted to the Formula V-g compound by several methods. For example, the Formula V-e compound can be heated in the presence of excess guanidine, in a polar protic solvent for example, methanol or isopropanol at a suitable temperature conveniently, at reflux for about one to about seventy-two hours. This transformation may also be performed by repeatedly removing the solvent, for example removing ethanol or toluene about four times, from a mixture of the Formula V-e compound and excess guanidine at a pressure of about one to about 100 mmHg and at a temperature of about 25° C. to about 95° C. This reaction may also be performed in the absence of solvent by heating the mixture of the Formula V-e compound and excess guanidine at a temperature of about 100° C. to about 180° C., optionally at about a pressure of about 1 to about 100 mmHg for about five minutes to about eight hours.

According to Scheme VI, the Formula VI-a compound, wherein $R^3$ is as described above for the compound of formula NHE, is reacted with the Formula VI-b compound, wherein $R^1$ and $R^2$ are as described above for the compound of formula NHE, in an aprotic solvent at a temperature of about 0° C. to about 25° C. for about two hours to about twenty-four hours in the presence of an appropriate amine base, such as triethylamine, to form the Formula VI-c compound.

The resulting Formula VI-c compound is hydrolyzed and coupled with guanidine using one of the methods described in earlier Schemes, such as the method employing carbonyldiimidazole, to form the Formula VI-d compound.

According to Scheme VII, the Formula VII-a hydrazine, wherein $R^2$ is as described above for the compound of formula NHE, is reacted with the appropriate Formula VII-b compound to form the Formula VII-c pyrazole ester wherein R is lower alkyl according to the method of Bajnati, A. and Hubert-Habart, M. *Bull. Soc. Chim. France* 1988, 540. The resulting pyrazole ester is converted to the Formula VII-d acyl guanidine using the hydrolysis and coupling methods described above.

According to Scheme VIII, the Formula VIII-a compound wherein $R^2$ and $R^1$ are as described above for the compound of formula NHE is transformed to the Formula VIII-b lithium salt where R is lower alkyl according to the method described in *J. Het. Chem.* 1989, 26,1389. The Formula VIII-b lithium salt is combined with the Formula VIII-c hydrazine, wherein $R^3$ is as described above for the compound of formula NHE, in an inert solvent such as ethanol, in the presence of a mineral acid, at a temperature of about 20° C. to about 30° C. for about five minutes to about one hour followed by heating to a temperature of about 70° C. to about 110° C. for two hours to about four hours to form both the Formula VIII-d and VIII-e pyrazoles. The Formula VIII-d and VIII-e pyrazoles are converted to the Formula VIII-f and VIII-g acyl guanidines respectively using the hydrolysis and coupling methods described above. Some of the methods useful for the preparation of the compounds described herein may require protection of remote functionality (e.g., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis,* John Wiley & Sons, New York, 1991.

The compounds of formula I of the present invention, when used in combination with NHE-1 inhibitors, inhibit the sodium/proton ($Na^+/H^+$) exchange transport system and hence are useful as a therapeutic or prophylactic agent for diseases caused or aggravated by the acceleration of the sodium/proton ($Na^+/H^+$) exchange transport system, for example, cardiovascular diseases (e.g., arteriosclerosis, hypertension, arrhythmia (e.g. ischemic arrhythmia, arrhythmia due to myocardial infarction, myocardial stunning, myocardial dysfunction, arrhythmia after PTCA or after thrombolysis, etc.), angina pectoris, cardiac hypertrophy, myocardial infarction, heart failure (e.g. congestive heart failure, acute heart failure, cardiac hypertrophy, etc.), restenosis after PTCA, PTCI, shock (e.g. hemorrhagic shock, endotoxin shock, etc.)], renal diseases (e.g. diabetes mellitus, diabetic nephropathy, ischemic acute renal failure, etc.) organ disorders associated with ischemia or ischemic reperfusion [e.g. heart muscle ischemic reperfusion associated disorders, acute renal failure, or disorders induced by surgical treatment such as coronary artery bypass grafting (CABG) surgeries, vascular surgeries, organ transplantation, non-cardiac surgeries or percutaneous transluminal coronary angioplasty (PTCA)], cerebrovascular diseases (e.g. ischemic stroke, hemorrhagic stroke, etc.), cerebro ischemic disorders (e.g. disorders associated with cerebral infarction, disorders caused after cerebral apoplexy as sequelae, or cerebral edema.

Preferably, the compounds of formula I of this invention can be used in combination with NHE-1 inhibitors as agents for myocardial protection before, during, or after coronary artery bypass grafting (CABG) surgeries, vascular surgeries, percutaneous transluminal coronary angioplasty (PTCA), organ transplantation, or non-cardiac surgeries.

Preferably, the compounds of formula I of this invention can be used in combination with NHE-1 inhibitors as agents for myocardial protection in patients presenting with ongoing cardiac (acute coronary syndromes, e.g. myocardial infarction or unstable angina) or cerebral ischemic events (e.g. stroke).

Preferably, the compounds of formula I of this invention can be used in combination with NHE-1 inhibitors as agents for chronic myocardial protection in patients with diagnosed coronary heart disease (e.g. previous myocardial infarction or unstable angina) or patients who are at high risk for myocardial infarction (age greater than 65 and two or more risk factors for coronary heart disease).

In addition, a combination of the compounds of formula I of this invention with NHE-1 inhibitors has a strong inhibitory effect on the proliferation of cells, for example the proliferation of fibroblast cells and the proliferation of the smooth muscle cells of the blood vessels. For this reason, the combination of the compounds of formula I of this invention with NHE-1 inhibitors of this invention is a valuable therapeutic agent for use in diseases in which cell proliferation represents a primary or secondary cause and may, therefore, be used as antiatherosclerotic agents, and as agents against diabetic late complications, cancerous diseases, fibrotic diseases such as pulmonary fibrosis, hepatic fibrosis or renal fibrosis, glomerular nephrosclerosis, organ hypertrophies or hyperplasias, in particular hyperplasia or hypertrophy of the prostate, pulmonary fibrosis, diabetic complications or recurrent stricture after PTCA, or diseases caused by endothelial cell injury.

The utility of the combination of compounds of the present invention with NHE-1 inhibitors as medical agents in the treatment of diseases, such as are detailed herein in mammals (e.g. humans) for example, myocardial protection during surgery or mycardial protection in patients presenting with ongoing cardiac or cerebral ischemic events or chronic cardioprotection in patients with diagnosed coronary heart disease, or at risk for coronary heart disease, cardiac dysfunction or myocardial stunning is demonstrated by the activity of said combination in conventional preclinical cardioprotection assays [see the in vivo assay in Klein, H. et al., Circulation 92:912–917 (1995); the isolated heart assay in Scholz, W. et al., Cardiovascular Research 29:260–268 (1995); the antiarrhythmic assay in Yasutake M. et al., Am. J. Physiol., 36:H2430–H2440 (1994); the NMR assay in Kolke et al., J. Thorac. Cardiovasc. Surg. 112: 765–775 (1996)] and the additional in vitro and in vivo assays described below. Such assays also provide a means whereby the activities of the compounds of formula I of this invention can be compared with the activities of other known compounds. The results of these comparisons are useful for determining dosage levels in mammals, including humans, for the treatment of such diseases.

Measurement of Human NHE-1 Inhibitory Activity

Methodologies for measurement of human NHE-1 activity and inhibitor potency are based on those published by Watson et al., Am. J. Physiol., 24:G229–G238, 1991), where NHE-mediated recovery of intracellular pH is measured following intracellular acidification. Thus, fibroblasts stably expressing human NHE-1 (Counillon, L. et al., Mol. Pharmacol., 44:1041–1045 (1993) are plated onto collagen coated 96 well plates (50,000/well) and grown to confluence in growth media (DMEM high glucose, 10% fetal bovine serum, 50 u/ml penicillin and streptomycin). Confluent plates are incubated for 30 minutes at 37° C. with the pH sensitive fluorescent probe BCECF (5 $\mu$M; Molecular Probes, Eugene, Oreg.). BCECF loaded cells are incubated for 30 minutes at 37° C. in acid loading media (70 mM choline chloride, 50 mM $NHCl_4$, 5 mM KCl, 1 mM $MgCl_2$, 1.8 mM $CaCl_2$, 5 mM glucose, 10 mM HEPES, pH 7.5), and then placed in a Fluorescent Imaging Plate Reader (Molecular Devices, CA). BCECF fluorescence is monitored using excitation and emission wavelengths of 485 nM and 525 nM, respectively. Intracellular acidification is initiated via rapid replacement of acid loading media with recovery media (120 mM NaCl, 5 mM KCl, 1 mM $MgCl_2$, 1.8 mM $CaCl_2$, 5 mM glucose, 10 mM HEPES, pH 7.5)±test combination, and NHE-mediated recovery of intracellular pH is monitored as the subsequent time-dependent increase BCECF fluorescence. The potency of the combinations of the compounds of formula I of this invention with NHE-1 inhibitors is calculated as the concentration that reduces recovery of intracellular pH by 50% ($IC_{50}$). Under these conditions reference NHE inhibitors amiloride and HOE-642 had $IC_{50}$ values for human NHE-1 of 50 $\mu$M and 0.5 $\mu$M, respectively.

As background information, it is noted that brief periods of myocardial ischemia followed by coronary artery reperfusion protects the heart from subsequent severe myocardial ischemia (Murry et al., Circulation 74:1124–1136,1986).

The therapeutic effects of the combination of the compounds of formula I of this invention with NHE-1 inhibitors in preventing heart tissue damage resulting from an ischemic insult can be demonstrated in vitro along lines presented in Liu et al. (Cardiovasc. Res., 28:1057–1061,1994), as described specifically herein. Cardioprotection, as indicated by a reduction in infarcted myocardium, can be induced pharmacologically using adenosine receptor agonists in isolated, retrogradely perfused rabbit hearts as an in vitro model of myocardial ischemic preconditioning (Liu et al., Cardiovasc. Res., 28:1057–1061,1994). The in vitro test described below demonstrates that a test compound or, in this case a test combination (i.e., a combination of a compound of formula I with an NHE-1 antagonist) can also pharmacologically induce cardioprotection, i.e., reduced myocardial infarct size, when administered to a rabbit isolated heart. The effects of the test combination are compared to ischemic preconditioning and the A1/A3 adenosine agonist, APNEA ($N^6$-[2-(4-aminophenyl)ethyl]adenosine), that has been shown to pharmacologically induce cardioprotection in the rabbit isolated heart (Liu et al., Cardiovasc. Res., 28:1057–1061,1994). The exact methodology is described below.

The protocol used for these experiments closely follows that described by Liu et al., Cardiovasc. Res., 28:1057–1061,1994. Male New Zealand White rabbits (3–4 kg) are anesthetized with sodium pentobarbital (30 mg/kg, i.v.). After deep anesthesia is achieved (determined by the absence of an ocular blink reflex) the animal is intubated and ventilated with 100% $O_2$ using a positive pressure ventilator. A left thoracotomy is performed, the heart exposed, and a snare (2-0 silk) is placed loosely around a prominent branch of the left coronary artery, approximately ⅔ of the distance towards the apex of the heart. The heart is removed from the chest and rapidly (<30 sec) mounted on a Langendorff apparatus. The heart is retrogradely perfused in a non-recirculating manner with a modified Krebs solution (NaCl 118.5 mM, KCl 4.7 mM, Mg $SO_4$ 1.2 mM, $KH_2PO_4$ 1.2 mM, $NaHCO_3$ 24.8 mM, $CaCl_2$ 2.5 mM, and glucose 10 mM), at a constant pressure of 80 mmHg and a temperature of 37° C. Perfusate pH is maintained at 7.4–7.5 by bubbling with 95% $O_2$/5% $CO_2$. Heart temperature is tightly controlled by using heated reservoirs for the physiological solution and water jacketing around both the perfusion tubing and the isolated heart. Heart rate and left ventricular pressures are determined via a latex balloon which is inserted in the left ventricle and connected by stainless steel tubing to a pressure transducer. The intraventricular balloon is inflated to provide a systolic pressure of 80–100 mmHg, and a diastolic pressure ≦10 mmHg. Total coronary flow is also continuously monitored using an in-line flow probe and normalized for heart weight.

The heart is allowed to equilibrate for 30 minutes, over which time the heart must show stable left ventricular pressures within the parameters outlined above. If the heart rate falls below 180 bpm at any time prior to the 30 minutes period of regional ischemia, the heart is paced at about 200 bpm for the remainder of the experiment. Ischemic preconditioning is induced by total cessation of cardiac perfusion (global ischemia) for 5 minutes, followed by reperfusion for 10 minutes. The regional ischemia is provided by tightening the snare around the coronary artery branch. Following the 30 minutes regional ischemia, the snare is released and the heart reperfused for an additional 120 minutes.

Pharmacological cardioprotection is induced by infusing the test combination, i.e., a combination of a compound of formula I with an NHE-1 inhibitor, at predetermined concentrations, starting 30 minutes prior to the 30 minutes regional ischemia, and continuing until the end of the 120 minutes reperfusion period. Hearts which receive the test combination do not undergo the period of ischemic preconditioning. The reference compound, APNEA (500 nM) is perfused through hearts (which do not receive the test compound) for a 5 minutes period which ends 10 minutes before the 30 minutes regional ischemia.

At the end of the 120 minutes reperfusion period, the coronary artery snare is tightened, and a 0.5% suspension of fluorescent zinc cadmium sulfate particles (1–10 $\mu$M) Duke Scientific Corp. (Palo Alto, Calif.) is perfused through the heart; this stains all of the myocardium, except that area-at-risk for infarct development (area-at-risk). The heart is removed from the Langendorff apparatus, blotted dry, wrapped in aluminum foil and stored overnight at −200C. The next day, the heart is sliced into 2 mm transverse sections from the apex to the top of the ventricles. The slices are stained with 1% triphenyl tetrazolium chloride (TTC) in phosphate-buffered saline for 20 minutes at 37° C. Since TTC reacts with living tissue (containing NAD-dependent dehydrogenases), this stain differentiates between living (red stained) tissue, and dead tissue (unstained infarcted tissue). The infarcted area (no stain) and the area-at-risk (no fluorescent particles) are calculated for each slice of left ventricle using a precalibrated image analyzer. To normalize the ischemic injury for differences in the area-at-risk between hearts, the data is expressed as the ratio of infarct area vs. area-at-risk (%IA/AAR). All data are expressed as mean±SE and compared statistically using a Mann-Whitney non-parametric test with a Bonferroni correction for multiple comparisons. Significance is considered as $p<0.05$.

The results from the above in vitro test demonstrate that a combination of a compound of this invention with an NHE-1 inhibitor induce significant cardioprotection relative to the control group.

The therapeutic effects of a combination of a compound of formula I of this invention with an NHE-1 inhibitor in preventing heart tissue damage otherwise resulting from an ischemic insult can also be demonstrated in vivo along lines presented in Liu et al. (Circulation, Vol. 84:350–356, 1991) as described specifically herein. The in vivo assay tests the cardioprotection of the test combination, i.e., a compound of formula I together with an NHE-1 inhibitor, relative to the control group which receives saline vehicle. Cardioprotection, as indicated by a reduction in infarcted myocardium, can be induced pharmacologically using intravenously administered adenosine receptor agonists in intact, anesthetized rabbits studied as an in situ model of myocardial ischemic preconditioning (Liu et al., Circulation 84:350–356, 1991). The in vivo assay tests whether the instant combination of a compound of formula I with an NHE-1 inhibitor can pharmacologically induce cardioprotection, i.e., reduced myocardial infarct size, when parenterally administered to intact, anesthetized rabbits. The effects of the combination of a compound of formula I of this invention with an NHE-11 inhibitor can be compared to ischemic preconditioning using the A1 adenosine agonist, $N^6$-1-(phenyl-2R-isopropyl) adenosine (PIA) that has been shown to pharmacologically induce cardioprotection in intact anesthetized rabbits studied in situ (Liu et al., Circulation 84:350–356, 1991). The methodology is described below.

Surgery:

New Zealand White male rabbits (3–4 kg) are anesthetized with sodium pentobarbital (30 mg/kg, i.v.). A tracheotomy is performed via a ventral midline cervical incision and the rabbits are ventilated with 100% oxygen using a positive pressure ventilator. Catheters are placed in the left jugular vein for drug administration and in the left carotid artery for blood pressure measurements. The hearts are then exposed through a left thoracotomy and a snare (00 silk) placed around a prominent branch of the left coronary artery. Ischemia is induced by pulling the snare tight and clamping it in place. Releasing the snare allows the affected area to reperfuse. Myocardial ischemia is evidenced by regional cyanosis; reperfusion is evidenced by reactive hyperemia.

Protocol:

Once arterial pressure and heart rate have been stable for at least 30 minutes the test is started. Ischemic preconditioning is induced by occluding the coronary artery for 5 minutes followed by a 10 minutes reperfusion. Pharmacological preconditioning is induced by infusing the test combination, i.e., a combination of a compound of formula I of this invention with an NHE-1 inhibitor, over, for example, 5 minutes and allowing 10 minutes before further intervention or by infusing the adenosine agonist, PIA (0.25 mg/kg). Following ischemic preconditioning, pharmacological preconditioning or no conditioning (unconditioned, vehicle control) the artery is occluded for 30 minutes and then reperfused for two hours to induce myocardial infarction. The test combination and PIA are dissolved in saline or other suitable vehicle and delivered at 1 to 5 mg/kg, respectively.

Staining (Liu et al., *Circulation* 84:350–356, 1991): At the end of the 2 hour reperfusion period, the hearts are quickly removed, hung on a Langendorff apparatus, and flushed for 1 minute with normal saline heated to body temperature (38° C.). The silk suture used as the snare is then tied tightly to reocclude the artery and a 0.5% suspension of fluorescent zinc cadmium sulphate particles (1–10 μm) Duke Scientific Corp. (Palo Alto, Calif.) is infused with the perfusate to stain all of the myocardium except the area at risk (nonfluorescent ventricle). The hearts are then quickly frozen and stored overnight at −20° C. On the following day, the hearts are cut into 2 mm slices and stained with 1% triphenyl tetrazolium chloride (TTC). Since TTC reacts with living tissue, this stain differentiates between living (red stained) tissue, and dead tissue (unstained infarcted tissue). The infarcted area (no stain) and the area at risk (no fluorescent particles) are calculated for each slice of left ventricle using a pre-calibrated image analyzer. To normalize the ischemic injury for differences in the area at risk between hearts, the data is expressed as the ratio of infarct area vs. area at risk (%IA/AAR). All data are expressed as Mean±SEM and compared statistically using single factor ANOVA or Mann Whitney non parametric test. Significance is considered as p<0.05.

Any glycogen phosphorylase inhibitor (GPI) may be used as the second pharmacetical agent in the pharmaceutical compositions, methods and kits of this invention. The term glycogen phosphorylase inhibitor refers to any substance or agent or any combination of substances and/or agents which reduces, retards, or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis). Such actions are readily determined by those skilled in the art according to standard assays as described in the following published PCT applications: PCT application publication WO 96/39384 and PCT application publication WO96/39385. A variety of these compounds are included in those applications. However, other glycogen phosphorylase inhibitors will be known to those skilled in the art.

Any sorbitol dehydrogenase inhibitor (SDI) may be used as the second pharmaceutical agent in the pharmaceutical compositions, methods and kits of this invention. The term sorbitol dehydrogenase inhibitor refers to any substance or agent or any combination of substances and/or agents which reduces, retards, or eliminates the enzymatic action of sorbitol dehydrogenase. The currently known enzymatic action of sorbitol dehydrogenase is the catalysis of the oxidation of sorbitol to fructose.

Preferred SDI compounds include compounds of the formula

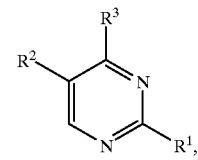

SDI a prodrug thereof or a pharmaceutically acceptable salt of said compound or said prodrug, wherein:

$R^1$ in the compound of formula SDI is formyl, acetyl, propionyl, carbamoyl or —C(OH)$R^4R^5$;

$R^4$ and $R^5$ in the compound of formula SDI are each independently hydrogen, methyl, ethyl or hydroxy-($C_1$–$C_3$)alkyl;

$R^2$ in the compound of formula SDI is hydrogen, ($C_1$–$C_4$) alkyl or ($C_1$–$C_4$)alkoxy;

$R^3$ in the compound of formula SDI is a radical of the formula

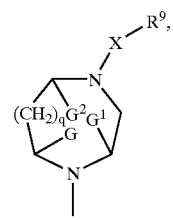 R³ᵃ
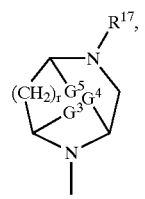 R³ᵇ
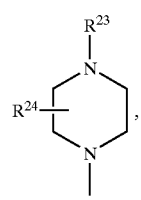 R³ᶜ
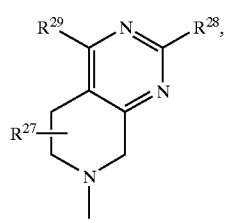 R³ᵈ
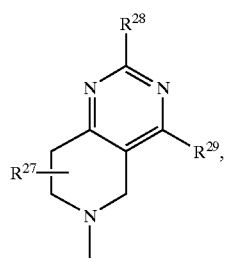 R³ᵉ
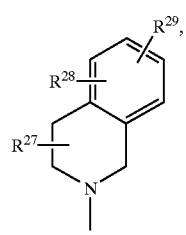 R³ᶠ
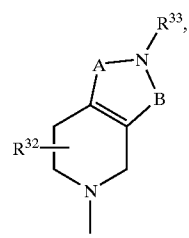 R³ᵍ
-continued
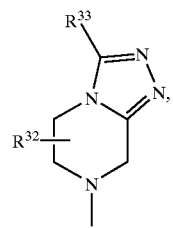 R³ʰ
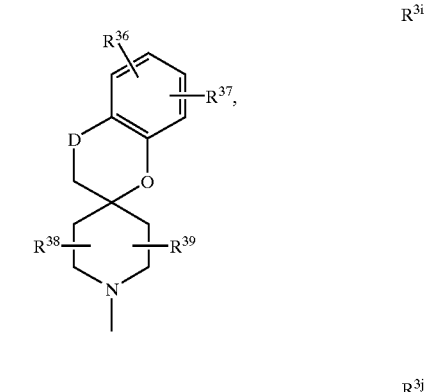 R³ⁱ
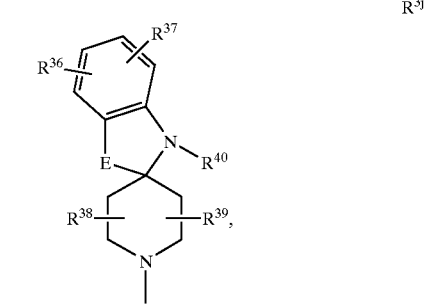 R³ʲ
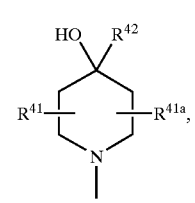 R³ᵏ
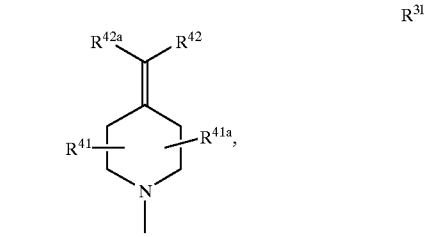 R³ˡ
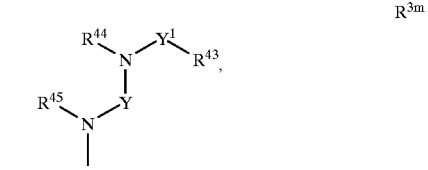 R³ᵐ

29

-continued

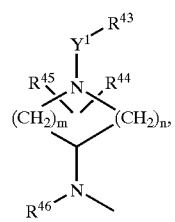
R³ⁿ

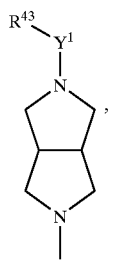
R³ᵒ

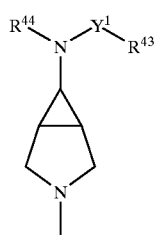
R³ᵖ or

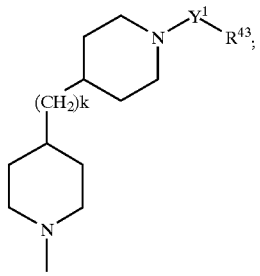
R³q;

wherein said radical of formula R$^{3a}$ is additionally substituted on the ring by R$^6$, R$^7$ and R$^8$;
said radical of formula R$^{3b}$ is additionally substituted on the ring by R$^{18}$, R$^{19}$ and R$^{20}$;
G, G$^1$ and G$^2$ are taken separately and are each hydrogen and R$^6$ is hydrogen, (C$_1$–C$_4$)alkyl, (C$_1$–C$_4$)alkoxycarbonyl, (C$_1$–C$_4$)alkoxy-(C$_1$–C$_4$)alkyl, hydroxy-(C$_1$–C$_4$)alkyl or phenyl optionally independently substituted with up to three hydroxy, halo, hydroxy-(C$_1$–C$_4$)alkyl, (C$_1$–C$_4$)alkoxy-(C$_1$–C$_4$)alkyl, (C$_1$–C$_4$)alkyl or (C$_1$–C$_4$)alkoxy, wherein said (C$_1$–C$_4$)alkyl in the definition of R$^6$ and said (C$_1$–C$_4$)alkoxy in the definition of R$^6$ are optionally and independently substituted with up to five fluoro; R$^7$ and R$^8$ are each independently hydrogen or (C$_1$–C$_4$)alkyl; or
G and G$^1$ in the compound of formula SDI are taken together and are (C$_1$–C$_3$)alkylene and R$^6$, R$^7$, R$^8$ and G$^2$ are hydrogen; or G$^1$ and G$^2$ in the compound of formula SDI are taken together and are (C$_1$–C$_3$)alkylene and R$^6$, R$^7$, R$^8$ and G are hydrogen;
q in the compound of formula SDI is 0 or 1;
X in the compound of formula SDI is a covalent bond, —(C=NR$^{10}$)—, oxycarbonyl, vinylenylcarbonyl, oxy(C$_1$–C$_4$)alkylenylcarbonyl, (C$_1$–C$_4$)alkylenylcarbonyl, (C$_3$–C$_4$)alkenylcarbonyl, thio(C$_1$–C$_4$)alkylenylcarbonyl,

30 vinylenylsulfonyl, sulfinyl-(C$_1$–C$_4$)alkylenylcarbonyl, sulfonyl-(C$_1$–C$_4$)alkylenylcarbonyl or carbonyl(C$_0$–C$_4$) alkylenylcarbonyl; wherein said oxy(C$_1$–C$_4$) alkylenylcarbonyl, (C$_1$–C$_4$)alkylenylcarbonyl, (C$_3$–C$_4$) alkenylcarbonyl and thio(C$_1$–C$_4$)alkylenylcarbonyl in the definition of X are each optionally and independently substituted with up to two (C$_1$–C$_4$)alkyl, benzyl or Ar; said vinylenylsulfonyl and said vinylenylcarbonyl in the definition of X are optionally substituted independently on one or two vinylenyl carbons with (C$_1$–C$_4$)alkyl, benzyl or Ar; and said carbonyl(C$_0$–C$_4$)alkylenylcarbonyl in the definition of X is optionally substituted independently with up to three (C$_1$–C$_4$)alkyl, benzyl or Ar;
R$^{10}$ in the compound of formula SDI is hydrogen or (C$_1$–C$_4$) alkyl;
R$^9$ in the compound of formula SDI is (C$_3$–C$_7$)cycloalkyl, Ar$^1$—(C$_0$–C$_3$)alkylenyl or (C$_1$–C$_6$)alkyl optionally substituted with up to five fluoro; provided that when q=0 and X is a covalent bond, oxycarbonyl or (C$_1$–C$_4$) alkylenylcarbonyl, then R$^9$ is not (C$_1$–C$_6$)alkyl;
Ar and Ar$^1$ in the compound of formula SDI are independently a fully saturated, partially saturated or fully unsaturated five- to eight-membered ring optionally having up to four heteroatoms selected independently from oxygen, sulfur and nitrogen, or a bicyclic ring consisting of two fused independently partially saturated, fully saturated or fully unsaturated five- to seven-membered rings, taken independently, optionally having up to four heteroatoms selected independently from nitrogen, sulfur and oxygen, or a tricyclic ring consisting of three fused independently partially saturated, fully saturated or fully unsaturated five to seven membered rings, taken independently, optionally having up to four heteroatoms selected independently from nitrogen, sulfur and oxygen, said partially saturated, fully saturated ring or fully unsaturated monocyclic ring, bicyclic ring or tricyclic ring optionally having one or two oxo groups substituted on carbon or one or two oxo groups substituted on sulfur; Ar and Ar$^1$ in the compound of formula SDI are optionally independently substituted on carbon or nitrogen, on one ring if the moiety is monocyclic, on one or both rings if the moiety is bicyclic, or on one, two or three rings if the moiety is tricyclic, with up to a total of four substituents independently selected from R$^{11}$, R$^{12}$, R$^{13}$ and R$^{14}$; wherein R$^{11}$, R$^{12}$, R$^{13}$ and R$^{14}$ are each taken separately and are each independently halo, formyl, (C$_1$–C$_6$)alkoxycarbonyl, (C$_1$–C$_6$) alkylenyloxycarbonyl, (C$_1$–C$_4$)alkoxy-(C$_1$–C$_4$)alkyl, C(OH)R$^{15}$R$^{16}$, naphthyl, phenyl, imidazolyl, pyridyl, triazolyl, morpholinyl, (C$_0$–C$_4$)alkylsulfamoyl, N-(C$_0$–C$_4$)alkylcarbamoyl, N,N-di-(C$_1$–C$_4$) alkylcarbamoyl, N-phenylcarbamoyl, N-(C$_1$–C$_4$)alkyl-N-phenylcarbamoyl, N,N-diphenyl carbamoyl, (C$_1$–C$_4$) alkylcarbonylamido, (C$_3$–C$_7$)cycloalkylcarbonylamido, phenylcarbonylamido, piperidinyl, pyrrolidinyl, piperazinyl, cyano, benzimidazolyl, amino, anilino, pyrimidyl, oxazolyl, isoxazolyl, tetrazolyl, thienyl, thiazolyl, benzothiazolyl, pyrrolyl, pyrazolyl, tetrahydroquinolyl, tetrahydroisoquinolyl, benzoxazolyl, pyridazinyl, pyridyloxy, pyridylsulfanyl, furanyl, 8-(C$_1$–C$_4$)alkyl-3,8-diaza[3.2.1]bicyclooctyl, 3,5-dioxo-1,2,4-triazinyl, phenoxy, thiophenoxy, (C$_1$–C$_4$) alkylsulfanyl, (C$_1$–C$_4$)alkylsulfonyl, (C$_3$–C$_7$)cycloalkyl, (C$_1$–C$_4$)alkyl optionally substituted with up to five fluoro or (C$_1$–C$_4$)alkoxy optionally substituted with up to five fluoro; said naphthyl, phenyl, pyridyl, piperidinyl, benzimidazolyl, pyrimidyl, thienyl, benzothiazolyl, pyrrolyl, tetrahydroquinolyl, tetrahydroisoquinolyl, benzoxazolyl, pyridazinyl, pyridyloxy, pyridylsulfanyl, furanyl, thiophenoxy, anilino and phenoxy in the definition of $R^{11}$, $R^{12}$, $R^{13}$ and $R^{14}$ are optionally substituted with up to three substituents independently selected from hydroxy, halo, hydroxy-$(C_1–C_4)$alkyl, $(C_1–C_4)$alkoxy-$(C_1–C_4)$alkyl, $(C_1–C_4)$alkyl optionally substituted with up to five fluoro and $(C_1–C_4)$alkoxy optionally substituted with up to five fluoro; said imidazolyl, oxazolyl, isoxazolyl, thiazolyl and pyrazolyl in the definition of $R^{11}$, $R^{12}$, $R^{13}$ and $R^{14}$ are optionally substituted with up to two substituents independently selected from hydroxy, halo, hydroxy-$(C_1–C_4)$alkyl, $(C_1–C_4)$alkoxy-$(C_1–C_4)$alkyl, $(C_1–C_4)$alkyl optionally substituted with up to five fluoro and $(C_1–C_4)$alkoxy optionally substituted with up to five fluoro; said morpholinyl in the definition of $R^{11}$, $R^{12}$, $R^{13}$ and $R^{14}$ is optionally substituted with up to two substituents independently selected from $(C_1–C_4)$alkyl; said pyrrolidinyl in the definition of $R^{11}$, $R^{12}$, $R^{13}$ and $R^{14}$is optionally substituted with up to two substituents independently selected from hydroxy, hydroxy-$(C_1–C_3)$alkyl, $(C_1–C_4)$alkoxy-$(C_1–C_4)$alkyl, $(C_1–C_4)$alkyl optionally substituted with up to five fluoro and $(C_1–C_4)$alkoxy optionally substituted with up to five fluoro; said piperazinyl in the definition of $R^{11}$, $R^{12}$, $R^{13}$ and $R^{14}$ is optionally substituted with up to three substituents independently selected from $(C_1–C_4)$alkoxy-$(C_1–C_4)$alkyl, hydroxy-$(C_1–C_3)$alkyl, phenyl, pyridyl, $(C_0–C_4)$ alkylsulfamoyl, $(C_1–C_4)$alkyl optionally substituted with up to five fluoro and $(C_1–C_4)$alkoxy optionally substituted with up to five fluoro; said triazolyl in the definition of $R^{11}$, $R^{12}$, $R^{13}$ and $R^{14}$ is optionally substituted with hydroxy, halo, hydroxy-$(C_1–C_4)$alkyl, $(C_1–C_4)$alkoxy-$(C_1–C_4)$alkyl, $(C_1–C_4)$alkyl optionally substituted with up to five fluoro and $(C_1–C_4)$alkoxy optionally substituted with up to five fluoro; said tetrazolyl in the definition of $R^{11}$, $R^{12}$, $R^{13}$ and $R^{14}$ is optionally substituted with hydroxy-$(C_2–C_3)$alkyl or $(C_1–C_4)$alkyl optionally substituted with up to five fluoro; and said phenyl and pyridyl which are optionally substituted on piperazine in the definition of $R^{11}$, $R^{12}$, $R^{13}$ and $R^{14}$ are optionally substituted with up to three hydroxy, halo, hydroxy-$(C_1–C_4)$alkyl, $(C_1–C_4)$alkoxy-$(C_1–C_4)$alkyl, $(C_1–C_4)$alkyl optionally substituted with up to five fluoro and $(C_1–C_4)$alkoxy optionally substituted with up to five fluoro; or $R^{11}$ and $R^{12}$ in the compound of formula SDI are taken together on adjacent carbon atoms and are
—$CH_2OC(CH_3)_2OCH_2$— or —O—$(CH_2)_p$—O—, and $R^{13}$ and $R^{14}$ are taken separately and are each independently hydrogen or $(C_1–C_4)$alkyl;

p in the compound of formula SDI is 1, 2 or 3;

$R^{15}$ and $R^{16}$ in the compound of formula SDI are taken separately and are each independently hydrogen, $(C_1–C_4)$ alkyl optionally substituted with up to five fluoro; or $R^{15}$ and $R^{16}$ are taken separately and $R^{15}$ is hydrogen and $R^{16}$ is $(C_3–C_6)$cycloalkyl, hydroxy-$(C_1–C_3)$alkyl, phenyl, pyridyl, pyrimidyl, thienyl, furanyl, thiazolyl, oxazolyl, imidazolyl, benzothiazolyl or benzoxazolyl; or $R^{15}$ and $R^{16}$ are taken together and are $(C_3–C_6)$alkylene;

$G^3$, $G^4$ and $G^5$ in the compound of formula SDI are taken separately and are each hydrogen; r is 0; $R^{18}$ is hydrogen, $(C_1–C_4)$alkyl, $(C_1–C_4)$alkoxycarbonyl, $(C_1–C_4)$alkoxy-$(C_1–C_4)$alkyl, hydroxy-$(C_1–C_4)$alkyl or phenyl optionally independently substituted with up to three hydroxy, halo, hydroxy-$(C_1–C_4)$alkyl, $(C_1–C_4)$alkoxy-$(C_1–C_4)$alkyl, $(C_1–C_4)$alkyl or $(C_1–C_4)$alkoxy, wherein said $(C_1–C_4)$ alkyl in the definition of $R^6$ and said $(C_1–C_4)$alkoxy in the definition of $R^6$ are optionally and independently substituted with up to five fluoro; and $R^{19}$ and $R^{20}$ are each independently $(C_1–C_4)$alkyl; or $G^3$, $G^4$ and $G^5$ are taken separately and are each hydrogen; r is 1; $R^{18}$ is hydrogen, $(C_1–C_4)$alkyl, $(C_1–C_4)$ alkoxycarbonyl, $(C_1–C_4)$alkoxy-$(C_1–C_4)$alkyl, hydroxy-$(C_1–C_4)$alkyl or phenyl optionally independently substituted with up to three hydroxy, halo, hydroxy-$(C_1–C_4)$ alkyl, $(C_1–C_4)$alkoxy-$(C_1–C_4)$alkyl, $(C_1–C_4)$alkyl or $(C_1–C_4)$alkoxy, wherein said $(C_1–C_4)$alkyl in the definition of $R^6$ and said $(C_1–C_4)$alkoxy in the definition of $R^6$are optionally and independently substituted with up to five fluoro; and $R^{19}$ and $R^{20}$ are each independently hydrogen or $(C_1–C_4)$alkyl; or $G^3$ and $G^4$ in the compound of formula SDI are taken together and are $(C_1–C_3)$alkylene; r is 0 or 1; and $R^{18}$, $R^{19}$, $R^{20}$ and $G^5$ are hydrogen; or $G^4$ and $G^5$ are taken together and are $(C_1–C_3)$alkylene; r is 0 or 1; and $R^{18}$, $R^{19}$, $R^{20}$ and $G^3$ are hydrogen;

$R^{17}$ in the compound of formula SDI is $SO_2NR^{21}R^{22}$, $CONR^{21}R^{22}$, $(C_1–C_6)$alkoxycarbonyl, $(C_1–C_6)$ alkylcarbonyl, $Ar^2$-carbonyl, $(C_1–C_6)$alkylsulfonyl, $(C_1–C_6)$alkylsulfinyl, $Ar^2$-sulfonyl, $Ar^2$-sulfinyl and $(C_1–C_6)$alkyl;

$R^{21}$ and $R^{22}$ in the compound of formula SDI are taken separately and are each independently selected from hydrogen, $(C_1–C_6)$alkyl, $(C_3–C_7)$cycloalkyl and $Ar^2$-$(C_0–C_4)$alkylenyl; or $R^{21}$ and $R^{22}$ in the compound of formula SDI are taken together with the nitrogen atom to which they are attached to form azetidinyl, pyrrolidinyl, piperidinyl, piperazinyl, morpholinyl, azepinyl, azabicyclo[3.2.2]nonanyl, azabicyclo[2.2.1]heptyl, 6,7-dihydro-5H-dibenzo[c,e] azepinyl, 1,2,3,4-tetrahydro-isoquinolyl or 5,6,7,8-tetrahydropyrido[4,3-d]pyrimidyl; said azetidinyl in the definition of $R^{21}$ and $R^{22}$ is optionally substituted independently with one substituent selected from hydroxy, amino, hydroxy-$(C_1–C_4)$alkyl, $(C_1–C_4)$alkoxy-$(C_1–C_4)$ alkyl, $(C_1–C_4)$alkyl optionally substituted with up to five fluoro and $(C_1–C_4)$alkoxy optionally substituted with up to five fluoro; said pyrrolidinyl, piperidinyl, azepinyl in the definition of $R^{21}$ and $R^{22}$ are optionally substituted independently with up to two substituents independently selected from hydroxy, amino, hydroxy-$(C_1–C_4)$alkyl, $(C_1–C_4)$alkoxy-$(C_1–C_4)$alkyl, $(C_1–C_4)$alkyl optionally substituted with up to five fluoro and $(C_1–C_4)$alkoxy optionally substituted with up to five fluoro; said morpholinyl in the definition of $R^{21}$ and $R^{22}$ is optionally substituted with up to two substituents independently selected from hydroxy-$(C_1–C_4)$alkyl, $(C_1–C_4)$alkoxy-$(C_1–C_4)$alkyl, $(C_1–C_4)$alkyl optionally substituted with up to five fluoro and $(C_1–C_4)$alkoxy optionally substituted with up to five fluoro; said piperazinyl in the definition of $R^{21}$ and $R^{22}$ is optionally substituted independently with up to three substituents independently selected from phenyl, pyridyl, pyrimidyl, $(C_1–C_4)$alkoxycarbonyl and $(C_1–C_4)$alkyl optionally substituted with up to five fluoro; said 1,2,3,4-tetrahydro-isoquinolyl and said 5,6,7,8-tetrahydropyrido[4,3-d]pyrimidyl in the definition of $R^{21}$ and $R^{22}$ are optionally substituted independently with up to three substituents independently selected from hydroxy, amino, halo, hydroxy-$(C_1–C_4)$alkyl, $(C_1–C_4)$ alkoxy-$(C_1–C_4)$alkyl, $(C_1–C_4)$alkyl optionally substituted with up to five fluoro and $(C_1–C_4)$alkoxy optionally substituted with up to five fluoro; and said 6,7-dihydro-5H-dibenzo[c,e]azepinyl in the definition of $R^{21}$ and $R^{22}$ is optionally substituted with up to four substituents independently selected from hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said pyrimidyl, pyridyl and phenyl which are optionally substituted on said piperazine in the definition of $R^{21}$ and $R^{22}$ is optionally substituted with up to three substituents selected from hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro;

$Ar^2$ in the compound of formula SDI is independently defined as set forth for Ar and $Ar^1$ above;

said $Ar^2$ is optionally independently substituted as set forth for Ar and $Ar^1$ above;

$R^{23}$ in the compound of formula SDI is $CONR^{25}R^{26}$ or $SO_2R^{25}R^{26}$, wherein $R^{25}$ is hydrogen $(C_1-C_4)$alkyl or $Ar^3$—$(C_0-C_4)$alkylenyl and $R^{26}$ is $Ar^3$—$(C_0-C_4)$alkylenyl; provided that when $Ar^3$ is phenyl, naphthyl or biphenyl, then $R^{23}$ cannot be $CONR^{25}R^{26}$ where $R^{25}$ in the compound of formula SDI is hydrogen or $Ar^3$ and $R^{26}$ is $Ar^3$;

$R^{24}$ in the compound of formula SDI is hydrogen, $(C_1-C_4)$alkyl, $(C_1-C_4)$alkoxycarbonyl, $(C_1-C_4)$alkoxy-$(C_1-C_4)$alkyl, hydroxy-$(C_1-C_4)$alkyl or phenyl optionally independently substituted with up to three hydroxy, halo, hydroxy-$(C_1-C_4)$alkyl, $(C_1-C_4)$alkoxy-$(C_1-C_4)$alkyl, $(C_1-C_4)$alkyl or $(C_1-C_4)$alkoxy, wherein said $(C_1-C_4)$alkyl in the definition of $R^6$ and said $(C_1-C_4)$alkoxy in the definition of $R^6$ are optionally and independently substituted with up to five fluoro;

$Ar^3$ in the compound of formula SDI is independently defined as set forth for Ar and $Ar^1$ above;

said $Ar^3$ is optionally independently substituted as set forth for Ar and $Ar^1$ above;

$R^{27}$ in the compound of formula SDI is hydrogen or $(C_1-C_4)$alkyl;

$R^{28}$ and $R^{29}$ in the compound of formula SDI are each independently hydrogen, hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro, $(C_1-C_4)$alkoxy optionally substituted with up to five fluoro, phenyl, pyridyl, pyrimidyl, thienyl, furanyl, thiazolyl, oxazolyl, phenoxy, thiophenoxy, $SO_2NR^3OR^3$, $CONR^{30}R^{31}$ or $NR^{30}R^{31}$; said thienyl, pyrimidyl, furanyl, thiazolyl and oxazolyl in the definition of $R^{23}$ and $R^{29}$ are optionally substituted by up to two hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said phenyl, pyridyl, phenoxy and thiophenoxy in the definition of $R^{28}$ and $R^{29}$ are optionally substituted by up to three hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro;

$R^{30}$ and $R^{31}$ in the compound of formula SDI are each independently hydrogen, $(C_1-C_4)$alkyl, $(C_3-C_7)$cycloalkyl or phenyl, said phenyl is optionally substituted with up to three hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; or $R^{30}$ and $R^{31}$ in the compound of formula SDI are taken together with the nitrogen to which they are attached to form indolinyl, pyrrolidinyl, piperidinyl, piperazinyl or morpholinyl; said pyrrolidinyl and piperidinyl in the definition of $R^{30}$ and $R^{31}$ are optionally substituted with up to two hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said indolinyl and piperazinyl in the definition of $R^{30}$ and $R^{31}$ are optionally substituted with up to three hydroxy, amino, hydroxy-$(C_1-C_4)$alkyl, $(C_1-C_4)$alkoxy-$(C_1-C_4)$alkyl, $(C_1-C_4)$alkoxycarbonyl, $(C_1-C_4)$alkyl optionally substituted with up to five fluoro or $(C_1-C_4)$alkoxy optionally substituted with up to five fluoro; said morpholinyl in the definition of $R^{30}$ and $R^{31}$ is optionally substituted with up to two substituents independently selected from hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro;

A in the compound of formula SDI is N optionally substituted with hydrogen or $(C_1-C_4)$alkyl and B is carbonyl; or A in the compound of formula SDI is carbonyl and B is N optionally substituted with hydrogen or $(C_1-C_4)$alkyl;

$R^{32}$ in the compound of formula SDI is hydrogen or $(C_1-C_4)$alkyl;

$R^{33}$ in the compound of formula SDI is phenyl, pyridyl, pyrimidyl, thiazolyl, oxazolyl, benzyl, quinolyl, isoquinolyl, phthalizinyl, quinoxanlyl, benzothiazoyl, benzoxazolyl, benzofuranyl or benzothienyl; said phenyl, pyridyl, pyrimidyl, thiazolyl, oxazolyl, benzyl, quinolyl, isoquinolyl, phthalizinyl, quinoxanlyl, benzothiazoyl, benzoxazolyl, benzofuranyl and benzothienyl in the definition of $R^{33}$ are optionally substituted with up to three phenyl, phenoxy, $NR^{34}R^{35}$, halo, hydroxy, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro;

$R^{34}$ and $R^{35}$ in the compound of formula SDI are each independently hydrogen, $(C_1-C_4$ alkyl$)$, phenyl or phenylsulfonyl; said phenyl and phenylsulfonyl in the definition of $R^{34}$ and $R^{35}$ are optionally substituted with up to three halo, hydroxy, $(C_1-C_4)$alkyl optionally substituted with up to five fluoro or $(C_1-C_4)$alkoxy optionally substituted with up to five fluoro;

D in the compound of formula SDI is CO, CHOH or $CH_2$;

E in the compound of formula SDI is O, NH or S;

$R^{36}$ and $R^{37}$ in the compound of formula SDI are taken separately and are each independently hydrogen, halo, cyano, hydroxy, amino, $(C_1-C_6)$alkylamino, di-$(C_1-C_6)$alkylamino, pyrrolidino, piperidino, morpholino, $(C_1-C_4)$alkoxy-$(C_1-C_4)$alkyl, hydroxy-$(C_1-C_4)$alkyl, $Ar^4$, $(C_1-C_4)$alkyl optionally substituted with up to five fluoro or $(C_1-C_4)$alkoxy optionally substituted with up to five fluoro;

$R^{38}$, $R^{39}$ and $R^{40}$ in the compound of formula SDI are each independently hydrogen or $(C_1-C_4)$-alkyl;

$Ar^4$ in the compound of formula SDI is phenyl, furanyl, thienyl, pyridyl, pyrimidyl, pyrazinyl or pyridazinyl; said $Ar^4$ being optionally substituted with up to three hydroxy, $(C_1-C_4)$alkoxy-$(C_1-C_4)$alkyl, halo, hydroxy-$(C_1-C_4)$alkyl, $(C_1-C_4)$alkyl optionally substituted with up to five fluoro or $(C_1-C_4)$alkoxy optionally substituted with up to five fluoro; or $R^{36}$ and $R^{37}$ in the compound of formula SDI are taken together on adjacent carbon atoms and are —O—$(CH_2)_t$—O—;

t in the compound of formula SDI is 1, 2 or 3;

Y in the compound of formula SDI is $(C_2-C_6)$alkylene;

$R^{44}$, $R^{45}$ and $R^{46}$ in the compound of formula SDI are each independently hydrogen or $(C_1-C_4)$alkyl;

m and n in the compound of formula SDI are each independently 1, 2 or 3, provided that the sum of m and n is 2, 3 or 4;

k in the compound of formula SDI is 0, 1, 2, 3 or 4;

$Y^1$ in the compound of formula SDI is a covalent bond, carbonyl, sulfonyl or oxycarbonyl;

$R^{43}$ in the compound of formula SDI is $(C_3-C_7)$cycloalkyl, $Ar^5-(C_0-C_4)$alkylenyl, $NR^{47}R^{48}$ or $(C_1-C_6)$alkyl optionally substituted with one to five fluoro; provided that when $Y^1$ is a covalent bond or oxycarbonyl, then $R^{43}$ is not $NR^{47}R^{43}$;

$R^{47}$ and $R^{48}$ in the compound of formula SDI are taken separately and are each independently selected from hydrogen, $Ar^5$, $(C_1-C_6)$alkyl and $Ar^5-(C_0-C_4)$alkylenyl; or $R^{47}$ and $R^{48}$ in the compound of formula SDI are taken together with the nitrogen atom to which they are attached to form azetidinyl, pyrrolidinyl, piperidinyl, piperazinyl, morpholinyl, azepinyl, azabicyclo[3.2.2]nonanyl, azabicyclo[2.2.1]heptyl, 1,2,3,4-tetrahydroisoquinolyl, 6,7-dihydro-5H-dibenzo[c,e]azepinyl or 5,6,7,8-tetrahydropyrido[4,3-d]pyrimidyl; said azetidinyl in the definition of $R^{47}$ and $R^{48}$ are optionally substituted with one hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said pyrrolidinyl, piperidinyl and azepinyl in the definition of $R^{47}$ and $R^{48}$ are optionally substituted with up to two hydroxy, amino, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; said morpholinyl in the definition of $R^{47}$ and $R^{48}$ is optionally substituted with up to two substituents independently selected from hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said piperazinyl, 1,2,3,4-tetrahydroisoquinolyl and 5,6,7,8-tetrahydro[4,3-d]pyrimidyl in the definition of $R^{47}$ and $R^{48}$ are optionally substituted with up to three hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro; and said 6,7-dihydro-5H-dibenzo[c,e]azepinyl in the definition of $R^{47}$ and $R^{48}$ are optionally substituted with up to four hydroxy, amino, halo, hydroxy-$(C_1-C_4)$alkyl, $(C_1-C_4)$alkoxy-$(C_1-C_4)$alkyl, $(C_1-C_4)$alkyl optionally substituted with up to five fluoro or $(C_1-C_4)$alkoxy optionally substituted with up to five fluoro;

$Ar^5$ in the compound of formula SDI is independently defined as set forth for Ar and $Ar^1$ above;

$Ar^5$ in the compound of formula SDI is optionally independently substituted as set forth for Ar and $Ar^1$ above;

$R^{42}$ and $R^{42a}$ in the compound of formula SDI are independently hydrogen, $(C_3-C_7)$cycloalkyl, $Ar^6-(C_0-C_3)$alkylenyl, $Ar^6-(C_2-C_4)$alkenyl, $Ar^6$-carbonyl or $(C_1-C_6)$alkyl optionally substituted with up to five fluoro;

$Ar^6$ in the compound of formula SDI is independently defined as set forth for Ar and $Ar^1$ above;

$Ar^6$ in the compound of formula SDI is optionally independently substituted as set forth for Ar and $Ar^1$ above; and $R^{41}$ and $R^{41a}$ in the compound of formula SDI are each independently hydrogen or $(C_1-C_4)$alkyl.

Especially preferred SDI compounds include 1R-(4-{1'-[2-(1R-hydroxy-ethyl)-pyrimidin-4-yl]-[4,4']bipiperidinyl-1-yl}-pyrimidin-2-yl)-ethanol; furo[3,2-c]pyridin-2-yl-{4-[2-(1R-hydroxy-ethyl)-pyrimidin-4-yl]-3R,5S-dimethyl-piperazin-1-yl}-methanone; (4-chloro-furo[3,2-c]pyridin-2-yl)-{4-[2-(1R-hydroxy-ethyl)pyrimidin-4-yl]-3R,5S-dimethyl-piperazin-1-yl}-methanone; {4-[2-(1R-hydroxy-ethyl)-pyrimidin-4-yl]-3R,5S-dimethyl-piperazin-1-yl}-(4-pyrrolidin-1-yl-furo[3,2-c]pyridin-2-yl)-methanone; {4-[2-(1R-hydroxy-ethyl)-pyrimidin-4-yl]-3R,5S-dimethyl-piperazin-1-yl}-(4-morpholin-4-yl-furo[3,2-c]pyridin-2-yl)-methanone; {4-[2-(1R-hydroxy-ethyl)-pyrimidin-4-yl]-3R,5S-dimethyl-piperazin-1-yl}-imidazo[1,2-a]pyridin-2-yl-methanone; furo[3,2-c]pyridin-2-yl-{4-[2-(1R-hydroxy-ethyl)-pyrimidin-4-yl]-2R,6S-dimethyl-piperazin-1-yl}-methanone; 4-[2-(1R-hydroxy-ethyl)-pyrimidin-4-yl]-2R,6S-dimethyl-piperazine-1-carboxylic acid pyridin-3-yl ester; 4-[2-(1R-hydroxy-ethyl)-pyrimidin-4-yl]-2R,6S-dimethyl-piperazine-1-carboxylic acid 2-methyl-pyridin-3-yl ester; 4-[2-(1R-hydroxy-ethyl)-pyrimidin-4-yl]-2R,6S-dimethyl-piperazine-1-carboxylic acid 5-chloro-pyridin-3-yl ester; 4-[2-(1R-hydroxy-ethyl)-pyrimidin-4-yl]-2R,6S-dimethyl-piperazine-1-carboxylic acid 6-methyl-pyridin-3-yl ester; (E)-1-{4-[2-(1R-hydroxy-ethyl)-pyrimidin-4-yl]-2R,6S-dimethyl-piperazin-1-yl}-3-thiophen-2-yl-propenone; 1R-{4-[4-(4,6-dimethyl-pyrimidin-2-yl)-3R,5S-dimethyl-piperazin-1-yl]-pyrimidin-2-yl}-ethanol; 1R-{4-[4-(4-methoxymethyl-6-methyl-pyrimidin-2-yl)-3R,5S-dimethyl-piperazin-1-yl]-pyrimidin-2-yl}-ethanol; 1R-{4-[4-(4-hydroxymethyl-6-methyl-pyrimidin-2-yl)-3R,5S-dimethyl-piperazin-1-yl]-pyrimidin-2-yl}-ethanol; 1R-(4-{3R,5S-dimethyl-4-[2-(4-methyl-piperazin-1-yl)-pyrimidin-4-yl]-piperazin-1-yl}-pyrimidin-2-yl)-ethanol; 1R-(4-{4-[2-(4-ethyl-piperazin-1-yl)-pyrimidin-4-yl]-3R,5S-dimethyl-piperazin-1-yl}-pyrimidin-2-yl)-ethanol; 1R-(4-{3R,5S-dimethyl-4-[2-(4-methyl-imidazol-1-yl)-pyrimidin-4-yl]-piperazin-1-yl}-pyrimidin-2-yl)-ethanol; 1R-(4-{3R,5S-dimethyl-4-[2-(2-methyl-imidazol-1-yl)-pyrimidin-4-yl]-piperazin-1-yl}-pyrimidin-2-yl)-ethanol; 1R-(4-{4-[2-(2,4-dimethyl-imidazol-1-yl)-pyrimidin-4-yl]-3R,5S-dimethyl-piperazin-1-yl}-pyrimidin-2-yl)-ethanol; 1R-(4-{4-[2-(4-isopropyl-piperazin-1-yl)-pyrimidin-4-yl]-3R,5S-dimethyl-piperazin-1-yl}-pyrimidin-2-yl)-ethanol; 1R-(4-{3R,5S-dimethyl-4-[4-methyl-6-(4-methyl-piperazin-1-yl)-[1,3,5]triazin-2-yl]-piperazin-1-yl}-pyrimidin-2-yl)-ethanol; 1R-{4-[4-(4-methoxy-6-methyl-[1,3,5]triazin-2-yl)-3R,5S-dimethyl-piperazin-1-yl]-pyrimidin-2-yl}-ethanol; 1R-{4-[4-(4,6-dimethoxy-[1,3,5]triazin-2-yl)-3R,5S-dimethyl-piperazin-1-yl]-pyrimidin-2-yl}-ethanol; 1R-{4-[4-(4-ethoxy-6-methyl-[1,3,5]triazin-2-yl)-3R,5S-dimethyl-piperazin-1-yl]-pyrimidin-2-yl}-ethanol; 1R-{4-[4-(4-isopropoxy-6-methyl-[1,3,5]triazin-2-yl)-3R,5S-dimethyl-piperazin-1-yl]-pyrimidin-2-yl}-ethanol; 1R-{4-[3R,5S-dimethyl-4-(4-phenyl-[1,3,5]triazin-2-yl)-piperazin-1-yl]-pyrimidin-2-yl}-ethanol; 1R-{4-[4-(4-hydroxymethyl-6-methoxy-[1,3,5]triazin-2-yl)-3R,5S-dimethyl-piperazin-1-yl]-pyrimidin-2-yl}-ethanol; 1R-{4-[4-(4-isopropoxy-6-methoxy-[1,3,5]triazin-2-yl)-3R,5S-dimethyl-piperazin-1-yl]-pyrimidin-2-yl}-ethanol; 1R-{4-[4-(4-isopropyl-[1,3,5]triazin-2-yl)-3R,5S-dimethyl-piperazin-1-yl]-pyrimidin-2-yl}-ethanol; 1R-{4-[4-(4-ethyl-6-methoxy-[1,3,5]triazin-2-yl)-3R,5S-dimethyl-piperazin-1-yl]-pyrimidin-2-yl}-ethanol; 1R-{4-[4-(4,6-dimethyl-pyrimidin-2-yl)-2R,6S-dimethyl-piperazin-1-yl]-pyrimidin-2-yl}-ethanol; 1R-{4-[4-(4-hydroxymethyl-6-methyl-pyrimidin-2-yl)-2R,6S-dimethyl-piperazin-1-yl]-pyrimidin-2-yl}-ethanol; 1R-{4-[2R,6S-dimethyl-4-(4-[1,2,4]triazol- 1-yl-pyrimidin-2-yl)-piperazin-1-yl]-pyrimidin-2-yl}-ethanol; 1R-{4-[4-(2,6-dimethyl-pyrimidin-4-yl)-2R,6S-dimethyl-piperazin-1-yl]-pyrimidin-2-yl}-ethanol; 1R-(4-{4-[2-(1R-hydroxy-ethyl)-pyrimidin-4-yl]-2R,6S-dimethyl-piperazin-1-yl}-pyrimidin-2-yl)-ethanol; 1R-{4-[4-(2-hydroxymethyl-6-methyl-pyrimidin-4-yl)-2R,6S-dimethyl-piperazin-1-yl]-pyrimidin-2-yl}-ethanol; 1R-(4-{4-[2-(1S-hydroxy-ethyl)-pyrimidin-4-yl]-2R,6S-dimethyl-piperazin-1-yl}-pyrimidin-2-yl)-ethanol; 1S-(4-{4-[2-(1R-hydroxy-ethyl)-pyrimidin-4-yl]-2R,6S-dimethyl-piperazin-1-yl}-pyrimidin-2-yl)-ethanol; 1-{4-[4-(2-acetyl-pyrimidin-4-yl)-2R,6S-dimethyl-piperazin-1-yl]-pyrimidin-2-yl}-ethanone; 1RS-(4-{4-[2-(1RS-hydroxy-ethyl)-pyrimidin-4-yl]-2R,6S-dimethyl-piperazin-1-yl}-pyrimidin-2-yl)-ethanol; (4-{4-[2-(1R-hydroxy-ethyl)-pyrimidin-4-yl]-3R,5S-dimethyl-piperazin-1-yl}-pyrimidin-2-yl)-ethanone; 1R-{4-[2R,6S-dimethyl-4-(2-morpholin-4-yl-pyrimidin-4-yl)-piperazin-1-yl]-pyrimidin-2-yl}-ethanol; 1R-(4-{2R,6S-dimethyl-4-[2-(4-methyl-piperazin-1-yl)-pyrimidin-4-yl]-piperazin-1-yl}-pyrimidin-2-yl)-ethanol; 1R-{4-[2R,6S-dimethyl-4-(2-[1,2,4]triazol-1-yl-pyrimidin-4-yl)-piperazin-1-yl]-pyrimidin-2-yl}-ethanol; 1R-(4-{4-[2-(1R-hydroxy-ethyl)-pyrimidin-4-yl]-2R,6R-dimethyl-piperazin-1-yl}-pyrimidin-2-yl)-ethanol; 1R-(4-{4-[2-(4-ethyl-piperazin-1-yl)-pyrimidin-4-yl]-2R,6S-dimethyl-piperazin-1-yl}-pyrimidin-2-yl)-ethanol; 1R-(4-{2R,6S-dimethyl-4-[2-(4-methyl-imidazol-1-yl)-pyrimidin-4-yl]-piperazin-1-yl}-pyrimidin-2-yl)-ethanol; 1R-(4-{4-[2-(2,4-dimethyl-imidazol-1-yl)-pyrimidin-4-yl]-2R,6S-dimethyl-piperazin-1-yl}-pyrimidin-2-yl)-ethanol; 1R-{4-[2R,6S-dimethyl-4-(4-morpholin-4-yl-[1,3,5]triazin-2-yl)-piperazin-1-yl]-pyrimidin-2-yl}-ethanol; 1R-{4-[4-(4-methoxy-6-methyl-[1,3,5]triazin-2-yl)-2R,6S-dimethyl-piperazin-1-yl]-pyrimidin-2-yl}-ethanol; 1R-{4-[4-(4,6-dimethoxy-[1,3,5]triazin-2-yl)-2R,6S-dimethyl-piperazin-1-yl]-pyrimidin-2-yl}-ethanol; 1R-{4-[2R,6S-dimethyl-4-(4-phenyl-[1,3,5]triazin-2-yl)-piperazin-1-yl]-pyrimidin-2-yl}-ethanol; 1R-{4-[4-(4-hydroxymethyl-6-methyl-pyrimidin-2-yl)-3S-methyl-piperazin-1-yl]-pyrimidin-2-yl}-ethanol; 1R-{4-[4-(2-hydroxymethyl-pyrimidin-4-yl)-3S-methyl-piperazin-1-yl]-pyrimidin-2-yl}-ethanol; 1R-{4-[4-(2-hydroxymethyl-6-methyl-pyrimidin-4-yl)-3S-methyl-piperazin-1-yl]-pyrimidin-2-yl}-ethanol; 1R-[4-(3S-methyl-4-oxazolo[5,4-b]pyridin-2-yl-piperazin-1-yl)-pyrimidin-2-yl]-ethanol; 1R-[4-(3S-methyl-4-oxazolo[4,5-b]pyridin-2-yl-piperazin-1-yl)-pyrimidin-2-yl]-ethanol; 1R-[4-(3S-methyl-4-quinoxalin-2-yl-piperazin-1-yl)-pyrimidin-2-yl]-ethanol; (4-{4-[2-(1R-hydroxy-ethyl)-pyrimidin-4-yl]-2R,5S-dimethyl-piperazin-1-yl}-pyrimidin-2-yl)-ethanol; 1R-{4-[4-(4,6-dimethyl-[1,3,5]triazin-2-yl)-3R,5S-dimethyl-piperazin-1-yl]-pyrimidin-2-yl}-ethanol; 1R-{4-[3R,5S-dimethyl-4-(4-methyl-6-phenyl-[1,3,5]triazin-2-yl)-piperazin-1-yl]pyrimidin-2-yl}-ethanol; 1R-{4-[4-(4-cyclopropyl-[1,3,5]triazin-2-yl)-3R,5S-dimethyl-piperazin-1-yl]-pyrimidin-2-yl}-ethanol; 1R-{4-[4-(4-cyclopropyl-[1,3,5]triazin-2-yl)-2R,6S-dimethyl-piperazin-1-yl]-pyrimidin-2-yl}-ethanol; 1R-{4-[4-(4,6-dimethyl-[1,3,5]triazin-2-yl)-2R,6S-dimethyl-piperazin-1-yl]-pyrimidin-2-yl}-ethanol; 1R-{4-[4-(4-hydroxymethyl-6-phenyl-[1,3,5]triazin-2-yl)-2R,6S-dimethyl-piperazin-1-yl]-pyrimidin-2-yl}-ethanol; 1R-{4-[4-(4-methoxy-6-methoxymethyl-[1,3,5]triazin-2-yl)-2R,6S-dimethyl-piperazin-1-yl]-pyrimidin-2-yl}-ethanol; 1R-{4-[2R,6S-dimethyl-4-(4-methyl-[1,3,5]triazin-2-yl)-piperazin-1-yl]-pyrimidin-2-yl-ethanol; 1-{4-[4-(2-acetyl-pyrimidin-4-yl)-2R*,6S*-dimethyl-piperazin-1-yl]-pyrimidin-2-yl}-ethanone; 1-(-4-{4-[2-(1R-hydroxy-ethyl)-pyrimidin-4-yl]-2R,6S-dimethyl-piperazin-1-yl}-pyrimidin-2-yl)-ethanone; 1R-{4-[4-(4-methoxymethyl-6-phenyl-[1,3,5]-triazin-2-yl)-2R,6S-dimethyl-piperazin-1-yl]-pyrimidin-2-yl}-ethanol; and 1S-(4-{4-[2-(1R-hydroxy-ethyl)-pyrimidin-4-yl]-2R,6S-dimethyl-piperazin-1-yl}-pyrimidin-2-yl)-ethanol. An even more especially preferred SDI compound is 1R-(4-(4-(4,6-dimethyl)-[1,3,5]triazin-2-yl)-2R,6S-dimethyl-piperazin-1-yl)-pyrimidin-2-yl)-ethanol.

The preferred and especially preferred SDIs disclosed in the above two paragraphs can be prepared according to methods set forth in U.S. Pat. No. 6,414,149, filed on Apr. 1, 1999, or as set forth below, where the variables in the following schemes and description refer only to the SDI compounds.

Scheme 1

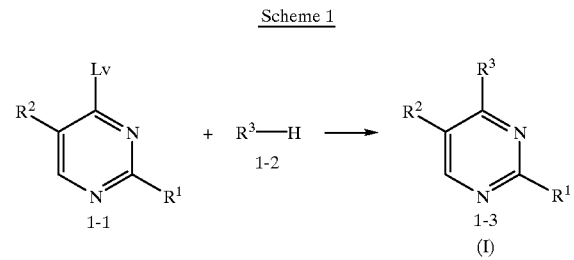

Compounds of formula 1-3 (i.e., formula 1) are prepared as set forth in Scheme 1, particularly as described below.

Compounds of formula 1-3 are prepared by the displacement reaction of a pyrimidine of the formula 1-1 where $R^1$ and $R^2$ are defined herein. Lv is a leaving group preferably selected from fluoro, chloro, bromo, iodo, thiomethyl, methylsulfone, or $OSO_2J$ wherein J is $(C_1-C_6)$-lower alkyl, trifluoromethyl, pentafluoroethyl, phenyl optionally substituted with up to three $(C_1-C_4)$alkyl, nitro or halo. The leaving group Lv is displaced by an amine of the formula 1-2 where $R^3$ is defined above. The reaction is conducted in the presence of a non-aqueous base, preferably an organic amine or an inorganic base. Preferred organic amines include triethylamine, pyridine, dimethylaminopyridine and N,N'-diisopropylethylamine (Hunig's base). Preferred inorganic bases include alkaline metal carbonates and bicarbonates such as sodium or potassium carbonate and sodium or potassium bicarbonate. An especially preferred inorganic base is potassium carbonate. An especially preferred organic amine is triethylamine. Alternatively, an excess of the reacting amine 1-2 can be used as the base for this reaction. The reaction can be conducted in the absence of solvent or in a reaction inert solvent. Where used herein, "reaction inert solvent" refers to a solvent which does not interact with starting materials, reagents, intermediates or products in a manner which adversely affects the yield of the desired product. Preferred reaction inert solvents include aqueous media, pyridine, $(C_1-C_4)$alcohol, $(C_2-C_6)$glycol, halocarbon, aliphatic/aromatic hydrocarbon, ethereal solvent, polar aprotic solvent, ketonic solvent, or combinations thereof. The reaction time ranges from 15 minutes to 3 days and the reaction temperature ranges from 0° C. to 180° C. Conveniently, the reaction may be conducted at the reflux temperature of the solvent being used. The reaction is preferably conducted at ambient pressure. The term ambient pressure, where used herein, refers to the pressure of the room in which the reaction is being conducted. The term ambient temperature, where used herein, refers to the temperature of the room in which the reaction is being conducted.

When $R^1$ contains a hydroxy group, the hydroxyl group may or may not be protected. When the hydroxyl group is protected, the protecting group may be any suitable hydroxyl protecting group. The conditions used to remove such optional hydroxyl protecting groups contained in $R^1$ in compounds of formula 1-3 are as follows. When the protecting group is an ester, removal of such ester protecting groups is conducted under basic conditions using inorganic hydroxides or carbonates, preferably lithium hydroxide, sodium hydroxide, potassium hydroxide or potassium carbonate. The reaction is carried out in a reaction inert solvent, preferably an alcoholic solvent. Especially preferred is methanol or methanol in combination with co-solvents such as water, tetrahydrofuran, or dioxane. The reaction time ranges from 15 minutes to 24 hours and the reaction temperature ranges from 0° C. to 100° C. or to the reflux temperature of the solvent(s) of use. Alternatively, ester cleavage may be accomplished under acidic conditions. It is preferred to utilize aqueous hydrochloric acid, generally 2 N to concentrated, with or without a co-solvent. When a co-solvent is used, dioxane or methanol are preferred. The reaction time ranges from 4 hours to 3 days and the reaction temperature ranges from 0° C. to 60° C.

When the protecting group is an alkyl ether, removal of such alkyl ether protecting groups is conducted using well known dealkylative conditions. For example, the alkyl ether may be cleaved by reaction with boron tribromide or diethylboron bromide in a reaction inert solvent, preferably a halocarbon solvent. It will be recognized by those skilled in the art that a buffer such as triethylamine may facilitate the reaction. The reaction times range from 15 minutes to 24 hours and the reaction temperature ranges from 0° C. to 60° C. In addition, a benzyl ether protecting group can be removed via standard or transfer hydrogenolysis using a palladium catalyst such as palladium on carbon. The hydrogenolysis reaction is conducted under a hydrogen atmosphere at ambient pressure to 50 psi in a reaction inert solvent, preferably methanol. The hydrogen source may be hydrogen gas, ammonium formate or trialkylammonium formate or cyclohexene. The reaction temperature ranges from room temperature to the reflux temperature of the solvent employed. The reaction time ranges from 15 minutes to 24 hours.

When a silyl ether protecting group is employed, removal of such silyl ether protecting groups is conducted under acidic conditions, preferably with aqueous hydrochloric acid such as 1 N to 6 N hydrochloric acid. The de-protection may be carried out in the presence of a co-solvent such as methanol or tetrahydrofuran. The reaction time ranges from 2 hours to 48 hours and the reaction temperature ranges from 0° C. to 100° C. Alternatively, the silyl ether protecting group may be removed via fluoride-mediated deprotection. In this case, deprotection is conducted using tetrabutylammonium fluoride or one of a variety of hydrofluoric acid sources in a reaction inert solvent. It is preferred to use ethereal solvents such as diethyl ether, dioxane or tetrahydrofuran, with tetrahydrofuran being especially preferred. The reaction time ranges from 2 hours to 48 hours and the reaction temperatures range from 0° C. to the reflux temperature of the solvent being used. Other methods for removal of the aforementioned protecting groups are well known to those skilled in the art or can be found in Greene, T. W.; Wuts, P. G. M., *Protective Groups in Organic Synthesis*, $2^{nd}$ ed.; John Wiley and Sons Inc.: New York, 1991. Other suitable hydroxyl protecting groups and methods for their removal may be found also be found therein. The method of Scheme I is preferred when $R^3$ is $R^{3k, l, m, n, o, p\ and\ q}$. Thus, compounds of formula 1-2 are reacted with compounds of formula 1-1. Compounds of formula 1-2 where $R^3$ is $R^{3k, l, m, n, o, p\ or\ q}$ are commercially available or can be prepared by methods well known to those skilled in the art.

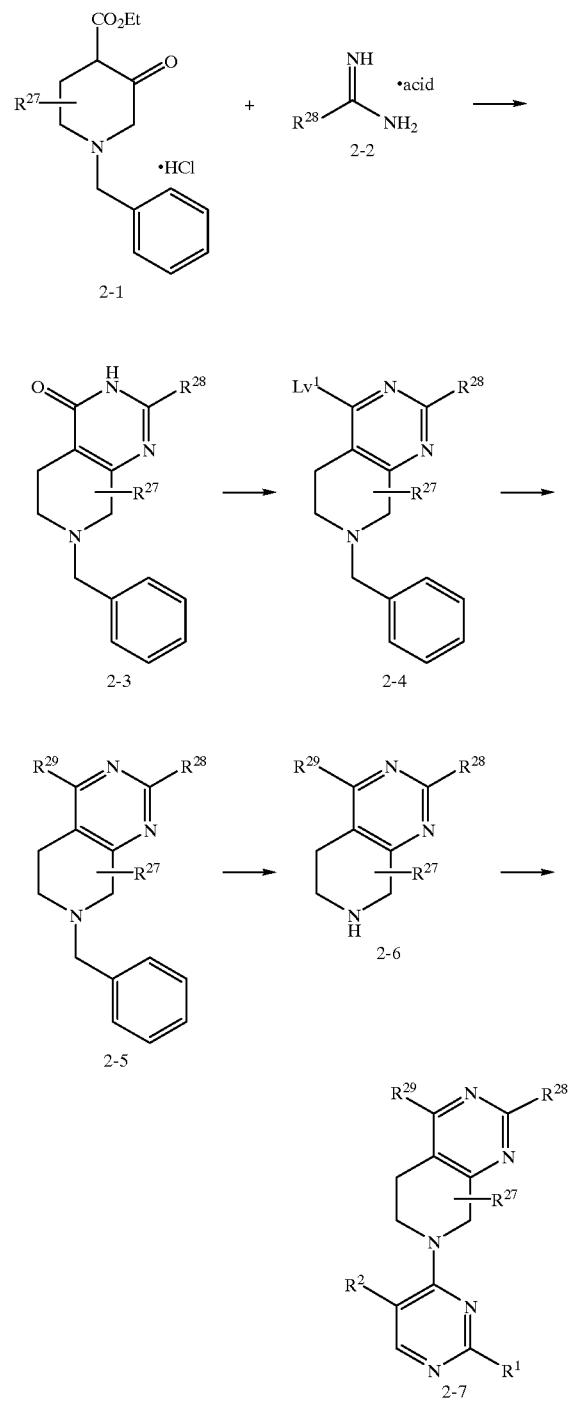

Scheme 2

Compounds of formula 2-7 are prepared as set forth in Scheme 2, particularly as described below.

Where $R^{27}$ is H, ethyl 1-benzyl-3-oxo-4-piperidinecarboxylate hydrochloride, the compound of formula 2-1, which is available from Aldrich, is condensed with compounds of formula 2-2 to give compounds of formula 2-3.

The compounds of formula 2-1 where $R^{27}$ is not H can be prepared according to methods well known to those skilled in the art. The reaction is conducted in the presence of excess base including non-aqueous bases, organic amines and inorganic bases. Preferred organic amines include triethylamine and pyridine. Preferred non-aqueous bases include alkaline metal $(C_1-C_4)$alkoxides. Preferred inorganic bases include potassium carbonate. The reaction is conducted in a reaction inert solvent. Preferred such solvents include $(C_1-C_4)$ alcohols, aromatic or aliphatic hydrocarbons, polar aprotic solvents, halocarbons, and ethereal solvents. $(C_1-C_4)$ Alcohols are especially preferred. The reaction time ranges from 2 hours to 3 days. The reaction temperature ranges from ambient temperature to the reflux temperature of the solvent being employed. The reaction is preferably run at ambient pressure but may be conducted at pressures up to 250 psi.

Compounds of formula 2-4 are prepared from compounds of formula 2-3 by converting a compound of formula 2-3 into an activated compound of formula 2-4 where $Lv^1$ is selected from fluoro, chloro, bromo, iodo, trifluoromethanesulfonate, $(C_1-C_6)$alkylsulfonate, or phenylsulfonate, wherein said phenyl is optionally substituted with up to three $(C_1-C_4)$alkyl, halo or nitro. This reaction is accomplished by reacting compounds of formula 2-3 with a chlorinating agent such as phosphorus oxychloride and/or phosphorus pentachloride to provide compounds of formula 2-4 where $Lv^1$ is chloro. This reaction is conducted at ambient pressure in the absence of solvent or in a reaction inert solvent, preferably a halocarbon solvent at temperatures ranging from ambient temperature to 180° C. Treatment of the chloro compound thus formed with the requisite mineral acid provides a compound of formula 2-4 where $Lv^1$ is bromo or iodo. A sulfonate of formula 2-4 is prepared by reaction of a compound of formula 2-3 with a sulfonic acid chloride or anhydride in the presence of an organic amine base, preferably triethylamine or pyridine. In certain cases recognized by those skilled in the art, it may be necessary to add a catalyst to the reaction. In those cases, a preferred catalyst is 4-dimethylaminopyridine. This reaction is conducted at ambient pressure in a reaction inert solvent, preferably pyridine, a halocarbon such as chloroform, dichloromethane or carbon tetrachloride, an aromatic or aliphatic hydrocarbon, an ethereal solvent, or combinations thereof. The reaction temperature ranges from −20° C. to 100° C. and the reaction time ranges from 15 minutes to 1 day.

Compounds of formula 2-5 wherein $R^{29}$ is defined above are prepared from compounds of formula 2-4 by a reduction reaction or by displacement of $Lv^1$ with a nucleophile. The reduction is conducted with a reducing agent, preferably ammonium formate or hydrogen gas, in a reaction inert solvent. The reduction is conducted in the presence of a palladium catalyst at ambient pressure or under a hydrogen pressure of up to 50 psi. Preferred solvents include $(C_1-C_4)$ alcohols such as methanol and ethanol, and ether solvents such as diethyl ether, dioxane and tetrahydrofuran. The nucleophilic displacement reaction may be conducted by adding the nucleophile directly or by pre-forming the nucleophile separately or in situ from a nucleophile precursor. Preferred nucleophiles include organoaluminum, organoboron, organocopper, organotin, organozinc or Grignard reagent; $R^{29}$—H; or, where $R^{29}$ contains a hydroxyl or thiol group, the anion of $R^{29}$. The term "organo" in the terms organoaluminum, organoboron, organocopper, organotin and organozinc refers to an organic radical selected from $R^{29}$. It will be recognized by those skilled in the art that transition-metal catalysts may be required to effect reaction in certain displacement reactions. When required, such transition metal catalysts may include palladium(0), palladium(II), nickel(0), and nickel(II) complexes. Palladium(II) bis(diphenylphosphinobutane) dichloride is a preferred such catalyst. Additionally, an aqueous or non-aqueous base may be required in the displacement reaction. Preferred such bases include sodium carbonate, sodium hydride, triethylamine and sodium tert-butoxide. The reaction is conducted at ambient pressure in a reaction inert solvent such as a halocarbon, an aromatic or aliphatic hydrocarbon, an ether or a polar aprotic solvent or a combination thereof. In certain cases, a $(C_1-C_4)$alcohol is used as a solvent or co-solvent. The reaction temperature ranges from −20° C. to the reflux temperature of the solvent employed. The reaction time ranges from 1 hour to 3 days.

Compounds of formula 2-6 are prepared by removal of the benzyl protecting group from compounds of formula 2-3 or 2-5. This transformation is accomplished using the freebase, or preferably the pre-formed hydrochloride or similar salt, under standard or transfer hydrogenolysis conditions. The catalysts which may be used in the hydrogenolysis reaction include, but are not limited to, palladium on carbon, palladium hydroxide on carbon and platinum(IV) oxide. The reaction is conducted in a reaction inert solvent, preferably methanol or ethanol and the reaction temperature ranges from room temperature to the reflux temperature of the solvent being employed. The hydrogen source is hydrogen gas, ammonium formate, trialkylammonium formate, or cyclohexene. The reaction time ranges from 15 minutes to 3 days. Generally the reaction is conducted at ambient pressure but pressures of up to 50 psi of hydrogen may be employed. Alternatively, if appropriate, the benzyl protecting group is removed in two steps via chloroformate-induced acylative dealkylation. This involves reaction with a chloroformate derivative to form a carbamate followed by cleavage of the carbamate. While this reaction is preferably conducted with 1-chloroethyl chloroformate and sodium iodide catalysis, it will be recognized by those skilled in the art that catalysis may not be required in certain cases. The reaction is conducted at ambient temperature in a reaction inert solvent such as a halocarbon, an aromatic or aliphatic hydrocarbon, a ketone, an ether or a polar aprotic solvent. The reaction temperature ranges from −78° C. to the reflux temperature of the solvent being employed and the reaction time ranges from 15 minutes to 1 day. Cleavage of the carbamate formed by reaction with 1-chloroethyl chloroformate is accomplished upon exposure to methanol or ethanol at ambient pressure to give compounds of formula 2-6 as a hydrochloride salt. The reaction proceeds at temperatures from room temperature to the reflux temperature of the solvent being employed and the reaction time ranges from 15 minutes to 1 day. Deprotection conditions for other carbamates can be found in Greene, T. W.; Wuts, P. G. M. *Protective Groups in Organic Synthesis*, $2^{nd}$ ed.; John Wiley and Sons Inc.: New York, 1991, pp 315–348.

Compounds of formula 2-7 are prepared from the displacement reaction of amine 2-6 as described in Scheme 1, where the amine 2-6 is equivalent to $R^3$—NH.

Alternatively, compounds of formula 2-7 where $R^{29}$ is as defined above are prepared from compounds of formula 2-3 wherein $R^{29}$ is OH according to the sequence outlined in Scheme 2a below, wherein the conditions are as set forth as described for Scheme 2.

Scheme 2a
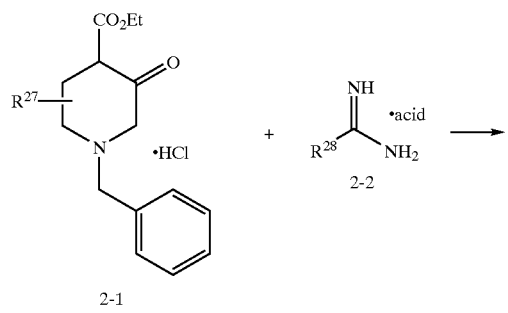
2-1
2-2
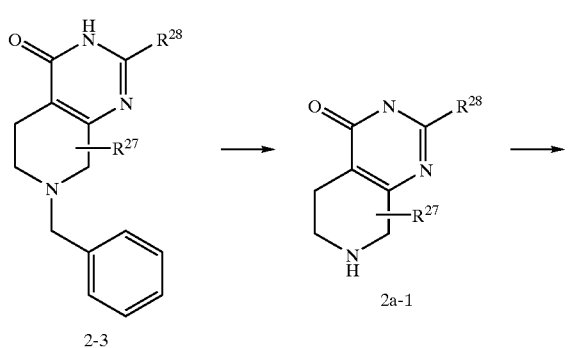
2-3
2a-1
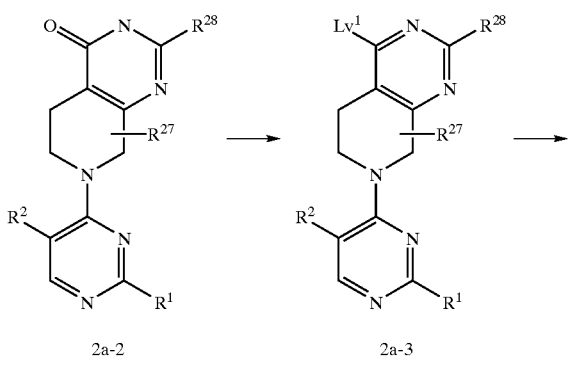
2a-2
2a-3
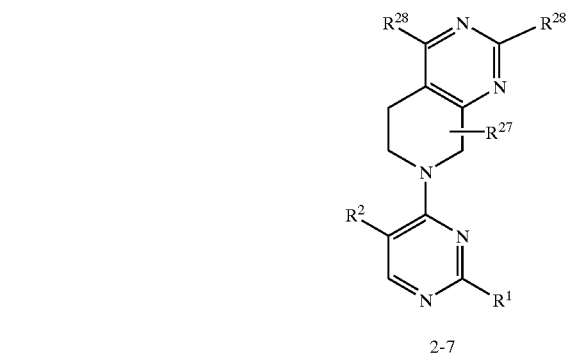
2-7
Compounds of formula 2-2 which are used in Schemes 2 and 2a above are commercially available or are prepared according to methods well known to those skilled in the art, such as those described in March, J. *Advanced Organic Chemistry*, 3$^{rd}$ ed.; John Wiley and Sons.: New York, 1985, p 359, 374.
Scheme 3
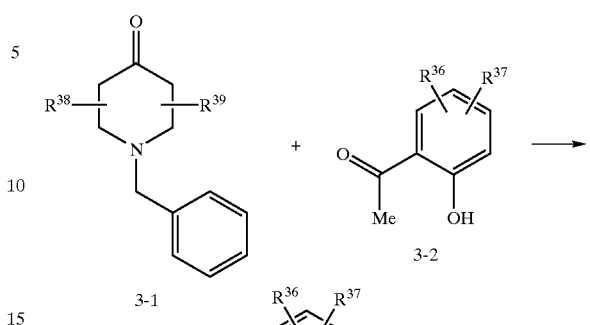
3-1
3-2
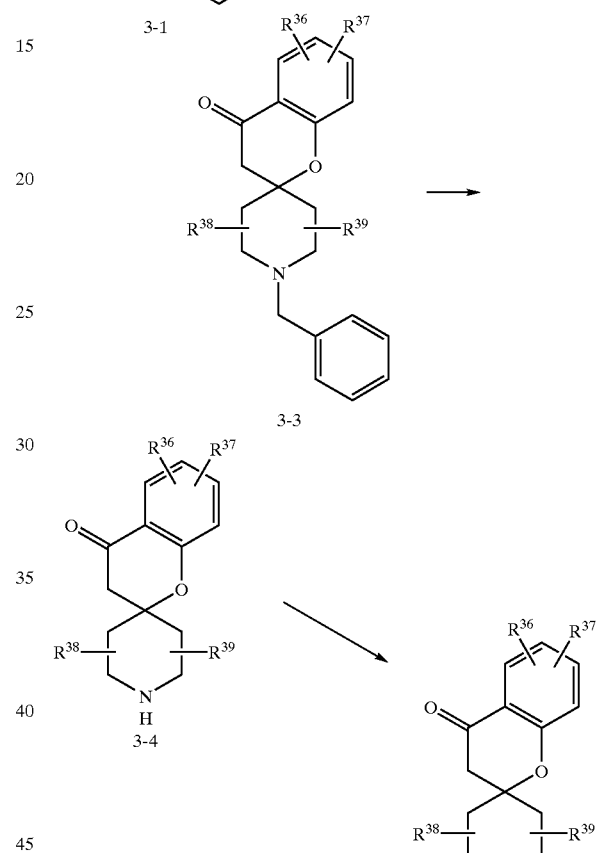
3-3
3-4
3-5
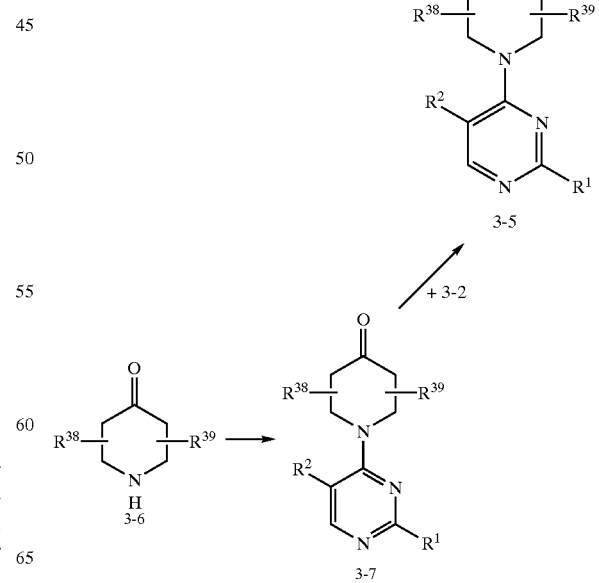
3-6
+ 3-2
3-7

Compounds of formula 3-5 as set forth in Scheme 3 above and more particularly as described below.

Compounds of formula 3-3 are prepared by condensing a compound of formula 3-1 with a compound of formula 3-2. Where R 33 and $R^{39}$ are each H, the compound of formula to the procedure set forth for the preparation of compounds of formula 2-6 above.

Compounds of formula 3-5 are prepared from the displacement reaction of amine 3-4 as described in Scheme 1, where the amine 3-4 is equivalent to $R^3$—NH.

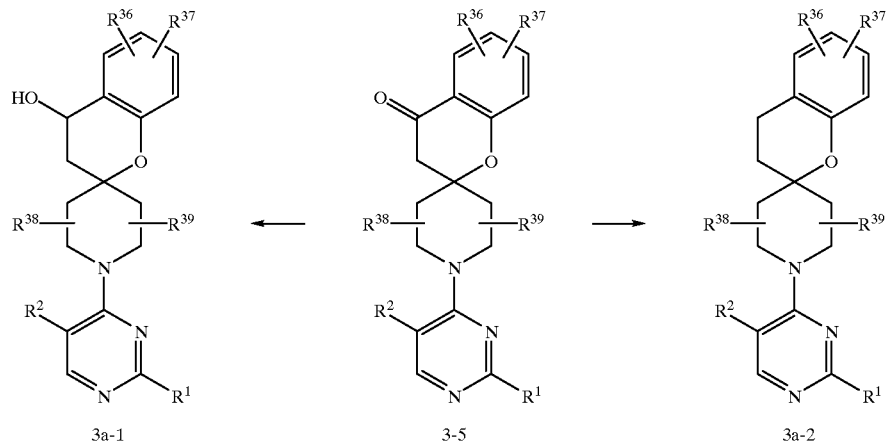

Scheme 3a 3-1 is 1-benzyl-4-piperidone, which is commercially available from Aldrich. Compounds of formula 3-2 are either commercially available or can be prepared according to methods well known to those skilled in the art, particularly according to methods set forth in March, J. *Advanced Organic Chemistry*, $3^{rd}$ ed.; John Wiley and Sons Inc.: New York, 1985, pp 499–500. The reaction is conducted at ambient pressure in the presence of a secondary amine. Generally an excess of the secondary amine, preferably pyrrolidine, piperidine, morpholine or diethylamine, is used. An especially preferred secondary amine is pyrrolidine. The reaction is conducted in a reaction inert solvent, preferably a $(C_1-C_4)$alcohol, an aromatic or aliphatic hydrocarbon, a polar aprotic solvent, a halocarbon or an ether. An especially preferred solvent is ethanol. The reaction time ranges from 2 hours to 3 days and the reaction temperature ranges from ambient temperature to the reflux temperature of the solvent being employed.

Compounds of the formula 3-4 are prepared by removal of the benzyl protecting group from compounds of formula 3-3. This transformation is conducted in a manner analogous Compounds of formulas 3a-1 and 3a-2 are prepared as shown in Scheme 3a from compounds of formula 3-5. Thus, to prepare a compound of 3a-1, a compound of formula 3-5 is reduced with a common reducing agent, such as, for example, sodium borohydride, lithium aluminum hydride or diisobutylaluminum hydride. Other reducing agents capable of effecting the reduction of a ketone to an alcohol are well known to those skilled in the art (e.g., Larock, R. D. *Comprehensive Organic Transformations*, VCH Publishers, Inc.: New York, 1989, pp 527–547). Likewise, compounds of formula 3a-2 are prepared from compounds of formula 3-5 by reduction with reducing agents capable of reducing a ketone completely to a methylene group. A preferred such reducing agent is aluminum trichloride/borane-tert-butylamine complex. Other such reducing agents are well known to those skilled in the art (e.g., *J. Org. Chem.* 1989, 54, 4350; Larock, R. D. Comprehensive Organic Transformations, VCH Publishers, Inc.: New York, 1989, pp 35–37). It will be recognized by those skilled in the art that the transformation of 3-5 to 3a-1 or 3a-2 can be conducted at different points in Scheme 3, depending upon the dynamics of the particular system.

Alternatively, compounds of formula 3-5 wherein $R^{38}$ and $R^{39}$ are hydrogen can be prepared from 4-piperidone monohydrate monochloride in a manner analogous to the procedure described in Scheme 1, where the amine 3-6 is equivalent to $R^3$—NH to give compounds of formula 3-7. Compounds of formula 3-7 can be reacted with compounds of formula 3-2 in a manner analogous to the procedure set forth for the synthesis of compounds of formula 3-3 to afford compounds of formula 3-5.

Scheme 4

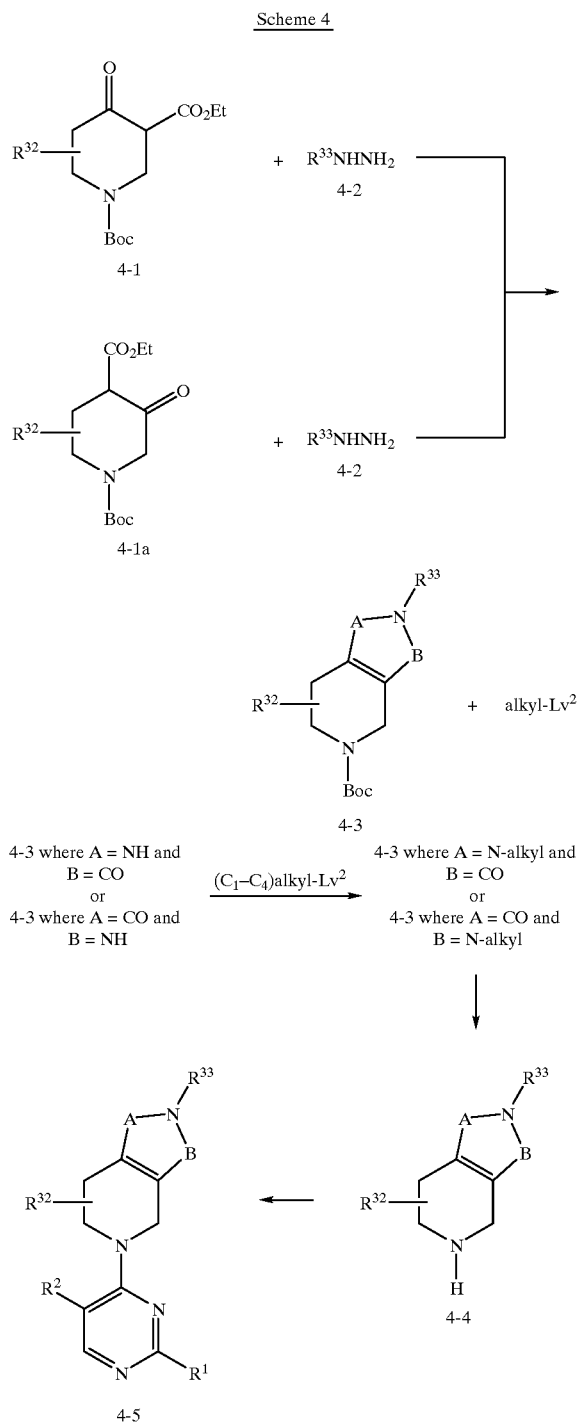

Compounds of formula 4-5 are prepared according to Scheme 4 and more particularly as described below.

Compounds of formula 4-3 are prepared by reacting a compound of formula 4-2 with a compound of formula 4-1 or 4-1a. Compounds of formula 4-1 and 4-1a are prepared according to methods well known to those skilled in the art. Where $R^{32}$ is hydrogen, 4-oxo-piperidine-1,3-dicarboxylic acid 1-tert-butyl ester 3-ethyl ester is condensed with a compound of formula 4-2 to afford a compound of formula 4-3. Said compounds of formula 4-2 are readily available from well known commercial vendors, known in the literature, or are synthesized under standard conditions well known to those skilled in the art. Preferred conditions to prepare compounds of formula 4-3 from a compound of formula 4-1 where A is CO and B is NH or from a compound of formula 4-1a where A is NH and B is CO can be found in March, J. *Advanced Organic Chemistry*, $3^{rd}$ ed.; John Wiley and Sons Inc.: New York, 1985, p 1163. The reaction is conducted at ambient pressure in a reaction inert solvent. Preferred such solvents include aqueous media, a $(C_1-C_4)$ alcohol, glacial acetic acid, an aromatic or aliphatic hydrocarbon, a polar aprotic solvent, a halocarbon and ethers or combinations thereof. The reaction time ranges from 2 hours to 3 days and the reaction temperature ranges from ambient temperature to the reflux temperature of the solvent being used. An optional second step using aqueous or non-aqueous base may be employed in certain cases which will be recognized by those skilled in the art. This second step is conducted at ambient pressure in a reaction inert solvent. Preferred such solvents include aqueous media, a $(C_1-C_4)$alcohol, glacial acetic acid, an aromatic or aliphatic hydrocarbon, a polar aprotic solvent, a halocarbon and ethers or combinations thereof. The reaction time ranges from 2 hours to 3 days and the reaction temperature ranges from ambient temperature to the reflux temperature of the solvent being used.

Compounds of formula 4-3 wherein B is CO and A is N-alkyl or wherein B is N-alkyl and A is CO are prepared by alkylation of compounds of formula 4-3 where B is CO and A is NH or wherein B is NH and A is CO, respectively. The anion of those compounds of formula 4-3 is formed by reaction with an appropriate base. Preferred such bases include sodium hydride and sodium hexamethyldisilazide, although other bases may be used where conditions warrant, as determined by the skilled person. The reaction is conducted in a reaction inert solvent, preferably an ether such as tetrahydrofuran, diethyl ether, dioxane or diglyme or polar aprotic solvent such as dimethylformamide. The reaction proceeds at ambient pressure and at temperatures ranging from −100° C. to ambient temperature. The reaction times are from 10 minutes to 2 hours. Addition of $(C_1-C_4)$alkyl halides or $(C_1-C_4)$alkylsulfonates such as mesylate, tosylate or nosylate to the anion of 4-3 proceeds at ambient pressure and at temperatures ranging from −20° C. to 50 C. The reaction times range from 10 minutes to 1 day.

Compounds of formula 4-4 are prepared form compounds of formula 4-3 wherein A is N-alkyl and B is CO or A is CO and B is N-alkyl via acid-catalyzed deprotection of the Boc carbamate under standard conditions, for example, hydrochloric acid or trifluoroacetic acid in a reaction inert solvent or in the absence of solvent. Such conditions are known to those skilled in the art. Exemplary conditions are disclosed in Greene, T. W.; Wuts, P. G. M. *Protective Groups in Organic Synthesis*, $2^{nd}$ ed.; John Wiley and Sons Inc.: New York, 1991, pp 327–330.

Compounds of formula 4-5 are prepared by the displacement reaction of amine 4-4 as described in Scheme 1, where the amine 4-4 is equivalent to $R^3$—H.

Scheme 5

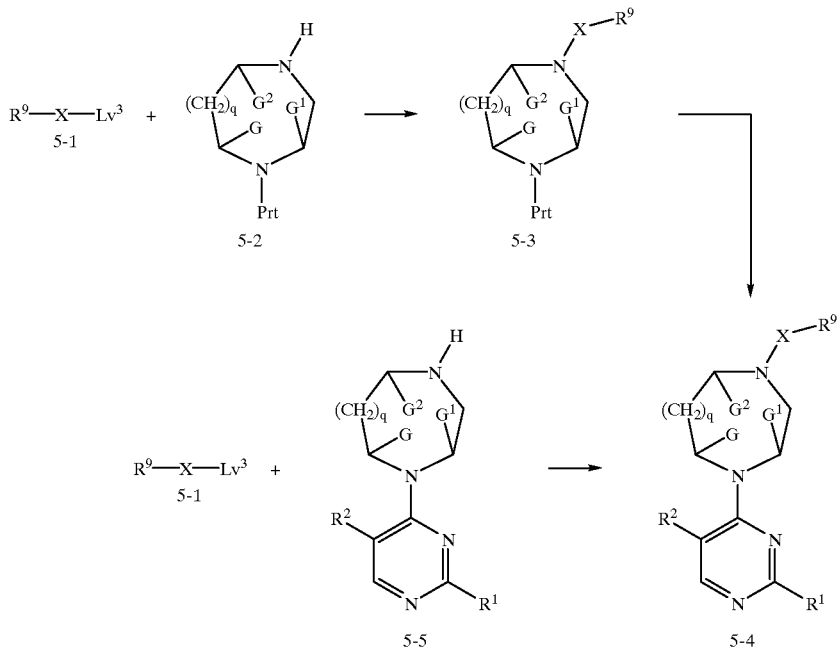

Compounds of formula 5-4 where X is a covalent bond and G, G¹, G², q, R¹, R², R⁶, R⁷ and R⁸ are as defined above are prepared according to Scheme 5 above and particularly as described below.

Compounds of formula 5-3 are prepared by reaction of a compound of formula 5-1 with a compound of formula 5-2 where Prt is an optional amine protecting group selected from benzyl and $CO_2R^{90}$, where $R^{90}$ is selected from $(C_1-C_4)$alkyl, $(C_1-C_4)$allyl, trichloroethyl and benzyl substitutedby up to two $(C_1-C_4)$alkoxy. Compounds of formula 5-1 where $R^9$ is $Ar^1$ and $Lv^3$ is halo, $(C_1-C_4)$alkylsulfide, $(C_1-C_4)$alkylsulfone, trifluoromethanesulfonate, $(C_1-C_6)$ alkylsulfonate or phenylsulfonate, where said phenyl is optionally substituted with up to three halo, nitro or $(C_1-C_4)$ alkyl are commercially available or are readily prepared according to methods well known to those skilled in the art. For example, to prepare compounds of formula 5-1 wherein $Lv^3$ is chloro, a compound of formula $Ar^1$—OH, or the $Ar^1$—(=O) tautomer thereof, is reacted with a chlorinating agent such as phosphorus oxychloride and/or phosphorus pentachloride. This chlorinating reaction is conducted at ambient pressure in the absence of solvent or in a reaction inert solvent, preferably a halocarbon solvent, at temperatures ranging from ambient temperature to 180° C. Treatment of the chloro compound with the requisite mineral acid provides compounds of formula 5-1 where $Lv^3$ is bromo or iodo. Compounds of formula 5-1 wherein $Lv^3$ is trifluoromethanesulfonate, $(C_1-C_6)$alkylsulfonate or phenylsulfonate are prepared from a compound of formula $Ar^1$—OH, or the $Ar^1$—(=O) tautomer thereof, by reaction with a sulfonic acid chloride or anhydride in the presence of a base, preferably an organic amine such as triethylamine, N,N'-diisopropylethylamine, dimethylaminopyridine or pyridine. In certain cases it will be recognized by those skilled in the art that a catalyst will be required to effect reaction. In those cases, a preferred catalyst is 4-dimethylaminopyridine. This reaction is conducted at ambient pressure in a reaction inert solvent such as pyridine, a halocarbon, an aromatic or aliphatic hydrocarbon, an ether, or a combination thereof. The reaction temperature ranges from −20° C. to 100° C. and the reaction time ranges from 15 minutes to 1 day. Compounds of formula 5-1 where $Lv^3$ is thiomethyl are prepared by reacting a compound of formula $Ar^1$—SH, or the $Ar^1$—(=S) tautomer thereof, with methyl iodide or dimethylsulfate in the presence of an inorganic base, preferably potassium carbonate. These reactions are conducted at ambient pressure in a reaction inert solvent, preferably an ether or a polar aprotic solvent. An especially preferred polar aprotic solvent is dimethylformamide at a temperature ranging from 0° C. to 100° C. Compounds of formula 5-1 where $Lv^3$ is methylsulfone are prepared from a compound of formula 5-1 where $Lv^3$ is thiomethyl by oxidation thereof according to procedures well known to those skilled in the art, specifically as set forth in March, J. *Advanced Organic Chemistry*, 3$^{rd}$ ed.; John Wiley and Sons.: New York, 1985, pp 1089–1090.

A representative set of compounds of formula 5-1 which are commercially available or which can be prepared according to methods analogous to a literature procedure include 4-chloropyridine (Aldrich, P.O. Box 355, Milwaukee, Wis. 53201, USA), 3-chloro-6-methyl-pyridazine (Maybridge, c/o Ryan Scientific, 443 Long Point Road, Suite D, Mount Pleasant, S.C. 29464, USA), 2-chloro-pyrazine (Aldrich), 2,6-dichloro-pyrazine (Aldrich), 3-chloro-2,5-dimethylpyrazine (Aldrich), 2,4-dichloro-pyrimidine (Aldrich), 4,6-dichloro-pyrimidine (Aldrich), 4-chloro-2-methyl-pyrimidine (*Chem. Ber.* 1904, 37, 3641), 4-chloro-6-methyl-pyrimidine (Chem. Ber. 1899, 32, 2931), 4-chloro-2,6-dimethyl-pyrimidine (*J. Am. Chem. Soc.* 1946, 68, 1299), 4-chloro-2,6-bis(trifluoromethyl)-pyrimidine (*J. Org. Chem.* 1961, 26, 4504), 4-chloro-2-methylsulfanyl-pyrimidine (Aldrich), 4-chloro-2-methoxymethyl-pyrimidine (U.S. Pat. No. 5,215,990), 1-chloro-isoquinoline (*J. Am. Chem. Soc.* 1946, 68,1299), 2-chloro-quinoline (Aldrich), 4-chloro-quinazoline (*J. Am. Chem. Soc.* 1909, 31, 509), 2-chloro-quinoxaline (U.S. Pat.

No. 2,537,870), 2-chloro-3-methyl-quinoxaline (Aldrich), 2,6,7-trichloro-quinoxaline (*J. Chem. Soc., Chem. Commun.* 1956, 4731), 4-chloro-pteridine (*J. Chem. Soc., Chem. Commun.* 1954, 3832), 7-chloro-pteridine (*J. Chem. Soc., Chem. Commun.* 1954, 3832), and 6-chloro-9H-purine (Aldrich). Other compounds of formula 5-1 can be prepared using methods well known to those skilled in the art or by using methods analogous to those described in the foregoing references.

Compounds of formula 5-3 are prepared by the displacement reaction of a compound of formula 5-1 with an amine of the formula 5-2. The reaction is conducted in the presence of a non-aqueous base, prefeably an organic amine such as pyridine, 4-dimethylaminopyridine, triethylamine or N,N'-diisopropylethylamine; an inorganic base such as potassium or sodium carbonate or bicarbonate; or an alkaline metal alkoxide such as potassium t-butoxide. Alternatively, an excess of the reacting amine 5-2 can be used in lieu of the added base. In cases where the leaving group $Lv^3$ is unactivated, or in specific cases which will be recognized by those skilled in the art, the use of a transition-metal catalyst such as palladium(0), palladium (II), nickel(0) or nickel(II), along with phosphine-based ligands, such as 2,2'-bis(diphenylphosphino)-1,1'-binaphthyl (BINAP), may be required to effect reaction. More specific details concerning this reaction are available in the following references: *J. Org. Chem.* 1997, 62, 1264; *J. Org. Chem.* 1997, 62, 1568; *Syn Lett* 1997, 329. The reaction can be conducted in the absence of solvent or in a reaction inert solvent. Preferable reaction inert solvents include aqueous media, $(C_1-C_4)$ alcohol, $(C_2-C_6)$glycol, a halocarbon, an aliphatic or aromatic hydrocarbon, an ether, a polar aprotic solvent, a ketone, or combinations thereof. The reaction time ranges from 15 minutes to 3 days and the reaction temperature ranges from 0° C. to 180° C. or to the reflux temperature of the solvent being used. The reactions are preferably conducted at ambient pressure.

In certain cases which will be recognized by those skilled in the art, transformations of existing functionality in $Ar^1$ of compound 5-3 may be necessary to produce compounds of formula 5-4. This pertains in particular to those cases where, for example, $R^9$ in 5-3 contains an aromatic or heteroaromatic halide, $(C_1-C_4)$alkylsulfonate or triflate. Said compounds of formula 5-3 wherein $Ar^1$ contains up to two substituents selected from halide, $(C_1-C_4)$alkylsulfonate or triflate, may be converted to a compound of formula $Ar^1$ where said halide, $(C_1-C_4)$alkylsulfonate or triflate is transformed into another functional group by a reduction reaction or by a displacement reaction of said halide, $(C_1-C_4)$ alkylsulfonate or triflate with a nucleophile. The reduction reaction is conducted with a reducing agent, preferably ammonium formate or hydrogen gas, in a reaction inert solvent. The reduction is conducted in the presence of a palladium catalyst at ambient pressure or under a hydrogen pressure of up to 50 psi. Preferred solvents include $(C_1-C_4)$ alcohols such as methanol and ethanol, and ether solvents such as diethyl ether, dioxane and tetrahydrofuran. The nucleophilic displacement reaction may be conducted by adding the nucleophile directly or by pre-forming the nucleophile separately or in situ from a nucleophile precursor. Preferred nucleophiles include organoaluminum, organoboron, organocopper, organotin, organozinc or Grignard reagent; $R^{11}$-oxide or $R^{11}$-thioxide; or anilino where anilino is within the scope of $R^{11}$. It will be recognized by those skilled in the art that transition-metal catalysts may be required to effect reaction in certain displacement reactions. When required, such transition metal catalysts may include palladium(0), palladium(II), nickel(0), and nickel(II) complexes. Palladium(II) bis(diphenylphosphinobutane) dichloride is a preferred such catalyst. Additionally, an aqueous or non-aqueous base may be required in the displacement reaction. Preferred such bases include sodium carbonate, sodium hydride, triethylamine and sodium tert-butoxide. The reaction is conducted at ambient pressure in a reaction inert solvent such as a halocarbon, an aromatic or aliphatic hydrocarbon, an ether or a polar aprotic solvent or a combination thereof. In certain cases, a $(C_1-C_4)$alcohol is used as a solvent or co-solvent. The reaction temperature ranges from −20° C. to the reflux temperature of the solvent employed. The reaction time ranges from 1 hour to 3 days.

Optional protecting groups which may be present in compounds of formula 5-3 are removed according to methods set forth above, or according to methods well known to those skilled in the art, particularly as set forth in: Greene, T. W.; Wuts, P. G. M. *Protective Groups in Organic Synthesis*, $2^{nd}$ ed.; John Wiley and Sons Inc.: New York, 1991.

Compounds of formula 5-4 are prepared from the displacement reaction of amine 5-3 as described in Scheme 1, where the amine 5-3 is equivalent to $R^3$—NH. A representative set of amines of formula 5-3 which are commercially available or which can be prepared by a literature procedure include 1-phenyl-piperazine (Aldrich), 1-pyridin-2-yl-piperazine (Aldrich), 3-piperazin-1-yl-benzo[d]isoxazole (*J. Med. Chem.* 1986, 29, 359), 3-piperazin-1-yl-benzo[d] isothiazole (*J. Med. Chem.* 1986, 29, 359), 2-piperazin-1-yl-quinoxaline (*J. Med. Chem.* 1981, 24, 93), 1-naphthalen-2-yl-piperazine (cf. *Tetrahedron Lett.* 1994, 35, 7331), and 1-(3,5-dimethylphenyl)-piperazine (cf. *Tetrahedron Lett.* 1994, 35, 7331). Other compounds of formula 5-3 can be prepared using methods well known to those skilled in the art or by using methods analogous to those described in the foregoing references.

Alternatively, compounds of formula 5-4 can be prepared from reaction with compounds of formula 5-1 with compounds of formula 5-5 using conditions set forth above to prepare 5-3. Compounds of formula 5-5 can be prepared in a manner analogous to the method used to prepare compounds of formula 1-3.

Compounds of formula 5-4 wherein X is oxycarbonyl, vinylenylcarbonyl, oxy$(C_1-C_4)$alkylenylcarbonyl, $(C_1-C_4)$ alkylenylcarbonyl, $(C_3-C_4)$alkenylcarbonyl, thio$(C_1-C_4)$ alkenylcarbonyl, vinylenylsulfonyl or carbonyl$(C_0-C_4)$ alkylenylcarbonyl; wherein said oxy$(C_1-C_4)$ alkylenylcarbonyl, $(C_1-C_4)$alkylenylcarbonyl, $(C_3-C_4)$ alkenylcarbonyl, and thio$(C_3-C_4)$alkenylcarbonyl in the definition of X are each optionally and independently substituted with up to two $(C_1-C_4)$alkyl, benzyl, or Ar; said vinylenylsulfonyl and said vinylenylcarbonyl in the definition of X are each optionally and independently substituted with up to three $(C_1-C_4)$alkyl, benzyl, or Ar are also prepared according to Scheme 5 above and particularly as described below.

Compounds of formula 5-4 where X is as defined in the immediately preceding paragraph are prepared by reacting a compound of formula 5-5 with a compound of formula 5-1 where $R^9$ is described above, X is as defined in the immediately preceding paragraph and $Lv^3$ is chloro. The reaction is conducted under anhydrous conditions in the presence of a non-aqueous base, which includes organic amines such as triethylamine, N,N'-diisopropylethylamine and pyridine and derivatives thereof. The reaction is generally conducted in a reaction inert solvent. Preferred solvents include halocarbon, aliphatic or aromatic hydrocarbon, ethers, ethyl acetate, pyridine and combinations thereof. The reaction time ranges from 15 minutes to 24 hours and the reaction temperature ranges from 0° C. to 80° C. or to the reflux temperature of the solvent being used. The reactions are preferably conducted at from 0° C. to ambient temperature and at ambient pressure. Removal of optional protecting groups is carried out as described in Scheme I.

Compounds of formula 5-4 wherein X is vinylenylcarbonyl, oxy($C_1$–$C_4$)alkylenylcarbonyl, ($C_1$–$C_4$) alkylenylcarbonyl, ($C_3$–$C_4$)alkenylcarbonyl, thio($C_2$–$C_4$) alkenylcarbonyl, or carbonyl($C_0$–$C_4$)alkylenylcarbonyl; wherein said oxy($C_1$–$C_4$)alkylenylcarbonyl, ($C_1$–$C_4$) alkylenylcarbonyl, ($C_3$–$C_4$)alkenylcarbonyl, and thio ($C_2$–$C_4$)alkenylcarbonyl in the definition of X are each optionally and independently substituted with up to two ($C_1$–$C_4$)alkyl, benzyl, or Ar; and said vinylenylcarbonyl in the definition of X are each optionally and independently substituted with up to three ($C_1$–$C_4$)alkyl, benzyl, or Ar are also prepared according to Scheme 5 avove and particularly as described below.

Compounds of formula 5-4 are prepared by reacting a compound of formula 5-5 with a compound of formula $R^9$—X—$Lv^3$ where $R^9$ is described above, X is as defined in the immediately preceding paragraph and $Lv^3$ is OH. The reaction is conducted in the presence of coupling agents, preferably dicyclohexylcarbodiimide or 1-(3-dimethylaminopropyl)-3-ethylcarbodiimide hydrochloride as described in *J. Amer. Chem. Soc.* 1996, 118, 4952. The reaction is conducted in a reaction inert solvent. Preferred solvents include halocarbon, aliphatic or aromatic hydrocarbon and ethers. Especially preferred solvents include dichloromethane and chloroform. Other coupling agents that can be used are well known to those skilled in the art and include, but are not limited to, various phosphine reagents, ethyl chloroformate, and N-hydroxysuccinimide. These reagents and procedures are described in "Compendium of Organic Synthetic Methods" (Ed., I. T. Harrison and S. Harrison, John Wiley & Sons). Specific references include the following: *J. Org. Chem,* 1971, 36,1305; *Bull. Soc. Chim. Fr.,* 1971, 3034; *Bull. Chem. Soc. Japan,* 1971, 44,1373; *Tetrahedron Lett.,* 1973, 28,1595; *Tetrahedron Lett.,* 1971, 26, 2967, and *J. Med. Chem.,* 1968, 11, 534. Removal of optional protecting groups is carried out as described in Scheme I.

Compounds of formula 5-4 wherein X is a covalent bond and $R^9$ is ($C_3$–$C_7$)cycloalkyl or $Ar^1$—($C_1$–$C_3$)alkylenyl are also prepared according to Scheme 5 above and particularly as described below.

Compounds of formula 5-4 wherein X is a covalent bond and $R^9$ is ($C_3$–$C_7$)cycloalkyl or $Ar^1$—($C_1$–$C_3$)alkylenyl are prepared by reacting a compound of formula 5-1 wherein X is a covalent bond, $R^9$ is ($C_3$–$C_7$)cycloalkyl or $Ar^1$—($C_1$–$C_3$)alkylenyl and $Lv^3$ is halo, methanesulfonate, p-toluenesulfonate or trifluoromethanesulfonate. The reaction is conducted under anhydrous conditions in the presence of a non-aqueous base, which includes organic amines such as triethylamine, N,N'-diisopropylethylamine and pyridine and derivatives thereof. The reaction is conducted in a reaction inert solvent. Preferred solvents for the reaction include halocarbons, aliphatic or aromatic hydrocarbons, ethers, ethyl acetate, pyridine and combinations thereof. The reaction time ranges from 15 minutes to 24 hours and the reaction temperature ranges from –20° C. to 80° C. or to the reflux temperature of the solvent being used. The reactions are preferably conducted at ambient temperature of the solvent being used and at ambient pressure. Removal of optional protecting groups is conducted as set forth in Scheme I.

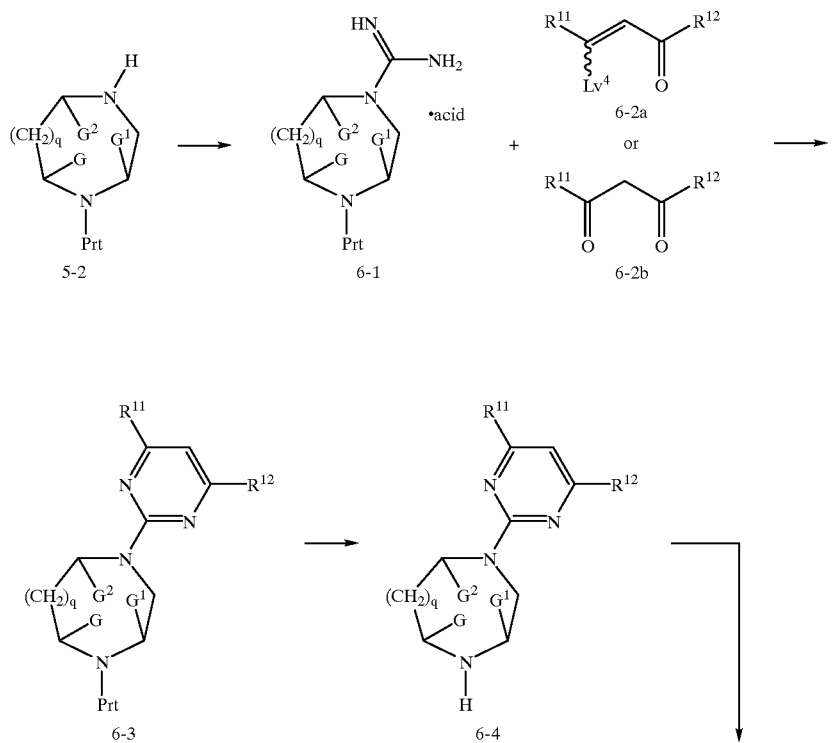

Scheme 6

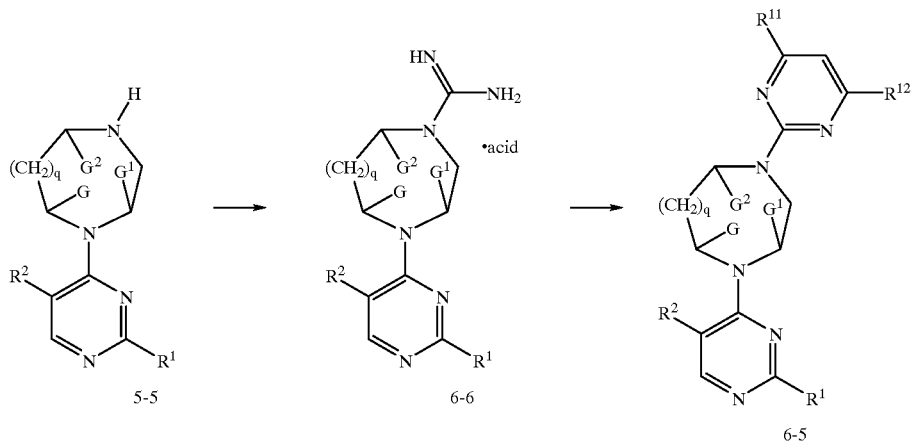

Compounds of formula 6-5 wherein G, $G^1$, $G^2$, q, $R^1$, $R^2$, $R^6$, $R^7$ and $R^8$ are as defined above are prepared as set forth in Scheme 6 above and particularly as described below.

Compounds of formula 6-1 are prepared from an amine of the formula 5-2 where Prt is an optional amine protecting group selected from benzyl and $CO_2R^{90}$, where $R^{90}$ is selected from $(C_1–C_4)$alkyl, $(C_1–C_4)$allyl, trichloroethyl and benzyl substituted with up to two $(C_1–C_4)$alkoxy. The preferred procedure for preparing compounds of formula 6-1 can be found in *Tetrahedron Lett*. 1993, 48, 7767 or *J. Org. Chem* 1997, 62, 1540.

Compounds of formula 6-3 are prepared by condensation of β-diketones or β-ketoesters of the formula 6-2b, where $R^{11}$ and $R^{12}$ are independently substituted as set forth above, or compounds of the formula 6-2a where $Lv^4$ is, for example, hydroxy, chloro or dimethylamino with guanidines of the formula 6-1. The reaction is conducted in the presence of an aqueous or non-aqueous base, preferably potassium or sodium hydroxide, potassium or sodium $(C_1–C_4)$-alkoxide, triethylamine, pyridine, 4-dimethylaminopyridine, potassium or sodium carbonate or potassium or sodium bicarbonate. The reaction is conducted in a reaction inert solvent, preferably aqueous media, a $(C_1–C_4)$alcohol, a $(C_2–C_6)$ dialcohol, an aromatic hydrocarbon, a polar aprotic solvent, or combinations thereof. The reaction time ranges from 2 hours to 3 days and the reaction temperature ranges from room temperature to reflux of the solvent employed. The reaction is preferably run at ambient pressure, but may be conducted at pressures up to 250 psi.

Removal of of optional protecting groups in compounds of formula 6-3 to afford compounds of formula 6-4 is accomplished as set forth above.

Compounds of formula 6-5 are prepared from the displacement reaction of amine 6-4 as described in Scheme 1, where the amine 6-4 is equivalent to $R^3$—NH.

Alternatively, compounds of formula 6-5 are prepared from compounds of formula 5-5 by formation of a compound of formula 6-6, or by reaction with compounds of formula 6-2a or 6-2b under the conditions outlined above in Scheme 6. Removal of optional protecting groups is conducted as described in Scheme 1. Compounds of formula 5-5 are prepared as set forth above.

Scheme 7

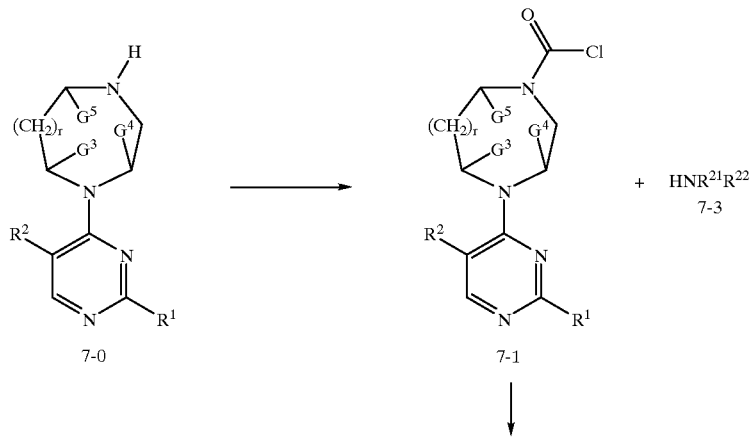

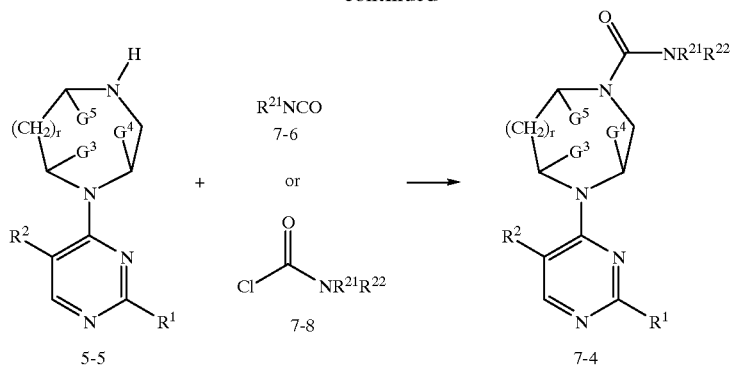

Compounds of formula 7-4 wherein $G^3$, $G^4$, $G^5$, r, $R^1$, $R^2$, $R^{18}$, $R^{19}$ and $R^{20}$ are defined as set forth above are prepared as set forth in Scheme 7 and particularly as described below.

Compounds of formula 7-1 are prepared by reaction of an amine of the formula 7-0 with phosgene or a phosgene equivalent such as triphosgene. Compounds of 7-1 wherein the chloro group is replaced by an imidazolyl group are also useful in this reaction. Such compounds are prepared by reaction of an amine of formula 7-0 with carbonyl diimidazole. The reaction is conducted under anhydrous conditions in the presence of a nonaqueous base. Preferred such bases include triethylamine and other tertiary amines and pyridine and derivatives thereof. The reaction is conducted in a reaction inert solvent at −78° C. to 80° C. or at the reflux temperature of the solvent being used for 15 minutes to 24 hours. Preferred solvents for this reaction include a halocarbon, an aliphatic or aromatic hydrocarbon, an ether, ethyl acetate, pyridine and combinations thereof. The reactions are preferably conducted at from 0° C. to ambient temperature and at ambient pressure.

Compounds of formula 7-4 are prepared by reaction of carbamoyl chlorides of the formula 7-1 with amines of the formula 7-3, where $R^{21}$ and $R^{22}$ are defined above. The reaction can be conducted in the absence of solvent, or in a reaction inert solvent. Preferred such solvents include aqueous media, a $(C_1-C_4)$alcohol, a $(C_2-C_6)$dialcohol, an aromatic or aliphatic hydrocarbon, a halocarbon, an ether, a polar aprotic solvent, a ketone, pyridine or combinations thereof. The reaction time ranges from 15 minutes to 3 days and the reaction temperature ranges from 0° C. to the reflux temperature of the solvent being used. The reaction is preferably conducted at ambient pressure. It will be recognized by those skilled in the art that addition of a base may be required to effect reaction. In those cases, preferred bases include potassium or sodium hydroxide, triethylamine and other tertiary amines, pyridine and its derivatives and inorganic bases such as sodium or potassium carbonate and sodium or potassium bicarbonate. Removal of optional hydroxyl protecting groups contained in $R^1$ is carried out according to methods set forth in Scheme 1.

Alternatively, compounds of formula 7-4 are prepared from compounds of formula 7-0 by reaction with isocyanates of the formula 7-6 or with carbamoyl chlorides of the formula 7-8. Said isocyanates are commercially available, known in the literature, or synthesized under standard conditions known to those skilled in the art, particularly as described in March, J. *Advanced Organic Chemistry*, $3^{rd}$ ed.; John Wiley and Sons Inc.: New York, 1985, p 1166. A preferred method of forming such isocyanates is the Curtius rearrangement of a suitable acyl azide. Said carbamoyl chlorides are synthesized using methods analogous to that described for the preparation of compounds of formula 7-1 in Scheme 7. Removal of optional hydroxyl protecting groups contained in $R^1$ is carried out according to methods set forth in Scheme 1.

Compounds of formula I containing the radical $R^{3c}$ are prepared according to the procedures set forth in Scheme 7 using the corresponding starting materials and reagents.

Scheme 8

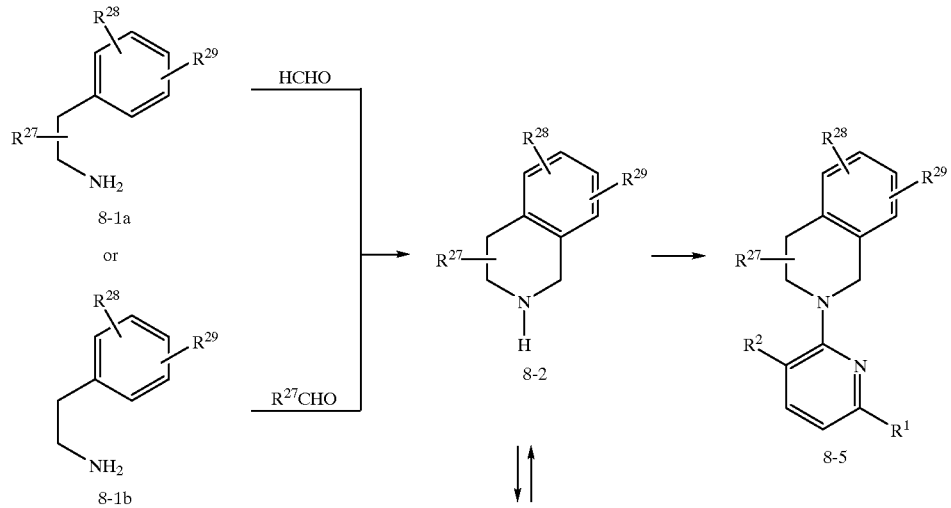

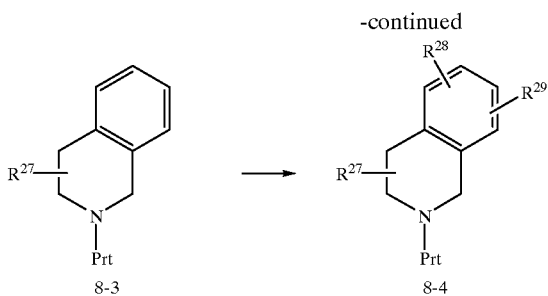

Compounds of formula 8-5 are prepared as set forth in Scheme 8 and particularly as described below.

Compounds of formula 8-2 are readily prepared from commercially available phenethylamines of formula 8-1a and formaldehyde or an aldehyde of the formula $R^{27}$—CHO under Pictet-Spengler conditions. The Pictet-Spengler reaction is reviewed in *Chem. Rev.* 1995, 95,1797. A similar route route to 1,2,3,4-tetrahydroisoquinolines using the Bischler-Napieralski reaction, as disclosed in March, *J. Advanced Organic Chemistry*, $3^{rd}$ ed.; John Wiley and Sons.: New York, 1985, 495, followed by standard reduction of the imine formed may also be employed.

Compounds of formula 8-4 are prepared from compounds of formula 8-3 by aromatic electrophilic substitution using the appropriate electrophile. A general reference for this type of reaction can be found in March, J. *Advanced Organic Chemistry*, $3^{rd}$ ed.; John Wiley and Sons.: New York, 1985, 447–511.

Compounds of formula 8-2 are also prepared by removal of the protecting group from a compound of formula 8-4. Preferably the protecting group is trifluoroacetamide which may be removed under basic conditions using inorganic hydroxides or carbonates in a reaction inert solvent. Suitable such solvents include $(C_1-C_4)$alcohols and preferably methanol. Optionally, one or more co-solvents, preferably selected from water, tetrahydrofuran and dioxane may be employed. The reaction time ranges from 15 minutes to 24 hours and the reaction temperature ranges from 0° C. to 100° C. or to the reflux temperature of the solvent or solvent system being used. The reaction is preferably conducted at ambient temperature. Other conditions for deprotection of trifluoroacetamides and deprotection conditions for other suitable protecting groups can be found in Greene, T. W.; Wuts, P. G. M. *Protective Groups in Organic Synthesis*, $2^{nd}$ ed.; John Wiley and Sons Inc.: New York, 1991.

Compounds of formula 8-4 are prepared by adding a protecting group to compounds of formula 8-2. Preferably the protecting group is trifluoroacetamide or tert-butoxycarbonyl (BOC). The protecting group is attached by reaction of a compound of formula 8-2 with trifluoroacetyl chloride or di-tert-butyl dicarbonate or an equivalent thereof in the presence of a base, preferably triethylamine or pyridine. The reaction is conducted in a reaction inert solvent. Preferred such solvents include ethers such as tetrahydrofuran, diethyl ether, dioxane or dimethoxyethane; a halocarbon such as dichloromethane, chloroform or carbon tetrachloride; and aromatic or aliphatic hydrocarbons such as benzene, toluene or hexanes. The reaction time ranges from 15 minutes to 3 days and the reaction temperature ranges from 0° C. to the reflux temperature of the solvent being used. The reaction is preferably conducted at ambient pressure. Other conditions for protection of amines with trifluoroacetamides or tert-butoxycarbonyl groups as well as other suitable protecting groups can be found in Greene, T. W.; Wuts, P. G. M. *Protective Groups in Organic Synthesis*, $2^{nd}$ ed.; John Wiley and Sons Inc.: New York, 1991.

Manipulation of the substituents $R^{28}$ and $R^{29}$ is carried out to provide isoquinolines with altered substitution. Preferably, transition metal-catalyzed cross-coupling of a compound of formula 8-4 where $R^{28}$ or $R^{29}$ is bromide or triflate is employed to afford compounds of formula 8-4 wherein $R^{28}$ or $R^{29}$ are as set forth above. This reaction is conducted according to methods well known to those skilled in the art, particularly as set forth in *Tetrahedron*, 1998, 54, 263 for Stille and Suzuki Reactions and in *Acc. Chem. Res.* 1998, 31, 805 for Buchwald Amination Reactions.

Compounds of formula 8-5 are prepared from the displacement reaction of amine 8-2 as described in Scheme 1, where the amine 8-2 is equivalent to $R^3$—NH.

Scheme 9

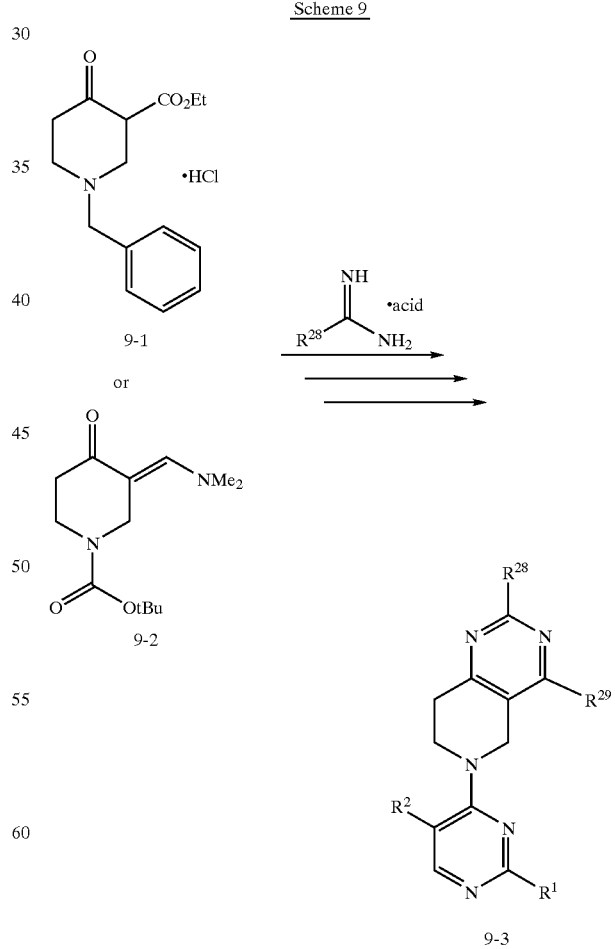

Compounds of formula 9-3 are prepared according to the general procedures set forth in Scheme 2 starting from ethyl 1-benzyl-4-oxo-3-piperidine carboxylate hydrochloride (9-1). In certain cases, where $R^{29}$ is H, N-tertbutoxycarbonyl-3-(dimethylaminomethylene)-4-piperidone (9-2, Chemical Abstracts 121:157661) is used as the starting material.

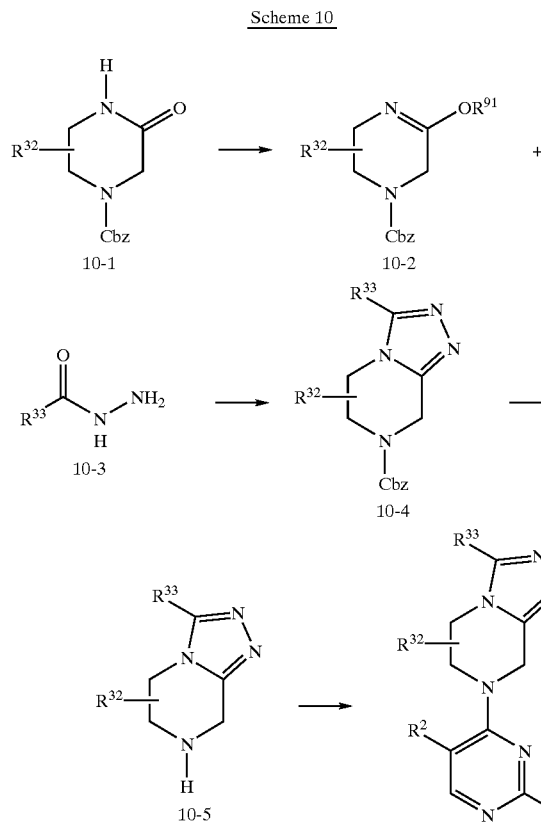

Scheme 10

Compounds of formula 10-6 wherein $R^1$, $R^2$, $R^{32}$ and $R^{33}$ are as defined above are prepared as set forth in Scheme 10 and more particularly as described below.

Compounds of formula 10-2 where $R^{91}$ is $(C_1-C_4)$alkyl are prepared by reacting a compound of formula 10-1, where Cbz is benzyloxycarbonyl, with an 0-alkylating agent. A preferred compound of formula 10-1 is 3-oxo-piperazine-1-carboxylic acid benzyl ester. A preferred O-alkylating agent is triethyloxonium tetrafluoroborate. The reaction is conducted at ambient pressure in a reaction inert solvent. Preferred solvents include an aromatic or aliphatic hydrocarbons, halocarbons and ethers. Dichloromethane is especially preferred. The reaction time ranges from 2 hours to 3 days and the reaction temperature ranges from –100° C. to ambient temperature.

Compounds of formula 10-4 are prepared by condensation of a compound of formula 10-2 with a compound of formula 10-3. Said compounds of formula 10-3 are commercially available, are known in the literature, or are readily prepared via standard amidation of hydrazine and an activated carboxylic acid, such as a carboxylic acid chloride. Such reactions are well known by those skilled in the art. The condensation reaction is preferably run at ambient pressure, although higher pressures up to 250 psi may be employed if necessary. The reaction is conducted in a reaction inert solvent, preferably selected from $(C_1-C_4)$ alcohols, aromatic or aliphatic hydrocarbons, polar aprotic media, halocarbons and ethers, or combinations thereof. The reaction is conducted at temperatures ranging from ambient temperature to 180° C. The reaction times are from 2 hours to 3 days.

Compounds of formula 10-5 are prepared form compounds of formula 10-4 via Lewis acid-catalyzed cleavage or hydrogenolysis of the Cbz carbamate under standard conditions which are well known to those skilled in the art, particularly as set forth in Greene, T. W.; Wuts, P. G. M. *Protective Groups in Organic Synthesis*, 2$^{nd}$ ed.; John Wiley and Sons Inc.: New York, 1991, pp 335–338.

Compounds of formula 10-6 are prepared from the displacement reaction of an amine of the formula 10-5 as described in Scheme 1, where the amine 10-5 is equivalent to $R^3$—NH.

Scheme 11

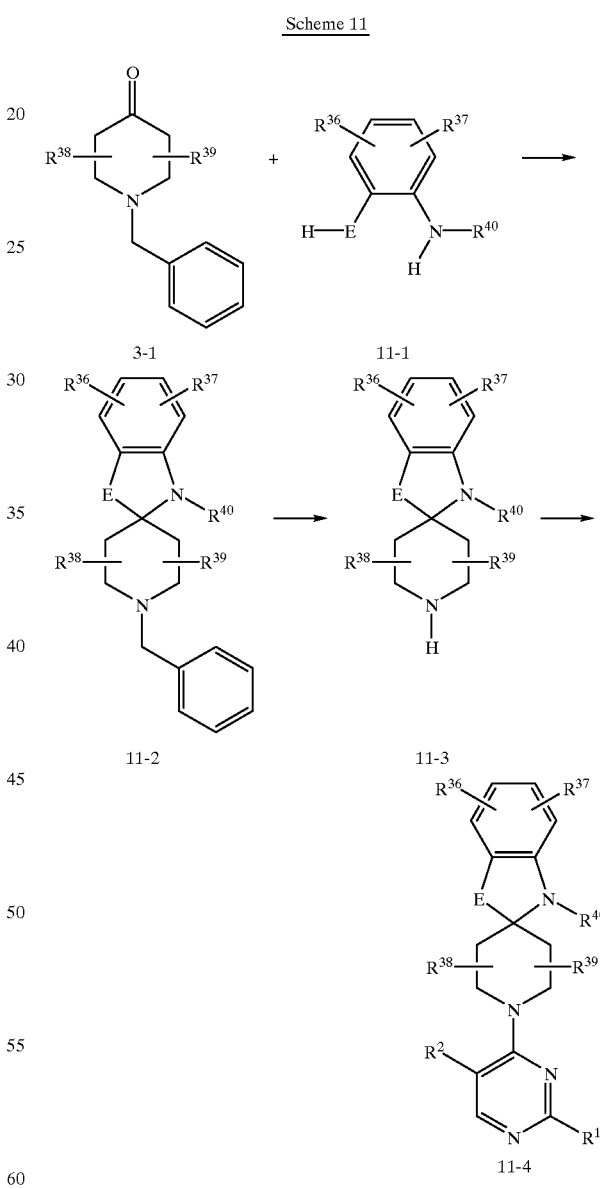

Compounds of formula 11-4, wherein $R^1$, $R^2$, $R^{36}$, $R^{37}$, $R^{38}$, $R^{39}$ and $R^{40}$ are as defined above are prepared as set forth in Scheme 11 and more particularly as described below.

Where $R^{38}$ and $R^{39}$ are hydrogen, 1-benzyl-4-piperidone (3-1), available from Aldrich, is condensed with a compound of formula 11-1, which are either commercially available or well known to those skilled in the art, to give compounds of formula 11-2. Where $R^{38}$ and $R^{39}$ are not hydrogen, compounds of formula 3-1 can be prepared according to methods well known to those skilled in the art. The reaction is conducted at ambient pressure in the absence of solvent or in a reaction inert solvent. Preferred solvents include $(C_1-C_4)$alcohols, aromatic or aliphatic hydrocarbons, polar aprotic solvents, halocarbons and ethers. The reaction time ranges from 2 hours to 3 days and the reaction temperature ranges from ambient temperature to the reflux temperature of the solvent being employed. More specific conditions can be found in *Indian J. Chem.* 1976, 14B, 984 and *J. Chem. Soc., Perkin Trans.* 1 1984, 2465.

Compounds of formula 11-3 are prepared by removal of the benzyl protecting group from a compound of formula 11-2 in a manner analogous to the method employed for the preparation of compounds of 2-6 described above.

Compounds of formula 11-4 are prepared by the displacement reaction of an amine of the formula 11-3 as described in Scheme 1, where the amine 11-3 is equivalent to $R^3$—H.

Scheme 12

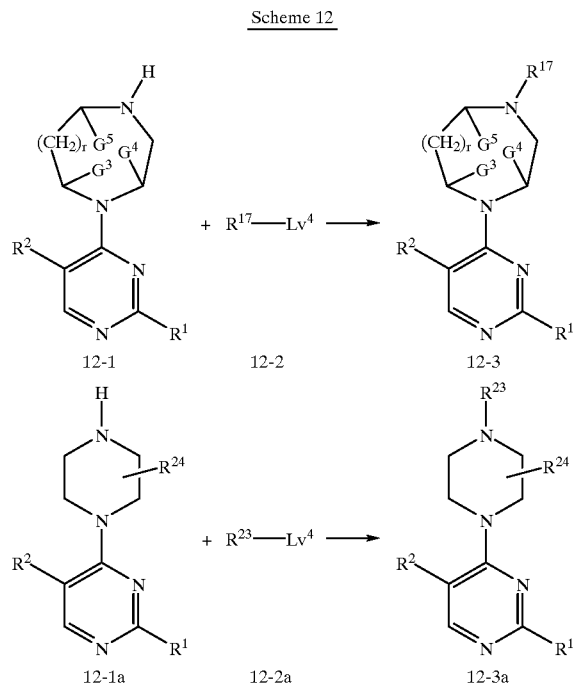

Compounds of formula 12-3 and 12-3a where $R^{17}$ and $R^{23}$ are $(C_1-C_6)$alkoxycarbonyl, $(C_1-C_6)$alkylcarbonyl, $Ar^2$-carbonyl, $(C_1-C_6)$alkylsulfonyl, $Ar^2$-sulfonyl, or $Ar^2$-sulfinyl are prepared according to Scheme 12 above and particularly as set forth below.

Compounds of formula 12-3 and 12-3a where $R^{17}$ and $R^{23}$ are as defined in the immediately preceding paragraph are prepared by condensation with a compound of formula 12-2 and 12-2a, wherein $Lv^4$ is chloro, respectively. Examples of compounds of formula 12-2 and 12-2a include $(C_1-C_6)$alkoxyCOCl, $(C_1-C_6)$alkylCOCl, $Ar^2$—COCl, $(C_1-C_6)$alkylSO$_2$Cl, $Ar^2$—SO$_2$Cl, or $Ar^2$—SOCl. The reaction is conducted under anhydrous conditions in the presence of a non-aqueous base, which includes organic amines such as triethylamine, N,N'-diisopropylethylamine and pyridine and derivatives thereof. The reaction is conducted in a reaction inert solvent. Preferred solvents for the reaction include halocarbon, aliphatic or aromatic hydrocarbon, ethers, ethyl acetate, pyridine and combinations thereof. The reaction time ranges from 15 minutes to 24 hours and the reaction temperature ranges from 0° C. to 80° C. or to the reflux temperature of the solvent being used. The reactions are preferably conducted at from 0 C. to ambient temperature and at ambient pressure. Removal of optional protecting groups is carried out as described in Scheme I.

Compounds of formula 12-3 and 12-3a wherein $R^{17}$ and $R^{23}$ are $(C_1-C_6)$alkylcarbonyl or $Ar^2$-carbonyl are also prepared according to Scheme 12 above and particularly as described below.

Compounds of formula 12-3 and 12-3a wherein $R^{17}$ and $R^{23}$ are $(C_1-C_6)$alkylcarbonyl or $Ar^2$-carbonyl are prepared by a condensation reaction with a compound of formula 12-2 or 12-2a, respectively, wherein $Lv^4$ is hydroxy in the presence of coupling agents such as dicyclohexylcarbodiimide or 1-(3-dimethylaminopropyl)-3-ethylcarbodiimide hydrochloride. The reaction is conducted in a reaction inert solvent. Preferred solvents include halocarbon, aliphatic/aromatic hydrocarbons and ethers. Especially preferred solvents include dichloromethane and chloroform. Other coupling agents that can be used are well known to those skilled in the art and include, but are not limited to, various phosphine reagents, ethyl chloroformate, and N-hydroxysuccinimide. Removal of optional protecting groups is carried out as described in Scheme I.

Compounds of formula 12-3 where $R^{17}$ is $(C_1-C_6)$alkyyl are also prepared according to Scheme 12 and particularly as described below.

Compounds of formula 12-3 where $R^{17}$ is $(C_1-C_6)$alkyl are prepared by reacting a compound of formula 12-1 with a compound of formula 12-2 where $R^{17}$ is $(C_1-C_4)$alkyl and $Lv^4$ is Cl, Br, I, methanesulfonyloxy, p-toluenesulfonyloxy or trifluoromethanesulfonyloxy. The reaction is conducted under anhydrous conditions in the presence of a nonaqueous base, which includes organic amines such as triethylamine, Hunig's base and pyridine and derivatives thereof. The reaction is conducted in a reaction inert solvent. Preferred solvents for the reaction include halocarbons, aliphatic or aromatic hydrocarbons, ethers, ethyl acetate, pyridine and combinations thereof. The reaction time ranges from 15 minutes to 24 hours and the reaction temperature ranges from ambient temperature to 80° C. or to the reflux temperature of the solvent being used. The reactions are preferably conducted at ambient temperature and pressure.

The starting materials and reagents for the above described compounds are also readily available or can be easily synthesized by those skilled in the art using conventional methods of organic synthesis. For example, many of the compounds used herein are related to, or are derived from, compounds found in nature, in which there is a large scientific interest and commercial need, and accordingly many such compounds are commercially available or are reported in the literature or are easily prepared from other commonly available substances by methods which are reported in the literature.

The compounds of the instant invention inhibit the formation of sorbitol dehydrogenase and as such have utility in the treatment of diabetic complications including but not limited to such complications as diabetic nephropathy, diabetic neuropathy, diabetic retinopathy, diabetic microangiopathy and diabetic macroangiopathy and diabetic cardiomyopathy. The utility of the compounds of the present invention as medical agents in the treatment of diseases, such as are detailed herein in mammals (e.g., humans) for example, diabetic complications such as diabetic cardiomyopathy, diabetic neuropathy, diabetic nephropathy, diabetic retinopathy, diabetic microangiopathy and diabetic macroangiopathy is demonstrated by the activity of the compounds of formula I of this invention in conventional assays. Such assays also provide a means whereby the activities of the compounds of formula I of this invention can be compared with the activities of other known compounds. The results of these comparisons are useful for determining dosage levels in mammals, including humans, for the treatment of such diseases.

Measurement of SDH Activity

Male Sprague-Dawley rats (350-400 g) are used for these experiments. Diabetes is induced in some of the rats by a tail vein injection of streptozocin, 85 mg/kg. Twenty-four hours later, 4 groups of diabetic rats are given a single dose of the test compound of formula I of this invention (0.001 to 100 mg/kg) by oral gavage. Animals are sacrificed 4–6 hours after dosing and blood and sciatic nerves are harvested. Tissues and cells are extracted with 6% perchloric acid.

Sorbitol in erythrocytes and nerves is measured by a modification of the method of R. S. Elements et al. (Science, 166: 1007–8, 1969). Aliquots of tissue extracts are added to an assay system which has final concentrations of reagents of 0.033 M glycine, pH 9.4, 800 mM B-nicotine adenine dinucleotide, and 4 units/ml of sorbitol dehydrogenase. After incubation for 30 minutes at room temperature, sample fluorescence is determined on a fluorescence spectrophotometer with excitation at 366 nm and emission at 452 nm. After subtracting appropriate blanks, the amount of sorbitol in each sample is determined from a linear regression of sorbitol standards processed in the same manner as the tissue extracts.

Fructose is determined by a modification of the method described by M. Ameyama, *Methods in Enzymology*, 89: 20–25 (1982). Resazurin is substituted for ferricyanide. Aliquots of tissue extracts are added to the assay system, which has final concentrations of reagents of 1.2 M citric acid, pH 4.5, 13 mM resazurin, 3.3 units/ml of fructose dehydrogenase and 0.068% Triton X-100. After incubation for 60 minutes at room temperature, sample fluorescence is determined on a fluorescence spectrophotometer with excitation at 560 nm and emission at 580 nm. After subtracting appropriate blanks, the amount of fructose in each sample is determined from a linear regression of fructose standards processed in the same manner as the tissue extracts.

SDH activity is measured by a modification of the method described by U. Gerlach, *Methodology of Enzymatic Analyses*, edited by H. U. Bergmeyer, 3, 112–117 (1983). Aliquots of sera or urine are added to the assay system, which has final concentrations of reagents of 0.1 M potassium phosphate buffer, pH 7.4, 5 mM NAD, 20 mM sorbitol, and 0.7 units/ml of sorbitol dehydrogenase. After incubation for 10 minutes at room temperature, the average change in sample absorbance is determined at 340 nm. SDH activity was presented as milliOD$_{340}$ units/minute (OD$_{340}$=optical density at 340 nm).

The expression "pharmaceutically acceptable salts" includes both pharmaceutically acceptable acid addition salts and pharmaceutically acceptable cationic salts, where appropriate. The expression "pharmaceutically-acceptable cationic salts" is intended to define but is not limited to such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, ethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. The expression "pharmaceutically-acceptable acid addition salts" is intended to define but is not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

Pharmaceutically acceptable salts of the second pharmaceutical agents of this invention may be readily prepared by reacting the free acid form of said second pharmaceutical agent with an appropriate base, usually one equivalent, in a cosolvent. Typical bases are sodium hydroxide, sodium methoxide, sodium ethoxide, sodium hydride, potassium methoxide, magnesium hydroxide, calcium hydroxide, benzathine, choline, ethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), and employing a solvent (e.g., ethyl acetate) from which the desired cationic salt precipitates, or can be otherwise isolated by concentration and/or addition of a non-solvent.

The acid addition salts of the second pharmaceutical agents of this invention may be readily prepared by reacting the free base form of said second pharmaceutical agent with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a cosolvent from which the desired salt precipitates, or can be otherwise isolated by concentration and/or addition of a non-solvent.

In addition, zopolrestat ethanolamine, zopolrestat diethanolamine, zopolrestat triethanolamine and the second pharmaceutical agents which may be used in accordance with this invention, prodrugs of said second pharmaceutical agents and pharmaceutically acceptable salts of said second pharmaceutical agents or of said prodrugs, may occur as hydrates or solvates. Said hydrates and solvates are also within the scope of the invention.

This invention relates to methods of treating diabetic complications in which zopolrestat ethanolamine, zopolrestat diethanoalamine or zopolrestat triethanolamine is administered. Generally, in carrying out the methods of this invention, an effective dosage for zopolrestat ethanolamine, zopolrestat diethanolamine or zopolrestat triethanolamine is in the range of about 0.1 mg/kg/day to about 100 mg/kg/day in single or divided doses, preferably 0.1 mg/kg/day to about 20 mg/kg/day in single or divided doses.

This invention also relates both to methods of treating diabetic complications in which zopolrestat ethanolamine, zopolrestat diethanolamine or zopolrestat triethanolamine and the second pharmaceutical agent are administered together, as part of the same pharmaceutical composition, and to methods in which these two agents are administered separately, in any order, as part of an appropriate dosage regimen designed to obtain the benefits of the combination therapy. The appropriate dosage regimen, the amount of each dose administered and the intervals between doses of the active agents will depend upon the second pharmaceutical agent being used, the type of pharmaceutical formulations being used, the characteristics of the subject being treated and the severity of the complications. Generally, in carrying out the methods of this invention, an effective dosage for zopolrestat ethanolamine, zopolrestat diethanolamine or zopoirestat triethanolamine is in the range of about 0.1 mg/kg/day to about 100 mg/kg/day in single or divided doses, preferably 0.1 mg/kg/day to 20 mg/kg/day in single or divided doses.

When the second pharmaceutical agent is a SSRI, the SSRI will be administered in single or divided doses. SSRIs will generally be administered in amounts ranging from about 0.01 mg/kg/day to about 500 mg/kg/day in single or divided doses, preferably 10 mg/kg to about 300 mg/kg per day for an average subject, depending upon the SSRI and the route of administration. However, some variation in dosage will necessarily occur depending on the condition of the subject being treated. The prescribing physician will, in any event, determine the appropriate dose for the individual subject.

When the second pharmaceutical agent is a NHE-1 inhibitor, the NHE-1 inhibitor will be administered in single or divided doses. NHE-1 inhibitors will generally be administered in amounts ranging from about 0.001 mg/kg/day to about 100 mg/kg/day in single or divided doses, preferably 0.01 mg/kg to about 50 mg/kg per day for an average subject, depending upon the NHE-1 inhibitor and the route of administration. However, some variation in dosage will necessarily occur depending on the condition of the subject being treated. The prescribing physician will, in any event, determine the appropriate dose for the individual subject.

When the second pharmaceutical agent is a GPI, the GPI will be administered in single or divided doses. GPI s will generally be administered in amounts ranging from about 0.005 mg/kg/day to about 50 mg/kg/day in single or divided doses, preferably 0.01 mg/kg to about 25 mg/kg per day for an average subject and most preferably 0.1 mg/kg to about 15 mg/kg per day for an average subject, depending upon the GPI and the route of administration. However, some variation in dosage will necessarily occur depending on the condition of the subject being treated. The prescribing physician will, in any event, determine the appropriate dose for the individual subject.

When the second pharmaceutical agent is a SDI, the SDI will be administered in single or divided doses. SDIs will generally be administered in amounts ranging from about 0.001 mg/kg/day to about 100 mg/kg/day in single or divided doses, preferably 0.01 mg/kg to about 10 mg/kg per day for an average subject, depending upon the SDI and the route of administration. However, some variation in dosage will necessarily occur depending on the condition of the subject being treated. The prescribing physician will, in any event, determine the appropriate dose for the individual subject.

When the second pharmaceutical agent is an antihypertensive agent, the antihypertensive agent will be administered in single or divided doses. Antihypertensive agents will generally be administered in amounts ranging from about 0.01 mg/kg/day to about 500 mg/kg/day in single or divided doses, preferably 10 mg to about 300 mg per day for an average subject, depending upon the antihypertensive agent and the route of administration. However, some variation in dosage will necessarily occur depending on the condition of the subject being treated. The prescribing physician will, in any event, determine the appropriate dose for the individual subject.

Administration of zopolrestat ethanolamine, zopolrestat diethanolamine or zopolrestat triethanolamine and of the combination of one of said salts of zopolrestat and the second pharmaceutical agents of this invention can be via any method which delivers said zopolrestat ethanolamine, zopolrestat diethanolamine, zopolrestat triethanolamine or said combinations of this invention preferentially to the desired tissue (e.g., nerve, kidney, retina and/or cardiac tissues). These methods include oral routes, parenteral, intraduodenal routes, etc. Generally, zopolrestat ethanolamine, zopolrestat diethanolamine or zopolrestat triethanolamine and the combinations of the present invention are administered in single (e.g., once daily) or multiple doses or via constant infusion.

Pharmaceutical compositions comprising zopolrestat ethanolamine, zopolrestat diethanolamine, zopolrestat triethanolamine or a combination of one of said salts of zopolrestat and a second pharmaceutical agent of this invention are hereinafter referred to, collectively, as "the active compositions of this invention."

The active compositions of this invention may be administered to a subject in need of treatment by a variety of conventional routes of administration, including orally, topically, parenterally, e.g., intravenously, subcutaneously or intramedullary. Further, the active compositions of this invention may be administered intranasally, as a rectal suppository or using a "flash" formulation, i.e., allowing the medication to dissolve in the mouth without the need to use water.

The active compositions of this invention may be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the active compositions of this invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the active compositions of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Generally, an active composition of this invention is administered orally, or parenterally (e.g., intravenous, intramuscular, subcutaneous or intramedullary). Topical administration may also be indicated, for example, where the patient is suffering from gastrointestinal disorders or whenever the medication is best applied to the surface of a tissue or organ as determined by the attending physician.

For buccal administration the active composition of this invention (two active agents administered together or separately) may take the form of tablets or lozenges formulated in a conventional manner.

For intranasal administration or administration by inhalation, the active compositions of the invention (two active agents administered together or separately) are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound or combination of compounds. Capsules and cartridges (made, for example, from gelatin) for use in an inhaler or insufflator may be formulated containing a powder mix of a compound or compounds of the invention and a suitable powder base such as lactose or starch.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences,* Mack Publishing Company, Easton, Pa., 19th Edition (1995).

The active compositions of this invention contain an amount of both zopolrestat ethanolamine, zopolrestat diethanolamine or zopolrestat triethanolamine or an amount of one of said salts of zopoirestat and a second pharmaceutical agent of this invention. The amount of each of those ingredients may independently be, for example, 0.0001%–95% of the total amount of the composition, where the total amount may not, of course, exceed 100%. In any event, the composition or formulation to be administered will contain a quantity of each of the components of the composition according to the invention in an amount effective to treat the disease/condition of the subject being treated.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: zopolrestat ethanolamine, zopolrestat diethanolamine or zopolrestat triethanolamine; and a second pharmaceutical agent, a prodrug thereof or a pharmaceutically acceptable salt thereof or of said prodrug as described above. The kit comprises a container for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on a card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of the salt of zopolrestat can consist of one tablet or capsule while a daily dose of the second pharmaceutical agent can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Other features and advantages will be apparent from the specification and claims which describe the invention.

EXAMPLE ONE
[4-Oxo-(5-trifluoromethyl-benzothiazol-2-ylmethyl)-3,4-dihydro-phthalazin-1-yl]-acetic Acid Ethanolamine Salt.

To a solution of [4-oxo-(5-trifluoromethyl-benzothiazol-2-ylmethyl)-3,4-dihydro-phthalazin-1-yl]-acetic acid (419 mg, 1.0 mmol) in acetone (20 mL) was added ethanolamine (611 mg, 10.0 mmol). After stirring at ambient temperature for 1.0 hour, the mixture was evaporated to a semi-solid, which was crystallized from ethanol:diethyl ether (1:4) to afford the title compound as a white crystalline solid (460 mg, 95%). mp: 119–121° C.; $^1$H NMR (D$_2$O, 350 MHz): δ 3.30 (m, 2H), 3.66 (s, 2H), 3.79 (s, 6H), 5.47 (s, 2H), 7.19 (m, 1H), 7.48–7.71 (m, 5H), 7.99 (m, 1H).

EXAMPLE TWO

[4-Oxo-(5-trifluoromethyl-benzothiazol-2-ylmethyl)-3,4-dihydro-phthalazin-1-yl]-acetic Acid Diethanolamine Salt.

To a solution of [4-oxo-(5-trifluoromethyl-benzothiazol-2-ylmethyl)-3,4-dihydro-phthalazin-1-yl]-acetic acid (2.09 g, 5.0 mmol) in acetone (200 mL) was added diethanolamine (1.05 g, 10.0 mmol). After stirring at ambient temperature for 2.0 hours, the mixture was evaporated to a semi-solid, which was crystallized from ethanol:acetone (1:5) to afford the title compound as a white crystalline solid (2.12 g, 81%). mp: 163–164° C.; $^1$H NMR (D$_2$O, 350 MHz): δ 3.05 (m, 4H), 3.61 (s, 2H), 3.69 (m, 4H), 5.42 (s, 2H), 7.03 (m, 1H), 7.35 (m, 1H), 7.48–7.65 (m, 4H), 7.92 (m, 1H); MS (Cl) 419 (MH$^+$).

EXAMPLE THREE

[4-Oxo-(5-trifluoromethyl-benzothiazol-2-ylmethyl)-3,4-dihydro-phthalazin-1-yl]-acetic Acid Triethanolamine Salt.

To a solution of [4-oxo-(5-trifluoromethyl-benzothiazol-2-ylmethyl)-3,4-dihydro-phthalazin-1-yl]-acetic acid (419 mg, 1.0 mmol) in acetone (20 mL) was added triethanolamine (1.49 g, 10.0 mmol). After stirring at ambient temperature for 1.0 hours, the mixture was evaporated to a semi-solid, which was crystallized from ethanol:acetone (1:4) to afford the title compound as a white crystalline solid (494 mg, 86%). mp: 83–84° C.; $^1$H NMR (D$_2$O, 350 MHz): δ 3.30 (m, 6H), 3.67 (s, 2H), 3.79 (m, 6H), 5.47 (s, 2H), 7.17 (m, 1H), 7.48–7.71 (m, 5H), 8.01 (m, 1H); MS (Cl) 419 (MH).

It should be understood that the invention is not limited to the particular embodiments described herein, but that various changes and modifications may be made without departing from the spirit and scope of this invention as defined by the following claims.

What is claimed is:

1. A compound selected from the group consisting of 4-oxo-(5-trifluoromethyl-benzothiazol-2-ylmethyl)-3,4-dihydro-phthalazin-1-yl]-acetic acid ethanolamine salt; [4-oxo-(5-trifluoromethyl-benzothiazol-2-ylmethyl)-3,4-dihydro-phthalazin-1-yl]-acetic acid diethanolamine salt; and [4-oxo-(5-trifluoromethyl-benzothiazol-2-ylmethyl)-3,4-dihydro-phthalazin-1-yl]-acetic acid triethanolamine salt.

2. A pharmaceutical composition comprising a compound of claim 1 and a pharmaceutically acceptable carrier, vehicle or diluent.

3. The compound of claim 1 which is 4-oxo-(5-trifluoromethyl-benzothiazol-2-ylmethyl)-3,4-dihydro-phthalazin-1-yl]-acetic acid ethanolamine salt.

4. The compound of claim 1 which is [4-oxo-(5-trifluoromethyl-benzothiazol-2-ylmethyl)-3,4-dihydro-phthalazin-1-yl]-acetic acid diethanolamine salt.

5. The compound of claim 1 which is [4-oxo-(5-trifluoromethyl-benzothiazol-2-ylmethyl)-3,4-dihydro-phthalazin-1-yl]-acetic acid triethanolamine salt.

* * * * *